United States Patent [19]
Diab et al.

[11] Patent Number: 6,081,735
[45] Date of Patent: *Jun. 27, 2000

[54] SIGNAL PROCESSING APPARATUS

[75] Inventors: Mohamed K. Diab; Massi E. Kiani; Ibrahim M. Elfadel, all of Laguna Niguel; Rex J. McCarthy, Mission Viejo; Walter M. Weber, Los Angeles; Robert A. Smith, Corona, all of Calif.

[73] Assignee: Masimo Corporation, Irvine, Calif.

[ * ] Notice: This patent is subject to a terminal disclaimer.

[21] Appl. No.: 08/887,815

[22] Filed: Jul. 3, 1997

Related U.S. Application Data

[63] Continuation of application No. 08/859,837, May 16, 1997, which is a continuation of application No. 08/320,154, Oct. 7, 1994, Pat. No. 5,632,272, which is a continuation-in-part of application No. 08/132,812, Oct. 6, 1993, Pat. No. 5,490,505.

[51] Int. Cl.[7] .......................................... A61B 5/00

[52] U.S. Cl. ..................... 600/336; 600/481; 600/508; 600/529

[58] Field of Search .................... 600/300, 322, 600/323, 330, 336, 473, 476, 481, 500, 508, 509, 529

[56] References Cited

U.S. PATENT DOCUMENTS

| | | |
|---|---|---|
| 3,647,299 | 3/1972 | Lavallee . |
| 3,704,706 | 12/1972 | Herczfeld et al. . |
| 4,063,551 | 12/1977 | Sweeney . |
| 4,086,915 | 5/1978 | Kofsky et al. . |
| 4,095,117 | 6/1978 | Nagy . |
| 4,407,290 | 10/1983 | Wilber . |
| 4,537,200 | 8/1985 | Widrow . |
| 4,649,505 | 3/1987 | Zinser, Jr. et al. . |
| 4,723,294 | 2/1988 | Taguchi . |
| 4,773,422 | 9/1988 | Isaacson et al. . |
| 4,799,493 | 1/1989 | DuFault . |
| 4,800,495 | 1/1989 | Smith . |
| 4,819,752 | 4/1989 | Zelin . |
| 4,824,242 | 4/1989 | Frick et al. . |
| 4,848,901 | 7/1989 | Hood, Jr. . |
| 4,860,759 | 8/1989 | Kahn et al. . |
| 4,863,265 | 9/1989 | Flower et al. . |
| 4,867,571 | 9/1989 | Frick et al. . |
| 4,869,253 | 9/1989 | Craig, Jr. et al. . |
| 4,869,254 | 9/1989 | Stone et al. . |
| 4,883,353 | 11/1989 | Hausman . |
| 4,892,101 | 1/1990 | Cheung et al. . |
| 4,907,594 | 3/1990 | Muz . |

(List continued on next page.)

FOREIGN PATENT DOCUMENTS

| | | |
|---|---|---|
| 1674798 | 9/1991 | U.S.S.R. . |
| 92/15955 | 9/1992 | WIPO . |

OTHER PUBLICATIONS

Jingzheng, Ouyang et al., "Digital Processing of High–Resolution Electrocardiograms—Detection of His–Purkinje Activity from the Body Surface", *Biomedizinische Technik*, 33, Oct. 1, 1988, No. 10, Berlin, W. Germany, pp. 224–230.

(List continued on next page.)

*Primary Examiner*—Eric F. Winakur
*Attorney, Agent, or Firm*—Knobbe, Martens, Olson & Bear, LLP

[57] ABSTRACT

The present invention involves method and apparatus for analyzing two measured signals that are modeled as containing primary and secondary portions. Coefficients relate the two signals according to a model defined in accordance with the present invention. In one embodiment, the present invention involves utilizing a transformation which evaluates a plurality of possible signal coefficients in order to find appropriate coefficients. Alternatively, the present invention involves using statistical functions or Fourier transform and windowing techniques to determine the coefficients relating to two measured signals. Use of this invention is described in particular detail with respect to blood oximetry measurements.

28 Claims, 37 Drawing Sheets

U.S. PATENT DOCUMENTS

| | | |
|---|---|---|
| 4,911,167 | 3/1990 | Corenman et al. . |
| 4,927,264 | 5/1990 | Shiga et al. . |
| 4,928,692 | 5/1990 | Goodman et al. . |
| 4,948,248 | 8/1990 | Lehman . |
| 4,955,379 | 9/1990 | Hall . |
| 4,956,867 | 9/1990 | Zurek et al. . |
| 4,960,126 | 10/1990 | Conlon et al. . |
| 5,057,695 | 10/1991 | Hirao et al. . |
| 5,246,002 | 9/1993 | Prosser . |
| 5,273,036 | 12/1993 | Kronberg et al. . |
| 5,431,170 | 7/1995 | Mathews ................................. 600/323 |
| 5,458,128 | 10/1995 | Pulanyi et al. . |
| 5,632,272 | 5/1997 | Diab et al. ............................... 600/323 |

OTHER PUBLICATIONS

Chen, Jiande, et al., "Adaptive System for Processing of Electrogastric Signals", Images of the Twenty–First Century, Seattle, WA, vol. 11, Nov. 9–12, 1989. pp. 698–699.

Varanini, M. et al., "A Two Channel Adaptive Filtering Approach for Recognition of the QRS Morphology", Proceedings of the Computers in Cardiology Meeting, Venice, Sep. 23–26, 1991, Institute of Electrical and Electronics Engineers, pp. 141–144.

Rabiner, Lawrence et al. *Theory and Application of Digital Signal Processing,* p. 260, 1975.

Tremper, Kevin et al., *Advances in Oxygen Monitoring,* pp. 137–153, 1987.

Harris, Fred et al., "Digital Signal Processing with Efficient Polyphase Recursive All–Pass Filters", Presented at International Conference on Signal Processing, Florence, Italy, Sep. 4–6, 1991, 6 pages.

Haykin, Simon, *Adaptive Filter Theory,* Prentice Hall, Englewood Cliffs, NJ, 1991.

Widrow, Bernard, *Adaptive Signal Processing,* Prentice Hall, Englewood Cliffs, NJ 1985.

Brown, David P., "Evaluation of Pulse Oximeters using Theoretical Models and Experimental Studies", Master's thesis, University of Washington, Nov. 25, 1987, pp. 1–142.

Cohen, Arnon, "Volume I" Time and Frequency Domains Analysis, *Biomedical Signal Processing,* CRC Press, Inc., Boca Raton, Florida, pp. 152–159.

Severinghaus, J.W., "Pulse Oximetry Uses and Limitations", pp. 1–4, ASA Convention, New Orleans, 1989.

Mook, G.A., et al., "Spectrophotometric determination of Oxygen saturation of blood independent of the presence of indocyanine green", *Cardiovascular Research,* vol. 13, pp. 233–237, 1979.

Neuman, Michael R., "Pulse Oximetry: Physical Principles; Technical Realization and Present Limitations", *Continuous Transcutaneous Monitoring,* Plenum Press, New York, 1987, pp. 135–144.

Mook, G.A., et al., "Wavelength dependency of the spectrophotometric determination of blood oxygen saturation", *Clinical Chemistry Acta,* vol. 26, pp. 170–173, 1969.

Klimasauskas, Casey, "Neural Nets and Noise Filtering", *Dr. Dobb's Journal,* Jan. 1989, p. 32.

Melnikof, S. "Neural Networks for Signal Processing: A Case Study", *Dr. Dobbs Journal,* Jan. 1989. p. 36–37.

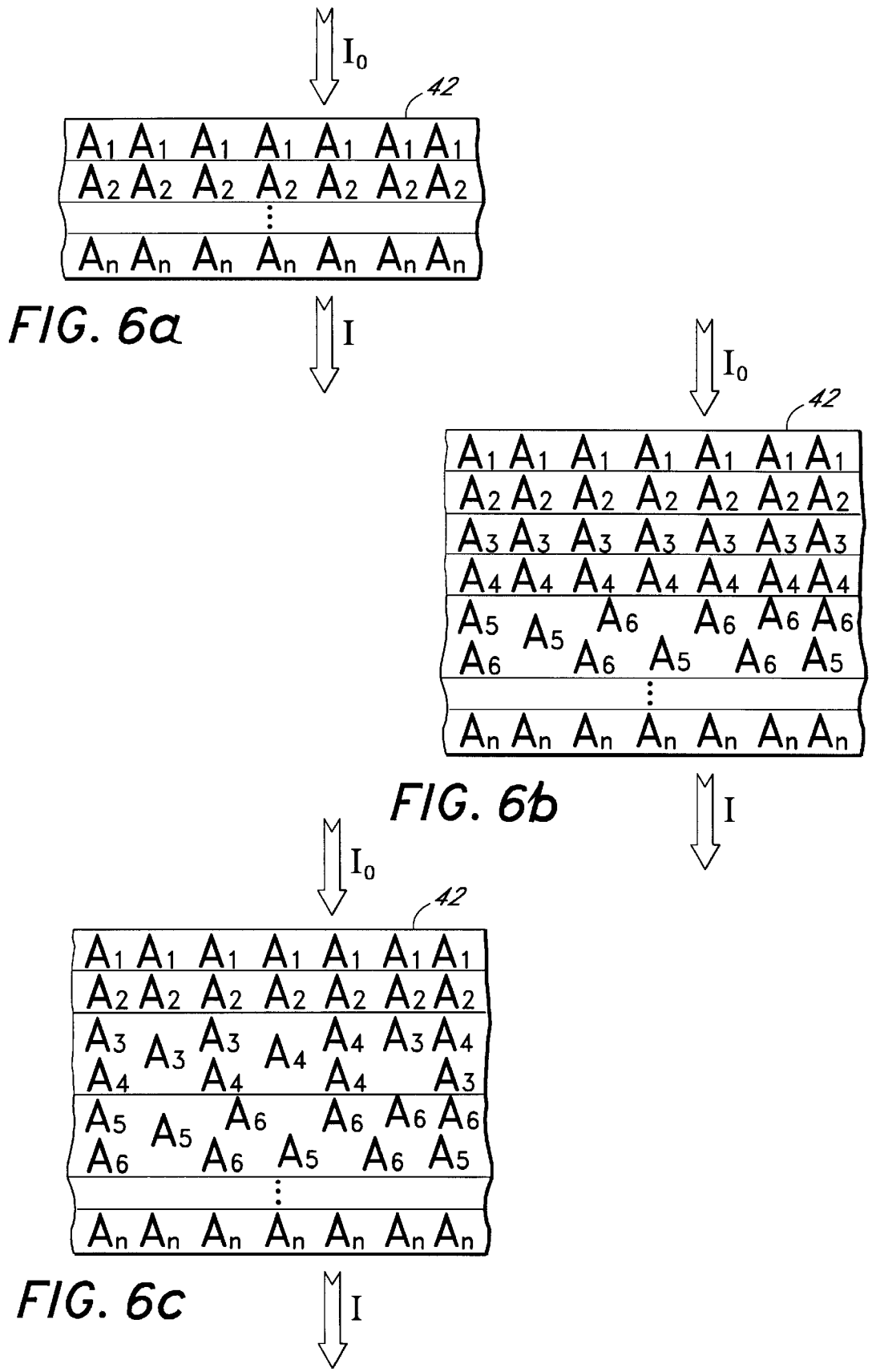

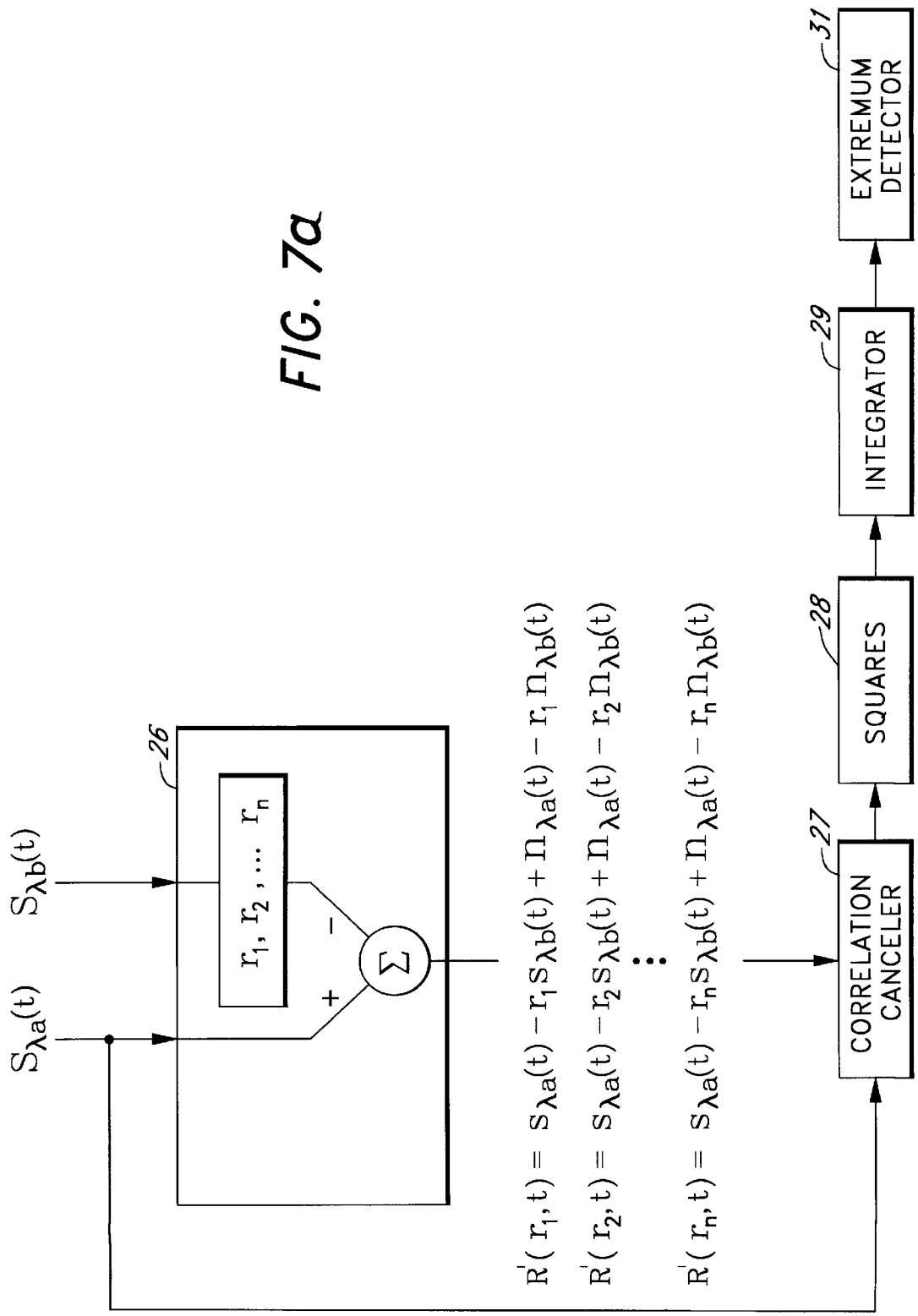

*FIG. 10*

SIGNAL PROCESSING APPARATUS

REFERENCE TO PRIOR RELATED APPLICATION

This is a continuation of application of U.S. patent application Ser. No. 08/859,837 filed May 16, 1997, which is a continuation of application of U.S. patent application Ser. No. 08/320,154 filed Oct. 7, 1994, now U.S. Pat. No. 5,632,272 which is a c-i-p of U.S. patent application Ser. No. 08/132,812 filed Oct. 6, 1993, now U.S. Pat. No. 5,490,505.

BACKGROUND OF THE INVENTION

1. Field of the Invention

The present invention relates to the field of signal processing. More specifically, the present invention relates to the processing of measured signals, containing a primary signal portion and a secondary signal portion, for the removal or derivation of either the primary or secondary signal portion when little is known about either of these components. More particularly, the present invention relates to modeling the measured signals in a novel way which facilitates minimizing the correlation between the primary signal portion and the secondary signal portion in order to produce a primary and/or secondary signal. The present invention is especially useful for physiological monitoring systems including blood oxygen saturation systems.

2. Description of the Related Art

Signal processors are typically employed to remove or derive either the primary or secondary signal portion from a composite measured signal including a primary signal portion and a secondary signal portion. For example, a composite signal may contain noise and desirable portions. If the secondary signal portion occupies a different frequency spectrum than the primary signal portion, then conventional filtering techniques such as low pass, band pass, and high pass filtering are available to remove or derive either the primary or the secondary signal portion from the total signal. Fixed single or multiple notch filters could also be employed if the primary and/or secondary signal portion(s) exist at a fixed frequency(s).

It is often the case that an overlap in frequency spectrum between the primary and secondary signal portions exists. Complicating matters further, the statistical properties of one or both of the primary and secondary signal portions change with time. In such cases, conventional filtering techniques are ineffective in extracting either the primary or secondary signal. If, however, a description of either the primary or secondary signal portion can be derived, correlation canceling, such as adaptive noise canceling, can be employed to remove either the primary or secondary signal portion of the signal isolating the other portion. In other words, given sufficient information about one of the signal portions, that signal portion can be extracted.

Conventional correlation cancilers, such as adaptive noise cancelers, dynamically change their transfer function to adapt to and remove portions of a composite signal. However, correlation cancelers require either a secondary reference or a primary reference which correlates to either the secondary signal portion only or the primary signal portion only. For instance, for a measured signal containing noise and desirable signal, the noise can be removed with a correlation canceler if a noise reference is available. This is often the case. Although the amplitude of the reference signals are not necessarily the same as the amplitude of the corresponding primary or secondary signal portions, they have a frequency spectrum which is similar to that of the primary or secondary signal portions.

In many cases, nothing or very little is known about the secondary and/or primary signal portions. One area where measured signals comprising a primary signal portion and a secondary signal portion about which no information can easily be determined is physiological monitoring. Physiological monitoring generally involves measured signals derived from a physiological system, such as the human body. Measurements which are typically taken with physiological monitoring systems include electrocardiographs, blood pressure, blood gas saturation (such as oxygen saturation), capnographs, other blood constituent monitoring, heart rate, respiration rate, electroencephalograph (EEG) and depth of anesthesia, for example. Other types of measurements include those which measure the pressure and quantity of a substance within the body such as cardiac output, venous oxygen saturation, arterial oxygen saturation, bilirubin, total hemoglobin, breathalyzer testing, drug testing, cholesterol testing, glucose testing, extra vasation, and carbon dioxide testing, protein testing, carbon monoxide testing, and other in-vivo measurements, for example. Complications arising in these measurements are often due to motion of the patient, both external and internal (muscle movement, vessel movement, and probe movement, for example), during the measurement process.

Many types of physiological measurements can be made by using the known properties of energy attenuation as a selected form of energy passes through a medium.

A blood gas monitor is one example of a physiological monitoring system which is based upon the measurement of energy attenuated by biological tissues or substances. Blood gas monitors transmit light into the test medium and measure the attenuation of the light as a function of time. The output signal of a blood gas monitor which is sensitive to the arterial blood flow contains a component which is a waveform representative of the patient's arterial pulse. This type of signal, which contains a component related to the patient's pulse, is called a plethysmographic wave, and is shown in FIG. 1 as curve s. Plethysmographic waveforms are used in blood gas saturation measurements. As the heart beats, the amount of blood in the arteries increases and decreases, causing increases and decreases in energy attenuation, illustrated by the cyclic wave s in FIG. 1.

Typically, a digit such as a finger, an ear lobe, or other portion of the body where blood flows close to the skin, is employed as the medium through which light energy is transmitted for blood gas attenuation measurements. The finger comprises skin, fat, bone, muscle, etc., shown schematically in FIG. 2, each of which attenuates energy incident on the finger in a generally predictable and constant manner. However, when fleshy portions of the finger are compressed erratically, for example by motion of the finger, energy attenuation becomes erratic.

An example of a more realistic measured waveform S is shown in FIG. 3, illustrating the effect of motion. The primary plethysmographic waveform portion of the signal s is the waveform representative of the pulse, corresponding to the sawtooth-like pattern wave in FIG. 1. The large, secondary motion-induced excursions in signal amplitude obscure the primary plethysmographic signal s. Even small variations in amplitude make it difficult to distinguish the primary signal component s in the presence of a secondary signal component n.

A pulse oximeter is a type of blood gas monitor which non-invasively measures the arterial saturation of oxygen in the blood. The pumping of the heart forces freshly oxygenated blood into the arteries causing greater energy attenuation. As well understood in the art, the arterial saturation of oxygenated blood may be determined from the depth of the valleys relative to the peaks of two plethysmographic waveforms measured at separate wavelengths. Patient movement introduces motion artifacts to the composite signal as illustrated in the plethysmographic waveform illustrated in FIG. 3. These motion artifacts distort the measured signal.

SUMMARY OF THE INVENTION

This invention provides improvements upon the methods and apparatus disclosed in U.S. patent application Ser. No. 08/132,812, filed Oct. 6, 1993, entitled Signal Processing Apparatus, which earlier application has been assigned to the assignee of the instant application. The present invention involves several different embodiments using the novel signal model in accordance with the present invention to isolate either a primary signal portion or a secondary signal portion of a composite measured signal. In one embodiment, a signal processor acquires a first measured signal and a second measured signal that is correlated to the first measured signal. The first signal comprises a first primary signal portion and a first secondary signal portion. The second signal comprises a second primary signal portion and a second secondary signal portion. The signals may be acquired by propagating energy through a medium and measuring an attenuated signal after transmission or reflection. Alternatively, the signals may be acquired by measuring energy generated by the medium.

In one embodiment, the first and second measured signals are processed to generate a secondary reference which does not contain the primary signal portions from either of the first or second measured signals. This secondary reference is correlated to the secondary signal portion of each of the first and second measured signals. The secondary reference is used to remove the secondary portion of each of the first and second measured signals via a correlation canceler, such as an adaptive noise canceler. The correlation canceler is a device which takes a first and second input and removes from the first input all signal components which are correlated to the second input. Any unit which performs or nearly performs this function is herein considered to be a correlation canceler.

An adaptive correlation canceler can be described by analogy to a dynamic multiple notch filter which dynamically changes its transfer function in response to a reference signal and the measured signals to remove frequencies from the measured signals that are also present in the reference signal. Thus, a typical adaptive correlation canceler receives the signal from which it is desired to remove a component and receives a reference signal of the undesired portion. The output of the correlation canceler is a good approximation to the desired signal with the undesired component removed.

Alternatively, the first and second measured signals may be processed to generate a primary reference which does not contain the secondary signal portions from either of the first or second measured signals. The primary reference may then be used to remove the primary portion of each of the first and second measured signals via a correlation canceler. The output of the correlation canceler is a good approximation to the secondary signal with the primary signal removed and may be used for subsequent processing in the same instrument or an auxiliary instrument. In this capacity, the approximation to the secondary signal may be used as a reference signal for input to a second correlation canceler together with either the first or second measured signals for computation of, respectively, either the first or second primary signal portions.

Physiological monitors can benefit from signal processors of the present invention. Often in physiological measurements a first signal comprising a first primary portion and a first secondary portion and a second signal comprising a second primary portion and a second secondary portion are acquired. The signals may be acquired by propagating energy through a patient's body (or a material which is derived from the body, such as breath, blood, or tissue, for example) or inside a vessel and measuring an attenuated signal after transmission or reflection. Alternatively, the signal may be acquired by measuring energy generated by a patient's body, such as in electrocardiography. The signals are processed via the signal processor of the present invention to acquire either a secondary reference or a primary reference which is input to a correlation canceler, such as an adaptive noise canceler.

One physiological monitoring apparatus which benefits from the present invention is a monitoring system which determines a signal which is representative of the arterial pulse, called a plethysmographic wave. This signal can be used in blood pressure calculations, blood constituent measurements, etc. A specific example of such a use is in pulse oximetry. Pulse oximetry involves determining the saturation of oxygen in the blood. In this configuration, the primary portion of the signal is the arterial blood contribution to attenuation of energy as it passes through a portion of the body where blood flows close to the skin. The pumping of the heart causes blood flow to increase and decrease in the arteries in a periodic fashion, causing periodic attenuation wherein the periodic waveform is the plethysmographic waveform representative of the arterial pulse. The secondary portion is noise. In accordance with the present invention, the measured signals are modeled such that this secondary portion of the signal is related to the venous blood contribution to attenuation of energy as it passes through the body. The secondary portion also includes artifacts due to patient movement which causes the venous blood to flow in an unpredictable manner, causing unpredictable attenuation and corrupting the otherwise periodic plethysmographic waveform. Respiration also causes the secondary or noise portion to vary, although typically at a lower frequency than the patients pulse rate. Accordingly, the measured signal which forms a plethysmographic waveform is modeled in accordance with the present invention such that the primary portion of the signal is representative of arterial blood contribution to attenuation and the secondary portion is due to several other parameters.

A physiological monitor particularly adapted to pulse oximetry oxygen saturation measurement comprises two light emitting diodes (LED's) which emit light at different wavelengths to produce first and second signals. A detector registers the attenuation of the two different energy signals after each passes through an absorptive media, for example a digit such as a finger, or an earlobe. The attenuated signals generally comprise both primary (arterial attenuator) and secondary (noise) signal portions. A static filtering system, such as a bandpass filter, removes a portion of the secondary signal which is outside of a known bandwidth of interest, leaving an erratic or random secondary signal portion, often caused by motion and often difficult to remove, along with the primary signal portion.

A processor in accordance with one embodiment of the present invention removes the primary signal portions from the measured signals yielding a secondary reference which is a combination of the remaining secondary signal portions. The secondary reference is correlated to both of the secondary signal portions. The secondary reference and at least one of the measured signals are input to a correlation canceler, such as an adaptive noise canceler, which removes the random or erratic portion of the secondary signal. This yields a good approximation to a primary plethysmographic signal as measured at one of the measured signal wavelengths. As is known in the art, quantitative measurements of the amount of oxygenated arterial blood in the body can be determined from the plethysmographic signal in a variety of ways.

The processor of the present invention may also remove the secondary signal portions from the measured signals yielding a primary reference which is a combination of the remaining primary signal portions. The primary reference is correlated to both of the primary signal portions. The primary reference and at least one of the measured signals are input to a correlation canceler which removes the primary portions of the measured signals. This yields a good approximation to the secondary signal at one of the measured signal wavelengths. This signal may be useful for removing secondary signals from an auxiliary instrument as well as determining venous blood oxygen saturation.

In accordance with the signal model of the present invention, the two measured signals each having primary and secondary signal portions can be related by coefficients. By relating the two equations with respect to coefficients defined in accordance with the present invention, the coefficients provide information about the arterial oxygen saturation and about the noise (the venous oxygen saturation and other parameters). In accordance with this aspect of the present invention, the coefficients can be determined by minimizing the correlation between the primary and secondary signal portions as defined in the model. Accordingly, the signal model of the present invention can be utilized in many ways in order to obtain information about the measured signals as will be further apparent in the detailed description of the preferred embodiments.

One aspect of the present invention is a method for use in a signal processor in a signal processor for processing at least two measured signals $S_1$ and $S_2$ each containing a primary signal portion s and a secondary signal portion n, the signals $S_1$ and $S_2$ being in accordance with the following relationship:

$$S_1 = s_1 + n_1$$
$$S_2 = s_2 + n_2$$

where $s_1$ and $s_2$, and $n_1$ and $n_2$ are related by:

$$s_1 = r_a s_2 \text{ and } n_1 = r_v n_2$$

and where $r_a$ and $r_v$ are coefficients.

The method comprises a number of steps. A value of coefficient $r_a$ is determined which minimize correlation between $s_1$ and $n_1$. Then, at least one of the first and second signals is processed using the determined value for $r_a$ to significantly reduce n from at least one of the first or second measured signal to form a clean signal.

In one embodiment, the clean signal is displayed on a display. In another embodiment, wherein the first and second signals are physiological signals, the method further comprises the step of processing the clean signal to determine a physiological parameter from the first or second measured signals. In one embodiment, the parameter is arterial oxygen saturation. In another embodiment, the parameter is an ECG signal. In yet another embodiment, wherein the first portion of the measured signals is indicative of a heart plethysmograph, the method further comprises the step of calculating the pulse rate.

Another aspect of the present invention involves a physiological monitor. The monitor has a first input configured to receive a first measured signal $S_1$ having a primary portion, $s_1$, and a secondary portion $n_1$. The monitor also has a second input configured to received a second measured signal $S_2$ having a primary portion $s_2$ and a secondary portion $n_2$. Advantageously, the first and the second measured signals $S_1$ and $S_2$ are in accordance with the following relationship:

$$S_1 = s_1 + n_1$$
$$S_2 = s_2 + n_2$$

where $s_1$ and $s_2$, and $n_1$ and $n_2$ are related by:

$$s_1 = r_a s_2 \text{ and } n_1 = r_v n_2$$

and where $r_a$ and $r_v$ are coefficients.

The monitor further has a scan reference processor, the scan reference processor responds to a plurality of possible values for $r_a$ to multiply the second measured signal by each of the possible values for $r_a$ and for each of the resulting values, to subtract the resulting values from the first measured signal to provide a plurality of output signals. A correlation canceler having a first input configured to receive the first measured signal, and having a second input configured to receive the plurality of output signals from the saturation scan reference processor, provides a plurality of output vectors corresponding to the correlation cancellation between the plurality of output signals and the first measured signal. An integrator having an input configured to receive the plurality of output vectors from the correlation canceler is responsive to the plurality of output vectors to determine a corresponding power for each output vector. An extremum detector is coupled at its input to the output of the integrator. The extremum detector is responsive to the corresponding power for each output vector to detect a selected power.

In one embodiment, the plurality of possible values correspond to a plurality of possible values for a selected blood constituent. In one embodiment the, the selected blood constituent is arterial blood oxygen saturation. In another embodiment, the selected blood constituent is venous blood oxygen saturation. In yet another embodiment, the selected blood constituent is carbon monoxide.

Another aspect of the present invention involves a physiological monitor. The monitor has a first input configured to receive a first measured signal $S_1$ having a primary portion, $s_1$, and a secondary portion, $n_1$. The monitor also has a second input configured to received a second measured signal $S_2$ having a primary portion $s_2$ and a secondary portion $n_2$. The first and the second measured signals $S_1$ and $S_2$ are in accordance with the following relationship:

$$S_1 = s_1 + n_1$$

$$S_2 = s_2 + n_2$$

where $s_1$ and $s_2$, and $n_1$ and $n_2$ are related by:

$$s_1 = r_a s_2 \text{ and } n_1 = r_v n_2$$

and where $r_a$ and $r_v$ are coefficients.

A transform module is responsive to the first and the second measured signals and responsive to a plurality of possible values for $r_a$ to provide at least one power curve as an output. An extremum calculation module is responsive to the at least one power curve to select a value for $r_a$ which minimizes the correlation between s and n, and to calculate from the value for $r_a$ a corresponding saturation value as an output. A display module is responsive to the output of saturation calculation to display the saturation value.

BRIEF DESCRIPTION OF THE DRAWINGS

FIG. 6a illustrates a schematic of absorbing material comprising N constituents within the absorbing material.

FIG. 6b illustrates another schematic of absorbing material comprising N constituents, including one mixed layer, within the absorbing material.

FIG. 6c illustrates another schematic of absorbing material comprising N constituents, including two mixed layers, within the absorbing material.

FIG. 7a illustrates a schematic diagram of a monitor, to compute primary and secondary signals in accordance with one aspect of the present invention.

FIG. 9a is a flowchart representing a subroutine for implementing in software a joint process estimator as modeled in FIG. 8a.

FIG. 10 is a schematic model of a joint process estimator with a least-squares lattice predictor and two regression filters.

DETAILED DESCRIPTION OF THE INVENTION

Figure 1:
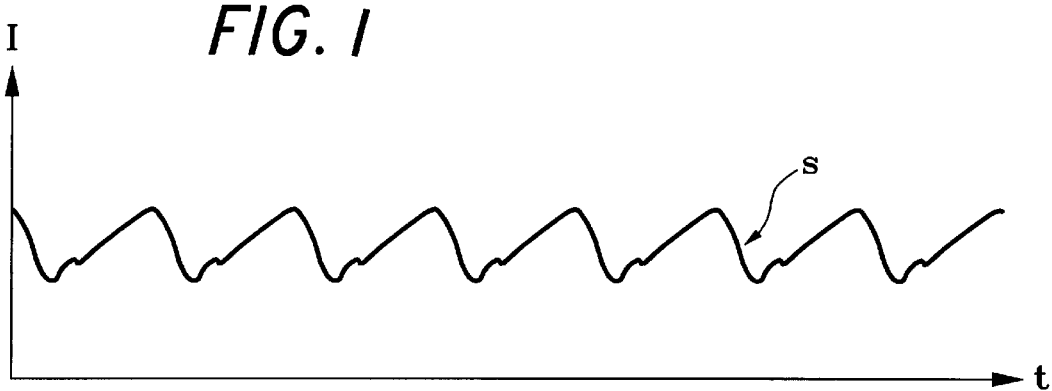
FIG. 1 illustrates an ideal plethysmographic waveform.

The present invention involves a system which utilizes first and second measured signals that each contain a primary signal portion and a secondary signal portion. In other words, given a first and second composite signals $S_1(t)=s_1(t)+n_1(t)$ and $S_2(t)=s_2(t)+n_2(t)$, the system of the present invention can be used to isolate either the primary signal portion s(t) or the secondary signal portion n(t). Following processing, the output of the system provides a good approximation n"(t) to the secondary signal portion n(t) or a good approximation s"(t) to the primary signal portion s(t).

The system of the present invention is particularly useful where the primary and/or secondary signal portion n(t) may contain one or more of a constant portion, a predictable portion, an erratic portion, a random portion, etc. The primary signal approximation s"(t) or secondary signal approximation n"(t) is derived by removing as many of the secondary signal portions n(t) or primary signal portions s(t) from the composite signal S(t) as possible. The remaining signal forms either the primary signal approximation s"(t) or secondary signal approximation n"(t), respectively. The constant portion and predictable portion of the secondary signal n(t) are easily removed with traditional filtering techniques, such as simple subtraction, low pass, band pass, and high pass filtering. The erratic portion is more difficult to remove due to its unpredictable nature. If something is known about the erratic signal, even statistically, it could be removed, at least partially, from the measured signal via traditional filtering techniques. However, often no information is known about the erratic portion of the secondary signal n(t). In this case, traditional filtering techniques are usually insufficient.

In order to remove the secondary signal n(t), a signal model in accordance with the present invention is defined as follows for the first and second measured signals $S_1$ and $S_2$:

$$r_a = \frac{s_1}{s_2} \text{ and } n_1 = \frac{n_1}{n_2}$$

where $s_1$ and $n_1$ are at least somewhat (preferably substantially) uncorrelated and $s_2$ and $n_2$ are at least somewhat (preferably substantially) uncorrelated. The first and second measured signals $S_1$ and $S_2$ are related by correlation coefficients $r_a$ and $r_v$ as defined above. The use and selection of these coefficients is described in further detail below.

In accordance with one aspect of the present invention, this signal model is used in combination with a correlation canceler, such as an adaptive noise canceler, to remove or derive the erratic portion of the measured signals.

Generally, a correlation canceler has two signal inputs and one output. One of the inputs is either the secondary reference n'(t) or the primary reference s'(t) which are correlated, respectively, to the secondary signal portions n(t) and the primary signal portions s(t) present in the composite signal S(t). The other input is for the composite signal S(t). Ideally, the output of the correlation canceler s"(t) or n"(t) corresponds, respectively, to the primary signal s(t) or the secondary signal n(t) portions only. Often, the most difficult task in the application of correlation cancelers is determining the reference signals n'(t) and s'(t) which are correlated to the secondary n(t) and primary s(t) portions, respectively, of the measured signal S(t) since, as discussed above, these portions are quite difficult to isolate from the measured signal S(t). In the signal processor of the present invention, either a secondary reference n'(t) or a primary reference s'(t) is determined from two composite signals measured simultaneously, or nearly simultaneously, at two different wavelengths, $\lambda$a and $\lambda$b.

Figure 4A:
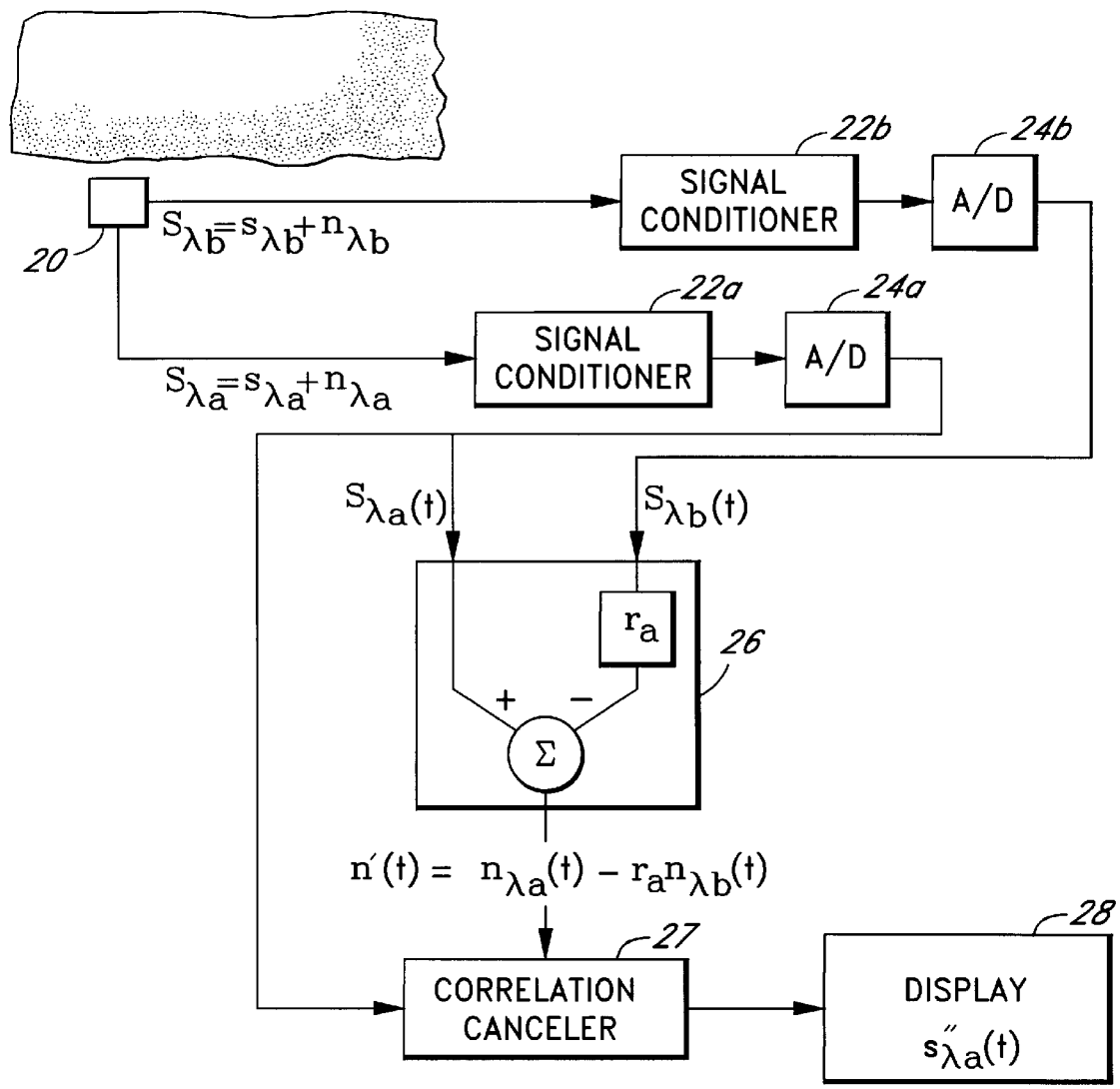
FIG. 4a illustrates a schematic diagram of a physiological monitor to compute primary physiological signals.
Figure 4B:
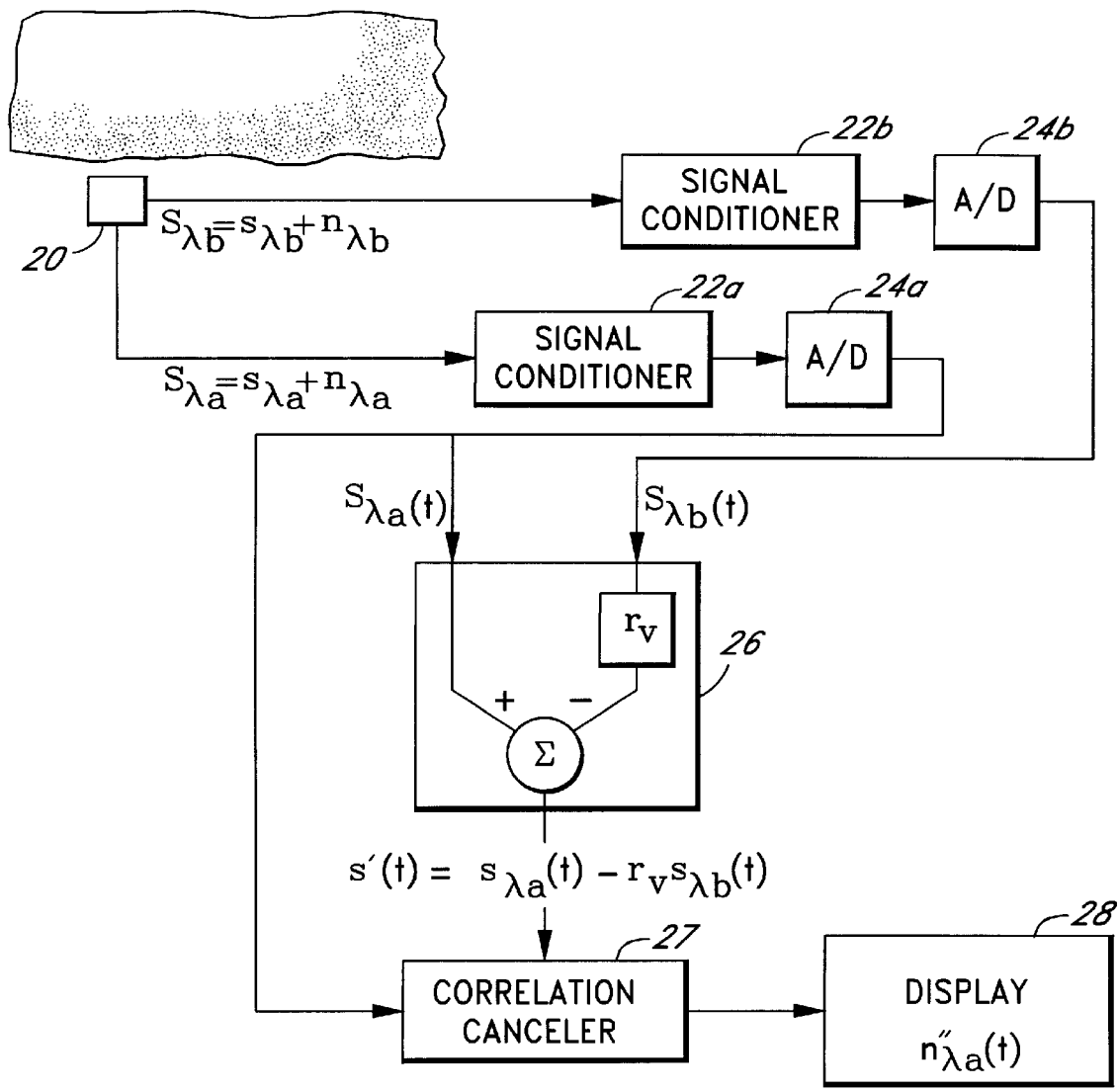
FIG. 4b illustrates a schematic diagram of a physiological monitor to compute secondary signals.

A block diagram of a generic monitor incorporating a signal processor according to the present invention, and a correlation canceler is shown in FIGS. 4a and 4b. Two measured signals, $S_{\lambda a}(t)$ and $S_{\lambda b}(t)$, are acquired by a detector 20. One skilled in the art will realize that for some physiological measurements, more than one detector may be advantageous. Each signal is conditioned by a signal conditioner 22a and 22b. Conditioning includes, but is not limited to, such procedures as filtering the signals to remove constant portions and amplifying the signals for ease of manipulation. The signals are then converted to digital data by an analog-to-digital converter 24a and 24b. The first measured signal $S_{\lambda a}(t)$ comprises a first primary signal portion, labeled herein $s_{\lambda a}(t)$, and a first secondary signal portion, labeled herein $n_{\lambda a}(t)$. The second measured signal $S_{\lambda b}(t)$ is at least partially correlated to the first measured signal $S_{\lambda a}(t)$ and comprises a second primary signal portion, labeled herein $s_{\lambda b}(t)$, and a second secondary signal portion, labeled herein $n_{\lambda b}(t)$. Typically the first and second secondary signal portions, $n_{\lambda a}(t)$ and $n_{\lambda b}(t)$, are uncorrelated and/or erratic with respect to the primary signal portions $s_{\lambda a}(t)$ and $s_{\lambda b}(t)$. The secondary signal portions $n_{\lambda a}(t)$ and $n_{\lambda b}(t)$ are often caused by motion of a patient in physiological measurements.

The signals $S_{\lambda a}(t)$ and $S_{\lambda b}(t)$ are input to a reference processor 26. The reference processor 26 multiplies the second measured signal $S_{\lambda b}(t)$ by either a factor $r_a=S_{\lambda a}(t)/S_{\lambda b}(t)$ or a factor $r_v=n_{\lambda a}(t)/n_{\lambda b}(t)$ and then subtracts the second measured signal $S_{\lambda b}(t)$ from the first measured signal $S_{\lambda a}(t)$. The signal coefficient factors $r_a$ and $r_v$ are determined to cause either the primary signal portions $s_{\lambda a}(t)$ and $s_{\lambda b}(t)$ or the secondary signal portions $n_{\lambda a}(t)$ and $n_{\lambda b}(t)$ to cancel, respectively, when the two signals $S_{\lambda a}(t)$ and $S_{\lambda b}(t)$ are subtracted. Thus, the output of the reference processor 26 is either a secondary reference signal $n'(t)=n_{\lambda a}(t)-r_a n_{\lambda b}(t)$, in FIG. 4a, which is correlated to both of the secondary signal portions $n_{\lambda a}(t)$ and $n_{\lambda b}(t)$ or a primary reference signal $s'(t)=s_{\lambda a}(t)-r_v s_{\lambda b}(t)$, in FIG. 4b, which is correlated to both of the primary signal portions $s_{\lambda a}(t)$ and $s_{\lambda b}(t)$. A reference signal n'(t) or s'(t) is input, along with one of the measured signals $S_{\lambda a}(t)$ or $S_{\lambda b}(t)$, to a correlation canceler 27 which uses the reference signal n'(t) or s'(t) to remove either the secondary signal portions $n_{\lambda a}(t)$ or $n_{\lambda b}(t)$ or the primary signal portions $s_{\lambda a}(t)$ or $s_{\lambda b}(t)$ from the measured signal $S_{\lambda a}(t)$ or $S_{\lambda b}(t)$. The output of the correlation canceler 27 is a good primary signal approximation s"(t) or secondary signal approximation n"(t). In one embodiment, the approximation s"(t) or n"(t) is displayed on a display 28.

In one embodiment, an adaptive noise canceler 30, an example of which is shown in block diagram form in FIG.

5a, is employed as the correlation canceler 27, to remove either one of the erratic, secondary signal portions $n_{\lambda a}(t)$ and $n_{\lambda b}(t)$ from the first and second signals $S_{\lambda a}(t)$ and $S_{\lambda b}(t)$. The adaptive noise canceler 30 in FIG. 5a has as one input a sample of the secondary reference n'(t) which is correlated to the secondary signal portions $n_{\lambda a}(t)$ and $n_{\lambda b}(t)$. The secondary reference n'(t) is determined from the two measured signals $S_{\lambda a}(t)$ and $S_{\lambda b}(t)$ by the processor 26 of the present invention as described herein. A second input to the adaptive noise canceler, is a sample of either the first or second composite measured signals $S_{\lambda a}(t)=s_{\lambda a}(t)+n_{\lambda a}(t)$ or $S_{\lambda b}(t)=s_{\lambda b}(t)+n_{\lambda b}(t)$.

Figure 5A:
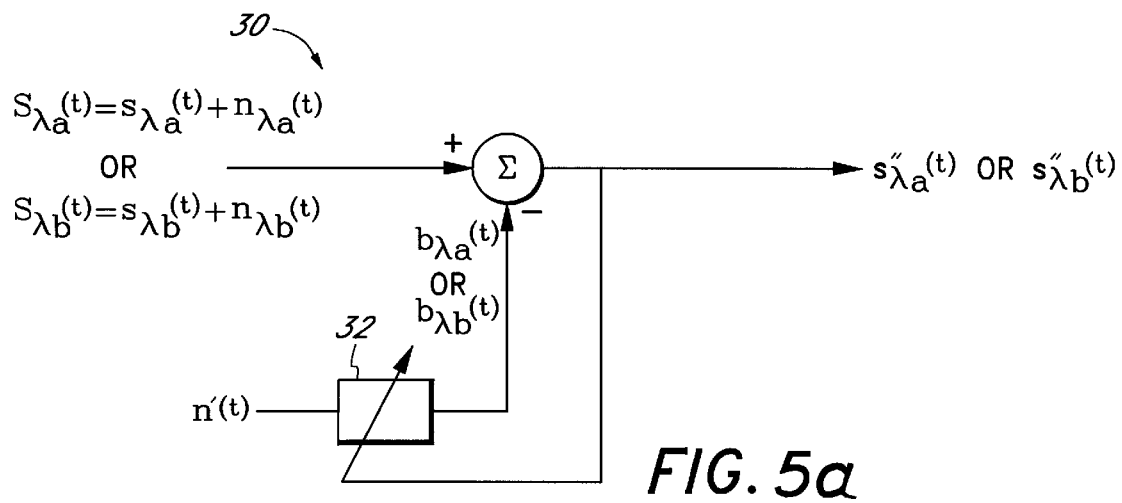
FIG. 5a illustrates an example of an adaptive noise canceler which could be employed in a physiological monitor, to compute primary physiological signals.
Figure 5B:
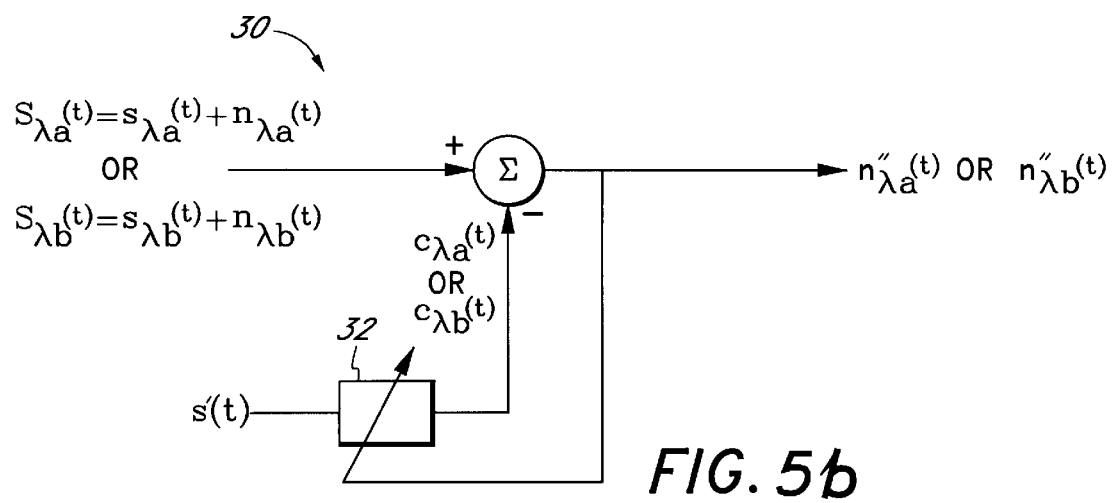
FIG. 5b illustrates an example of an adaptive noise canceler which could be employed in a physiological monitor, to compute secondary motion artifact signals.

The adaptive noise canceler 30, in FIG. 5b, may also be employed to remove either one of primary signal portions $s_{\lambda a}(t)$ and $s_{\lambda b}(t)$ from the first and second measured signals $S_{\lambda a}(t)$ and $S_{\lambda b}(t)$. The adaptive noise canceler 30 has as one input a sample of the primary reference s'(t) which is correlated to the primary signal portions $s_{\lambda a}(t)$ and $s_{\lambda b}(t)$. The primary reference s'(t) is determined from the two measured signals $S_{\lambda a}(t)$ and $S_{\lambda b}(t)$ by the processor 26 of the present invention as described herein. A second input to the adaptive noise canceler 30 is a sample of either the first or second measured signals $S_{\lambda a}(t)=s_{\lambda a}(t)+n_{\lambda a}(t)$ or $S_{\lambda b}(t)=s_{\lambda b}(t)+n_{\lambda b}(t)$.

The adaptive noise canceler 30 functions to remove frequencies common to both the reference n'(t) or s'(t) and the measured signal $S_{\lambda a}(t)$ or $S_{\lambda b}(t)$. Since the reference signals are correlated to either the secondary signal portions $n_{\lambda a}(t)$ and $n_{\lambda b}(t)$ or the primary signal portions $s_{\lambda a}(t)$ and $s_{\lambda b}(t)$, the reference signals will be correspondingly erratic or well behaved. The adaptive noise canceler 30 acts in a manner which may be analogized to a dynamic multiple notch filter based on the spectral distribution of the reference signal n'(t) or s'(t).

Figure 5C:
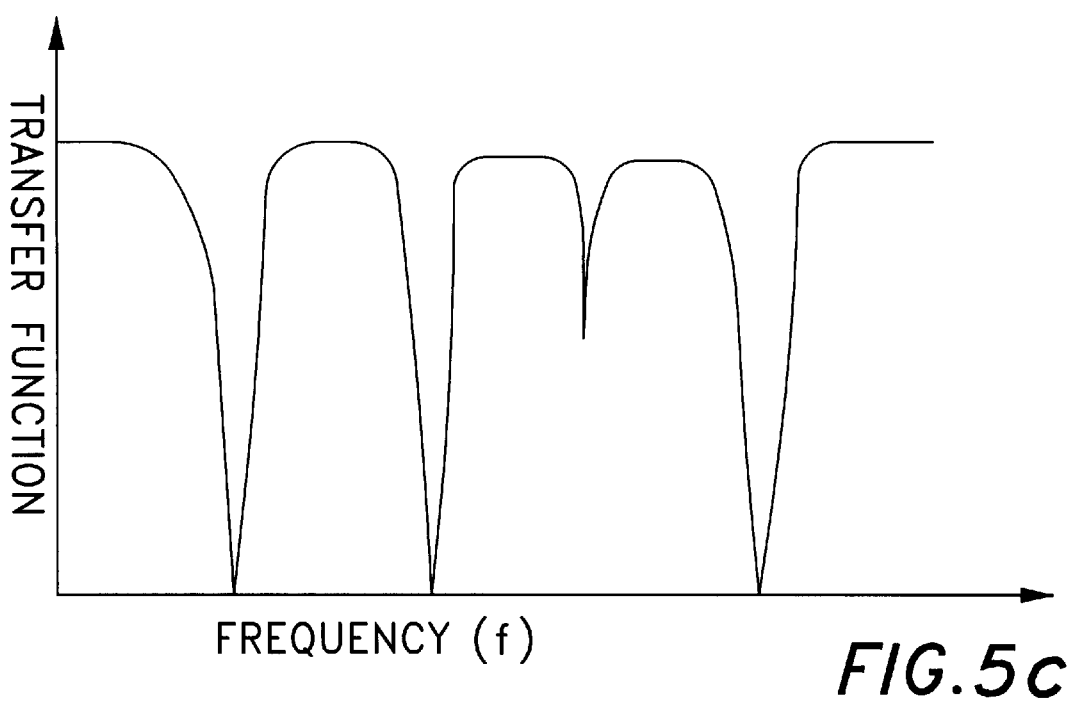
FIG. 5c illustrates the transfer function of a multiple notch filter.

FIG. 5c illustrates an exemplary transfer function of a multiple notch filter. The notches, or dips in the amplitude of the transfer function, indicate frequencies which are attenuated or removed when a signal passes through the notch filter. The output of the notch filter is the composite signal having frequencies at which a notch is present removed. In the analog to an adaptive noise canceler 30, the frequencies at which notches are present change continuously based upon the inputs to the adaptive noise canceler 30.

The adaptive noise canceler 30 (FIGS. 5a and 5b) produces an output signal, labeled herein as $s''_{\lambda a}(t)$, $s''_{\lambda b}(t)$, $n''_{\lambda a}(t)$ or $n''_{\lambda b}(t)$ which is fed back to an internal processor 32 within the adaptive noise canceler 30. The internal processor 32 automatically adjusts its own transfer function according to a predetermined algorithm such that the output of the internal processor 32 labeled $b_\lambda(t)$ in FIG. 5a and $c_\lambda(t)$ in FIG. 5b, closely resembles either the secondary signal portion $n_{\lambda a}(t)$ or $n_{\lambda b}(t)$ or the primary signal portion $s_{\lambda a}(t)$ or $s_{\lambda b}(t)$. The output $b_\lambda(t)$ of the internal processor 32 in FIG. 5a is subtracted from the measured signal, $S_{\lambda a}(t)$ or $S_{\lambda b}(t)$, yielding a signal output $s''_{\lambda a}(t)=s_{\lambda a}(t)+n_{\lambda a}(t)-b_{\lambda a}(t)$ or a signal output $s''_{\lambda b}(t)=s_{\lambda b}(t)+n_{\lambda b}(t)-b_{\lambda b}(t)$. The internal processor optimizes $s''_{\lambda a}(t)$ or $s''_{\lambda b}(t)$ such that $s''_{\lambda a}(t)$ or $s''_{\lambda b}(t)$ is approximately equal to the primary signal $s_{\lambda a}(t)$ or $s_{\lambda b}(t)$, respectively. The output $c_\lambda(t)$ of the internal processor 32 in FIG. 5b is subtracted from the measured signal, $S_{\lambda a}(t)$ or $S_{\lambda b}(t)$, yielding a signal output given by $n''_{\lambda a}(t)=s_{\lambda a}(t)+n_{\lambda a}(t)-c_{\lambda a}(t)$ or a signal output given by $n''_{\lambda b}(t)=s_{\lambda b}(t)+n_{\lambda b}(t)-c_{\lambda b}(t)$. The internal processor optimizes $n''_{\lambda a}(t)$ or $n''_{\lambda b}(t)$ such that $n''_{\lambda a}(t)$ or $n''_{\lambda b}(t)$ is approximately equal to the secondary signal portion $n_{\lambda a}(t)$ or $n_{\lambda b}(t)$, respectively.

One algorithm which may be used for the adjustment of the transfer function of the internal processor 32 is a least-squares algorithm, as described in Chapter 6 and Chapter 12 of the book *Adaptive Signal Processing* by Bernard Widrow and Samuel Stearns, published by Prentice Hall, copyright 1985. This entire book, including Chapters 6 and 12, is hereby incorporated herein by reference.

Adaptive processors 30 in FIGS. 5a and 5b have been successfully applied to a number of problems including antenna sidelobe canceling, pattern recognition, the elimination of periodic interference in general, and the elimination of echoes on long distance telephone transmission lines. However, considerable ingenuity is often required to find a suitable reference signal n'(t) or s'(t) since the portions $n_{\lambda a}(t)$, $n_{\lambda b}(t)$, $s_{\lambda a}(t)$ and $s_{\lambda b}(t)$ cannot easily be separated from the measured composite signals $S_{\lambda a}(t)$ and $S_{\lambda b}(t)$. If either the actual secondary portion $n_{\lambda a}(t)$ or $n_{\lambda b}(t)$ or the primary signal portion $s_{\lambda a}(t)$ or $S_{\lambda b}(t)$ were a priori available, techniques such as correlation cancellation would not be necessary.

GENERALIZED DETERMINATION OF PRIMARY AND SECONDARY REFERENCE SIGNALS

An explanation which describes how the reference signals n'(t) and s'(t) may be determined follows. A first signal is measured at, for example, a wavelength $\lambda a$, by a detector yielding a signal $S_{\lambda a}(t)$:

$$S_{\lambda a}(t)=s_{\lambda a}(t)+n_{\lambda a}(t) \tag{1}$$

where $s_{\lambda a}(t)$ is the primary signal portion and $n_{\lambda a}(t)$ is the secondary signal portion.

A similar measurement is taken simultaneously, or nearly simultaneously, at a different wavelength, $\lambda b$, yielding:

$$S_{\lambda b}(t)=s_{\lambda b}(t)+n_{\lambda b}(t) \tag{2}$$

Note that as long as the measurements, $S_{\lambda a}(t)$ and $S_{\lambda b}(t)$, are taken substantially simultaneously, the secondary signal components, $n_{\lambda a}(t)$ and $n_{\lambda b}(t)$, are correlated because any random or erratic functions affect each measurement in nearly the same fashion. The substantially predictable primary signal components, $s_{\lambda a}(t)$ and $s_{\lambda b}(t)$, are also correlated to one another.

To obtain the reference signals n'(t) and s'(t), the measured signals $S_{\lambda a}(t)$ and $S_{\lambda b}(t)$ are transformed to eliminate, respectively, the primary or secondary signal components. In accordance with the present invention one way of doing this is to find proportionality constants, $r_a$ and $r_v$, between the primary signal portions $S_{\lambda a}(t)$ and $s_{\lambda b}(t)$ and the secondary signal portions $n_{\lambda a}(t)$ and $n_{\lambda b}(t)$ such that the signals can be modeled as follows:

$$S_{\lambda a}(t)=r_a\, s_{\lambda b}(t)$$

$$n_{\lambda a}(t)=r_v\, n_{\lambda b}(t). \tag{3}$$

In accordance with the inventive signal model of the present invention, these proportionality relationships can be satisfied in many measurements, including but not limited to absorption measurements and physiological measurements. Additionally, in accordance with the signal model of the present invention, in most measurements, the proportionality constants $r_a$ and $r_v$ can be determined such that:

$$n_{\lambda a}(t) \neq r_a\, n_{\lambda b}(t)$$

$$s_{\lambda a}(t) \neq r_v \, s_{\lambda b}(t). \quad (4)$$

Multiplying equation (2) by $r_a$ and then subtracting equation (2) from equation (1) results in a single equation wherein the primary signal terms $s_{\lambda a}(t)$ and $s_{\lambda b}(t)$ cancel:

$$n'(t) = S_{\lambda a}(t) - r_a S_{\lambda b}(t) = n_{\lambda a}(t) - r_a n_{\lambda b}(t); \quad (5a)$$

a non-zero signal which is correlated to each secondary signal portion $n_{\lambda a}(t)$ and $n_{\lambda b}(t)$ and can be used as the secondary reference n'(t) in a correlation canceler such as an adaptive noise canceler.

Multiplying equation (2) by $r_v$ and then subtracting equation (2) from equation (1) results in a single equation wherein the secondary signal terms $n_{\lambda a}(t)$ and $n_{\lambda b}(t)$ cancel, leaving:

$$s'(t) = S_{\lambda a}(t) - r_v \, S_{\lambda b}(t) = s_{\lambda a}(t) - r_v \, s_{\lambda b}(t); \quad (5b)$$

a non-zero signal which is correlated to each of the primary signal portions $s_{\lambda a}(t)$ and $s_{\lambda b}(t)$ and can be used as the signal reference s'(t) in a correlation canceler such as an adaptive noise canceler.

EXAMPLE OF DETERMINATION OF PRIMARY AND SECONDARY REFERENCE SIGNALS IN AN ABSORPTIVE SYSTEM

Correlation canceling is particularly useful in a large number of measurements generally described as absorption measurements. An example of an absorption type monitor which can advantageously employ correlation canceling, such as adaptive noise canceling, based upon a reference n'(t) or s'(t) determined by a processor of the present invention is one which determines the concentration of an energy absorbing constituent within an absorbing material when the material is subject to change. Such changes can be caused by forces about which information is desired or primary, or alternatively, by random or erratic secondary forces such as a mechanical force on the material. Random or erratic interference, such as motion, generates secondary components in the measured signal. These secondary components can be removed or derived by the correlation canceler if a suitable secondary reference n'(t) or primary reference s'(t) is known.

A schematic N constituent absorbing material comprising a container 42 having N different absorbing constituents, labeled $A_1$, $A_2$, $A_3$, ... $A_N$, is shown in FIG. 6a. The constituents $A_1$ through $A_N$ in FIG. 6a are arranged in a generally orderly, layered fashion within the container 42. An example of a particular type of absorptive system is one in which light energy passes through the container 42 and is absorbed according to the generalized Beer-Lambert Law of light absorption. For light of wavelength $\lambda_a$, this attenuation may be approximated by:

$$I = I_o \exp\left(-\sum_{i=1}^{N} \epsilon_{i,\lambda a} c_i x_i\right) \quad (6)$$

Initially transforming the signal by taking the natural logarithm of both sides and manipulating terms, the signal is transformed such that the signal components are combined by addition rather than multiplication, i.e.:

$$S_{\lambda a} = \ln(I_0 / I) = \sum_{i=1}^{N} \epsilon_{i,\lambda a} c_i x_i \quad (7)$$

where $I_0$ is the incident light energy intensity; I is the transmitted light energy intensity; $\epsilon_{i,\lambda a}$ is the absorption coefficient of the $i^{th}$ constituent at the wavelength $\lambda a$; $x_i(t)$ is the optical path length of $i^{th}$ layer, i.e., the thickness of material of the $i^{th}$ layer through which optical energy passes; and $c_i(t)$ is the concentration of the $i^{th}$ constituent in the volume associated with the thickness $x_i(t)$. The absorption coefficients $\epsilon_1$ through $\epsilon_N$ are known values which are constant at each wavelength. Most concentrations $c_1(t)$ through $c_N(t)$ are typically unknown, as are most of the optical path lengths $x_i(t)$ of each layer. The total optical path length is the sum of each of the individual optical path lengths $x_i(t)$ of each layer.

When the material is not subject to any forces which cause change in the thicknesses of the layers, the optical path length of each layer, $x_i(t)$, is generally constant. This results in generally constant attenuation of the optical energy and thus, a generally constant offset in the measured signal. Typically, this offset portion of the signal is of little interest since knowledge about a force which perturbs the material is usually desired. Any signal portion outside of a known bandwidth of interest, including the constant undesired signal portion resulting from the generally constant absorption of the constituents when not subject to change, is removed. This is easily accomplished by traditional band pass filtering techniques. However, when the material is subject to forces, each layer of constituents may be affected by the perturbation differently than other layers. Some perturbations of the optical path lengths of each layer $x_i(t)$ may result in excursions in the measured signal which represent desired or primary information. Other perturbations of the optical path length of each layer $x_i(t)$ cause undesired or secondary excursions which mask primary information in the measured signal. Secondary signal components associated with secondary excursions must also be removed to obtain primary information from the measured signal. Similarly, the ability to compute secondary signal components caused by secondary excursions directly allows one to obtain primary signal components from the measured signal via simple subtraction, or correlation cancellation techniques.

The correlation canceler may selectively remove from the composite signal, measured after being transmitted through or reflected from the absorbing material, either the secondary or the primary signal components caused by forces which perturb or change the material differently from the forces which perturbed or changed the material to cause respectively, either the primary or secondary signal component. For the purposes of illustration, it will be assumed that the portion of the measured signal which is deemed to be the primary signal $s_{\lambda a}(t)$ is the attenuation term $\epsilon_5 c_5 x_5(t)$ associated with a constituent of interest, namely $A_5$, and that the layer of constituent $A_5$ is affected by perturbations different than each of the layers of other constituents $A_1$ through $A_4$ and $A_6$ through $A_N$. An example of such a situation is when layer $A_5$ is subject to forces about which information is deemed to be primary and, additionally, the entire material is subject to forces which affect each of the layers. In this case, since the total force affecting the layer of constituent $A_5$ is different than the total forces affecting each of the other layers and information is deemed to be primary about the forces and resultant perturbation of the layer of constituent $A_5$, attenuation terms due to constituents $A_1$ through $A_4$ and $A_6$ through $A_N$ make up the secondary signal portion $n_{\lambda a}(t)$. Even if the additional forces which affect the entire material cause the same perturbation in each layer, including the layer of $A_5$, the total forces on the layer of constituent $A_5$ cause it to have different total perturbation than each of the other layers of constituents $A_1$ through $A_4$ and $A_6$ through $A_N$.

It is often the case that the total perturbation affecting the layers associated with the secondary signal components is caused by random or erratic forces. This causes the thickness of layers to change erratically and the optical path length of each layer, $x_i(t)$, to change erratically, thereby producing a random or erratic secondary signal component $n_{\lambda a}(t)$. However, regardless of whether or not the secondary signal portion $n_{\lambda a}(t)$ is erratic, the secondary signal component $n_{\lambda a}(t)$ can be either removed or derived via a correlation canceler, such as an adaptive noise canceler, having as one input, respectively, a secondary reference n'(t) or a primary reference s'(t) determined by a processor of the present invention as long as the perturbation on layers other than the layer of constituent $A_5$ is different than the perturbation on the layer of constituent $A_5$. The correlation canceler yields a good approximation to either the primary signal $s_{\lambda a}(t)$ or the secondary signal $n_{\lambda a}(t)$. In the event that an approximation to the primary signal is obtained, the concentration of the constituent of interest, $c_5(t)$, can often be determined since in some physiological measurements, the thickness of the primary signal component, $x_5(t)$ in this example, is known or can be determined.

The correlation canceler utilizes either the secondary reference n'(t) or the primary reference s'(t) determined from two substantially simultaneously measured signals $S_{\lambda a}(t)$ and $S_{\lambda b}(t)$. $S_{\lambda a}(t)$ is determined as above in equation (7). $S_{\lambda b}(t)$ is determined similarly at a different wavelength $\lambda b$. To find either the secondary reference n'(t) or the primary reference s'(t), attenuated transmitted energy is measured at the two different wavelengths $\lambda_a$ and $\lambda_b$ and transformed via logarithmic conversion. The signals $S_{\lambda a}(t)$ and $S_{\lambda b}(t)$ can then be written (logarithm converted) as:

$$S_{\lambda a}(t) = \epsilon_{5,\lambda a} c_5 x_5(t) + \sum_{i=1}^{4} \epsilon_{i,\lambda a} c_i x_i + \sum_{i=6}^{N} \epsilon_{i,\lambda a} c_i x_i \tag{8}$$

$$S_{\lambda a(t)} = \epsilon_{5,\lambda a} c_5 x_5(t) + n_{\lambda a}(t) \tag{9}$$

$$S_{\lambda b(t)} = \epsilon_{5,\lambda b} c_5 x_5(t) + \sum_{i=1}^{4} \epsilon_{i,\lambda b} c_i x_i + \sum_{i=6}^{N} \epsilon_{i,\lambda b} c_i x_i \tag{10}$$

$$S_{\lambda b(t)} = \epsilon_{5,\lambda b} c_5 x_5(t) + n_{\lambda b}(t) \tag{11}$$

Further transformations of the signals are the proportionality relationships in accordance with the signal model of the present invention defining $r_a$ and $r_v$ similar to equation (3), which allows determination of a noise reference n'(t) and a primary reference s'(t) These are:

$$\epsilon_{5,\lambda a} = r_a \epsilon_{5,\lambda b} \tag{12a}$$

$$n_{\lambda a} = r_v n_{\lambda b} \tag{12b}$$

where $$n_{\lambda a} \neq r_a n_{80\ b} \tag{13a}$$

$$\epsilon_{5,\lambda a} \neq r_v \epsilon_{5,\lambda b}. \tag{13b}$$

It is often the case that both equations (12) and (13) can be simultaneously satisfied. Multiplying equation (11) by $r_a$ and subtracting the result from equation (9) yields a non-zero secondary reference which is a linear sum of secondary signal components:

$$n'(t) = S_{\lambda a}(t) - r_a S_{\lambda b}(t) = n_{\lambda a}(t) - r_a n_{\lambda b}(t) \tag{14a}$$

$$= \sum_{i=1}^{4} \epsilon_{i,\lambda a} c_i x_i(t) + \sum_{i=6}^{N} \epsilon_{i,\lambda a} c_i x_i(t) - \tag{15a}$$

$$\sum_{i=1}^{4} r_a \epsilon_{i,\lambda b} c_i x_i(t) + \sum_{i=6}^{N} r_a \epsilon_{i,\lambda b} c_i x_i(t)$$

$$= \sum_{i=1}^{4} c_i x_i(t)[\epsilon_{i,\lambda a} - r_a \epsilon_{i,\lambda b}] + \sum_{i=6}^{N} c_i x_i(t)[\epsilon_{i,\lambda a} - r_a \epsilon_{i,\lambda b}] \tag{16a}$$

Multiplying equation (11) by $r_v$ and subtracting the result from equation (9) yields a primary reference which is a linear sum of primary signal components:

$$s'(t) = S_{\lambda a}(t) - r_v S_{\lambda b}(t) = s_{\lambda a}(t) - r_v s_{\lambda b}(t) \tag{14b}$$

$$= c_5 x_5(t) \epsilon_{5,\lambda a} - r_v c_5 x_5(t) \epsilon_{5,\lambda b} \tag{15b}$$

$$= c_5 x_5(t)[\epsilon_{5,\lambda a} - r_v \epsilon_{5,\lambda b}]. \tag{16b}$$

A sample of either the secondary reference n'(t) or the primary reference s'(t), and a sample of either measured signal $S_{\lambda a}(t)$ or $S_{\lambda b}(t)$, are input to a correlation canceler 27, such as an adaptive noise canceler 30, an example of which is shown in FIGS. 5a and 5b and a preferred example of which is discussed herein under the heading PREFERRED CORRELATION CANCELER USING A JOINT PROCESS ESTIMATOR IMPLEMENTATION. The correlation canceler 27 removes either the secondary portion $n_{\lambda a}(t)$ or $n_{\lambda b}(t)$, or the primary portions, $s_{\lambda a}(t)$ or $s_{\lambda b}(t)$, of the measured signal yielding a good approximation to either the primary signal $s''_{\lambda a}(t) \approx \epsilon_{5,\lambda a} c_5 x_5(t)$ or $s''_{\lambda b}(t) \approx \epsilon_{5,\lambda b} c_5 x_5(t)$ or the secondary signals $n''_{\lambda a}(t) \approx n_{\lambda a}(t)$ or $n''_{\lambda b}(t) \approx n_{\lambda b}(t)$. In the event that the primary signals are obtained, the concentration $c_5(t)$ may then be determined from the approximation to the primary signal $s''_{\lambda a}(t)$ or $s''_{\lambda b}(t)$ according to:

$$c_5(t) \approx s''_{\lambda a}(t)/\epsilon_{5,\lambda a} x_5(t) \tag{17a}$$

or $$c_5(t) \approx s''_{\lambda b}(t)/\epsilon_{5,\lambda b} x_5(t) \tag{17b}$$

As discussed previously, the absorption coefficients are constant at each wavelength $\lambda a$ and $\lambda b$ and the thickness of the primary signal component, $x_5(t)$ in this example, is often known or can be determined as a function of time, thereby allowing calculation of the concentration $c_5(t)$ of constituent $A_5$.

DETERMINATION OF CONCENTRATION OR SATURATION IN A VOLUME CONTAINING MORE THAN ONE CONSTITUENT

Referring to FIG. 6b, another material having N different constituents arranged in layers is shown. In this material, two constituents $A_5$ and $A_6$ are found within one layer having thickness $x_{5,6}(t)=x_5(t)+x_6(t)$, located generally randomly within the layer. This is analogous to combining the layers of constituents $A_5$ and $A_6$ in FIG. 6a. A combination of layers, such as the combination of layers of constituents $A_5$ and $A_6$, is feasible when the two layers are under the same total forces which result in the same change of the optical path lengths $x_5$(t) and $x_6$(t) of the layers.

Often it is desirable to find the concentration or the saturation, i.e., a percent concentration, of one constituent within a given thickness which contains more than one constituent and is subject to unique forces. A determination of the concentration or the saturation of a constituent within a given volume may be made with any number of constituents in the volume subject to the same total forces and therefore under the same perturbation or change. To determine the saturation of one constituent in a volume comprising many constituents, as many measured signals as there are constituents which absorb incident light energy are necessary. It will be understood that constituents which do not absorb light energy are not consequential in the determination of saturation. To determine the concentration, as many signals as there are constituents which absorb incident light energy are necessary as well as information about the sum of concentrations.

It is often the case that a thickness under unique motion contains only two constituents. For example, it may be desirable to know the concentration or saturation of $A_5$ within a given volume which contains $A_5$ and $A_6$. In this case, the primary signals $s_{\lambda a}(t)$ and $s_{\lambda b}(t)$ comprise terms related to both $A_5$ and $A_6$ so that a determination of the concentration or saturation of $A_5$ or $A_6$ in the volume may be made. A determination of saturation is discussed herein. It will be understood that the concentration of $A_5$ in a volume containing both $A_5$ and $A_6$ could also be determined if it is known that $A_5+A_6=1$, i.e., that there are no constituents in the volume which do not absorb incident light energy at the particular measurement wavelengths chosen. The measured signals $S_{\lambda a}(t)$ and $S_{\lambda b}(t)$ can be written (logarithm converted) as:

$$S_{\lambda a}(t) = \epsilon_{5,\lambda a}c_5 x_{5,6}(t) + \epsilon_{6,\lambda a}c_6 x_{5,6}(t) + n_{\lambda a}(t) \tag{18a}$$

$$= s_{\lambda a}(t) + n_{\lambda a}(t) \tag{18b}$$

$$S_{\lambda b}(t) = \epsilon_{5,\lambda b}c_5 x_{5,6}(t) + \epsilon_{6,\lambda b}c_6 x_{5,6}(t) + n_{\lambda b}(t) \tag{19a}$$

$$= s_{\lambda b}(t) + n_{\lambda b}(t). \tag{19b}$$

It is also often the case that there may be two or more thicknesses within a medium each containing the same two constituents but each experiencing a separate motion as in FIG. 6c. For example, it may be desirable to know the concentration or saturation of $A_5$ within a given volume which contains $A_5$ and $A_6$ as well as the concentration or saturation of $A_3$ within a given volume which contains $A_3$ and $A_4$, $A_3$ and $A_4$ having the same constituency as $A_5$ and $A_6$ respectively. In this case, the primary signals $s_{\lambda a}(t)$ and $s_{\lambda b}(t)$ again comprise terms related to both $A_5$ and $A_6$ and portions of the secondary signals $n_{\lambda a}(t)$ and $n_{\lambda b}(t)$ comprise terms related to both $A_3$ and $A_4$. The layers, $A_3$ and $A_4$, do not enter into the primary equation because they are assumed to be perturbed by a different frequency, or random or erratic secondary forces which are uncorrelated with the primary force. Since constituents 3 and 5 as well as constituents 4 and 6 are taken to be the same, they have the same absorption coefficients (i.e., $\epsilon_{3,\lambda a}=\epsilon_{5,\lambda a}$; $\epsilon_{3,\lambda b}=\epsilon_{5,\lambda b}$; $\epsilon_{4,\lambda a}=\epsilon_{6,\lambda a}$ and $\epsilon_{4,\lambda b}=\epsilon_{6,\lambda b}$. Generally speaking, however, $A_3$ and $A_4$ will have different concentrations than $A_5$ and $A_6$ and will therefore have a different saturation. Consequently a single constituent within a medium may have one or more saturations associated with it. The primary and secondary signals according to this model may be written as:

$$s_{\lambda a}(t) = [\epsilon_{5,\lambda a}c_5 + \epsilon_{6,\lambda a}c_6]x_{5,6}(t) \tag{20a}$$

$$n_{\lambda a}(t) = [\epsilon_{5,\lambda a}c_3 + \epsilon_{6,\lambda a}c_4]x_{3,4}(t) + \sum_{i=1}^{2}\epsilon_{i,\lambda a}c_i x_i(t) + \sum_{i=7}^{N}\epsilon_{i,\lambda a}c_i x_i(t) \tag{20b}$$

$$n_{\lambda a}(t) = [\epsilon_{5,\lambda a}c_3 + \epsilon_{6,\lambda a}c_4]x_{3,4}(t) + n_{\lambda a}(t) \tag{20c}$$

$$s_{\lambda b}(t) = [\epsilon_{5,\lambda b}c_5 + \epsilon_{6,\lambda b}c_6]x_{5,6}(t) \tag{21a}$$

$$n_{\lambda b}(t) = [\epsilon_{5,\lambda b}c_3 + \epsilon_{6,\lambda b}c_4]x_{3,4}(t) + \sum_{i=1}^{2}\epsilon_{i,\lambda b}c_i x_i(t) + \sum_{i=7}^{N}\epsilon_{i,\lambda b}c_i x_i(t). \tag{21b}$$

$$n_{\lambda b}(t) = [\epsilon_{5,\lambda b}c_3 + \epsilon_{6,\lambda b}c_4]x_{3,4}(t) + n_{\lambda b}(t) \tag{21c}$$

where signals $n_{\lambda a}(t)$ and $n_{\lambda b}(t)$ are similar to the secondary signals $n_{\lambda a}(t)$ and $n_{\lambda b}(t)$ except for the omission of the 3, 4 layer.

Any signal portions whether primary or secondary, outside of a known bandwidth of interest, including the constant undesired secondary signal portion resulting from the generally constant absorption of the constituents when not under perturbation, should be removed to determine an approximation to either the primary signal or the secondary signal within the bandwidth of interest. This is easily accomplished by traditional band pass filtering techniques. As in the previous example, it is often the case that the total perturbation or change affecting the layers associated with the secondary signal components is caused by random or erratic forces, causing the thickness of each layer, or the optical path length of each layer, $x_i(t)$, to change erratically, producing a random or erratic secondary signal component $n_{\lambda a}(t)$. Regardless of whether or not the secondary signal portion $n_{\lambda a}(t)$ is erratic, the secondary signal component $n_{\lambda a}(t)$ can be removed or derived via a correlation canceler, such as an adaptive noise canceler, having as one input a secondary reference n'(t) or a primary reference s'(t) determined by a processor of the present invention as long as the perturbation in layers other than the layer of constituents $A_5$ and $A_6$ is different than the perturbation in the layer of constituents $A_5$ and $A_6$. Either the erratic secondary signal components $n_{\lambda a}(t)$ and $n_{\lambda b}(t)$ or the primary components $s_{\lambda a}(t)$ and $s_{\lambda b}(t)$ may advantageously be removed from equations (18) and (19), or alternatively equations (20) and (21), by a correlation canceler. The correlation canceler, again, requires a sample of either the primary reference s'(t) or the secondary reference n'(t) and a sample of either of the composite signals $S_{\lambda a}(t)$ or $S_{\lambda b}(t)$ of equations (18) and (19).

DETERMINATION OF PRIMARY AND SECONDARY REFERENCE SIGNALS FOR SATURATION MEASUREMENTS

One method for determining reference signals s'(t) or n'(t) from the measured signals $S_{\lambda a}(t)$ and $S_{\lambda b}(t)$ in accordance with one aspect of the invention is what will be referred to as the constant saturation approach. In this approach, it is assumed that the saturation of $A_5$ in the volume containing $A_5$ and $A_6$ and the saturation of $A_3$ in the volume containing $A_3$ and $A_4$ remains relatively constant over some period of time, i.e.:

$$\text{Saturation}(A_5(t)) = c_5(t)/[c_5(t)+c_6(t)] \quad (22a)$$

$$\text{Saturation}(A_3(t)) = c_3(t)/[c_3(t)+c_4(t)] \quad (22b)$$

$$\text{Saturation}(A_5(t)) = \{1+[c_6(t)/c_5(t)]\}^{-1} \quad (23a)$$

$$\text{Saturation}(A_3(t)) = \{1+[c_4(t)/c_3(t)]\}^{-1} \quad (23b)$$

are substantially constant over many samples of the measured signals $S_{\lambda a}$ and $S_{\lambda b}$. This assumption is accurate over many samples since saturation generally changes relatively slowly in physiological systems.

The constant saturation assumption is equivalent to assuming that:

$$c_5(t)/c_6(t) = \text{constant}_1 \quad (24a)$$

$$c_3(t)/c_4(t) = \text{constant}_2 \quad (24b)$$

since the only other term in equations (23a) and (23b) is a constant, namely the numeral 1.

Using this assumption, the proportionality constants $r_a$ and $r_v$ which allow determination of the secondary reference signal $n'(t)$ and the primary reference signal $s'(t)$ in the constant saturation method are:

$$r_a = \frac{\epsilon_{5,\lambda a} c_5 x_{5,6}(t) + \epsilon_{6,\lambda a} c_6 x_{5,6}(t)}{\epsilon_{5,\lambda b} c_5 x_{5,6}(t) + \epsilon_{6,\lambda b} c_6 x_{5,6}(t)} \quad (25a)$$

$$= s_{\lambda a}(t)/s_{\lambda b}(t) \quad (26a)$$

$$= \frac{\epsilon_{5,\lambda a} c_5 + \epsilon_{6,\lambda a} c_6}{\epsilon_{5,\lambda b} c_5 + \epsilon_{6,\lambda b} c_6} \quad (27a)$$

$$= \frac{\epsilon_{5,\lambda a}(c_5/c_6) + \epsilon_{6,\lambda a}}{\epsilon_{5,\lambda b}(c_5/c_6) + \epsilon_{6,\lambda b}} \quad (28a)$$

$$\approx s''_{\lambda a}(t)/s''_{\lambda b}(t) = \text{constant}_3; \text{ where} \quad (29a)$$

$$n_{\lambda a}(t) \neq r_a(t)n_{\lambda b}(t) \quad (30a)$$

and $$r_v = \frac{\epsilon_{5,\lambda a} c_3 x_{3,4}(t) + \epsilon_{6,\lambda a} c_4 x_{3,4}(t)}{\epsilon_{5,\lambda b} c_3 x_{3,4}(t) + \epsilon_{6,\lambda b} c_4 x_{3,4}(t))} \quad (25b)$$

$$= n_{\lambda a}(t)/n_{\lambda b}(t) \quad (26b)$$

$$= \frac{\epsilon_{5,\lambda a} c_3 + \epsilon_{6,\lambda a} c_4}{\epsilon_{5,\lambda b} c_3 + \epsilon_{6,\lambda b} c_4} \quad (27b)$$

$$= \frac{\epsilon_{5,\lambda a}(c_3/c_4) + \epsilon_{6,\lambda a}}{\epsilon_{5,\lambda b}(c_3/c_4) + \epsilon_{6,\lambda b}} \quad (28b)$$

$$\approx n''_{\lambda a}(t)/n''_{\lambda b}(t) = \text{constant}_4; \text{ where} \quad (29b)$$

$$s_{\lambda a}(t) \neq r_v(t)s_{\lambda b}(t). \quad (30b)$$

In accordance with the present invention, it is often the case that both equations (26) and (30) can be simultaneously satisfied to determine the proportionality constants $r_a$ and $r_v$. Additionally, the absorption coefficients at each wavelength $\epsilon_{5,\lambda a}$, $\epsilon_{6,\lambda a}$, $\epsilon_{5,\lambda b}$, and $\epsilon_{6,\lambda b}$ are constant and the central assumption of the constant saturation method is that $c_5(t)/c_6(t)$ and $c_3(t)/c_4(t)$ are constant over many sample periods. Thus, new proportionality constants $r_a$ and $r_v$ may be determined every few samples from new approximations to either the primary or secondary signal as output from the correlation canceler. Thus, the approximations to either the primary signals $s_{\lambda a}(t)$ and $s_{\lambda b}(t)$ or the secondary signals $n_{\lambda a}(t)$ and $n_{\lambda b}(t)$, found by the correlation canceler for a substantially immediately preceding set of samples of the measured signals $S_{\lambda a}(t)$ and $S_{\lambda b}(t)$ are used in a processor of the present invention for calculating the proportionality constants, $r_a$ and $r_v$, for the next set of samples of the measured signals $S_{\lambda a}(t)$ and $S_{\lambda b}(t)$.

Multiplying equation (19) by $r_a$ and subtracting the resulting equation from equation (18) yields a non-zero secondary reference signal:

$$n'(t) = S_{\lambda a}(t) - r_a S_{\lambda b}(t) = n_{\lambda a}(t) - r_a n_{\lambda b}(t). \quad (31a)$$

Multiplying equation (19) by $r_v$ and subtracting the resulting equation from equation (18) yields a non-zero primary reference signal:

$$s'(t) = S_{\lambda a}(t) - r_v S_{\lambda b}(t) = s_{\lambda a}(t) - r_v s_{\lambda b}(t). \quad (31b)$$

When using the constant saturation method in patient monitoring, initial proportionality coefficients can be determined as further explained below. It is not necessary for the patient to remain motionless even for an initialization period. With values for the proportionality coefficients $r_a$ and $r_v$ determined, a correlation canceler may be utilized with a secondary reference $n'(t)$ or a primary reference $s'(t)$.

DETERMINATION OF SIGNAL COEFFICIENTS FOR PRIMARY AND SECONDARY REFERENCE SIGNALS USING THE CONSTANT SATURATION METHOD

In accordance with one aspect of the present invention, the reference processor 26 of FIG. 4a and FIG. 4b of the present invention may be configured to multiply the second measured assumed signal $S_{\lambda b}(t) = s_{\lambda b}(t) + n_{\lambda b}(t)$ by each of a plurality of signal coefficients $r_1, r_2, \ldots r_n$ and then subtract each result from the first measured signal $S_{\lambda a}(t) = s_{\lambda a}(t) + n_{\lambda a}(t)$ to obtain a plurality of reference signals $$R'(r, t) = s_{\lambda a}(t) - r\, s_{\lambda b}(t) + n_{\lambda a}(t) - r\, n_{\lambda b}(t) \quad (32)$$

for $r = r_1, r_2, \ldots r_n$ as shown in FIG. 7a. In other words, a plurality of signal coefficients are chosen to represent a cross section of possible signal coefficients.

In order to determine either the primary reference $s'(t)$ or the secondary reference $n'(t)$ from the above plurality of reference signals of equation (32), signal coefficients $r_a$ and $r_v$ are determined from the plurality of assumed signal coefficients $r_1, r_2, \ldots r_n$. The coefficients $r_a$ and $r_v$ are selected such that they cause either the primary signal portions $s_{\lambda a}(t)$ and $s_{\lambda b}(t)$ or the secondary signal portions $n_{\lambda a}(t)$ and $n_{\lambda b}(t)$ to cancel or nearly cancel when they are substituted into the reference function $R'(r, t)$, e. g.

$$s_{\lambda a}(t) = r_a s_{\lambda b}(t) \quad (33a)$$

$$n_{\lambda a}(t) = r_v n_{\lambda b}(t) \quad (33b)$$

$$n'(t) = R'(r_a, t) = n_{\lambda a}(t) - r_a n_{\lambda b}(t) \quad (33c)$$

$$s'(t) = R'(r_v, t) = s_{\lambda a}(t) - r_v s_{\lambda b}(t). \quad (33d)$$

In other words, coefficients $r_a$ and $r_v$ are selected at values which reflect the minimum of correlation between the primary signal portions and the secondary signal portions. In practice, one does not usually have significant prior information about either the primary signal portions $s_{\lambda a}(t)$ and $s_{\lambda b}(t)$ or the secondary signal portions $n_{\lambda a}(t)$ and $n_{\lambda b}(t)$ of the measured signals $S_{\lambda a}(t)$ and $S_{\lambda b}(t)$. The lack of this information makes it difficult to determine which of the plurality of coefficients $r_1, r_2, \ldots r_n$ correspond to the signal coefficients $r_a = s_{\lambda a}(t)/s_{\lambda b}(t)$ and $r_v = n_{\lambda a}(t)/n_{\lambda b}(t)$.

Figure 7B:
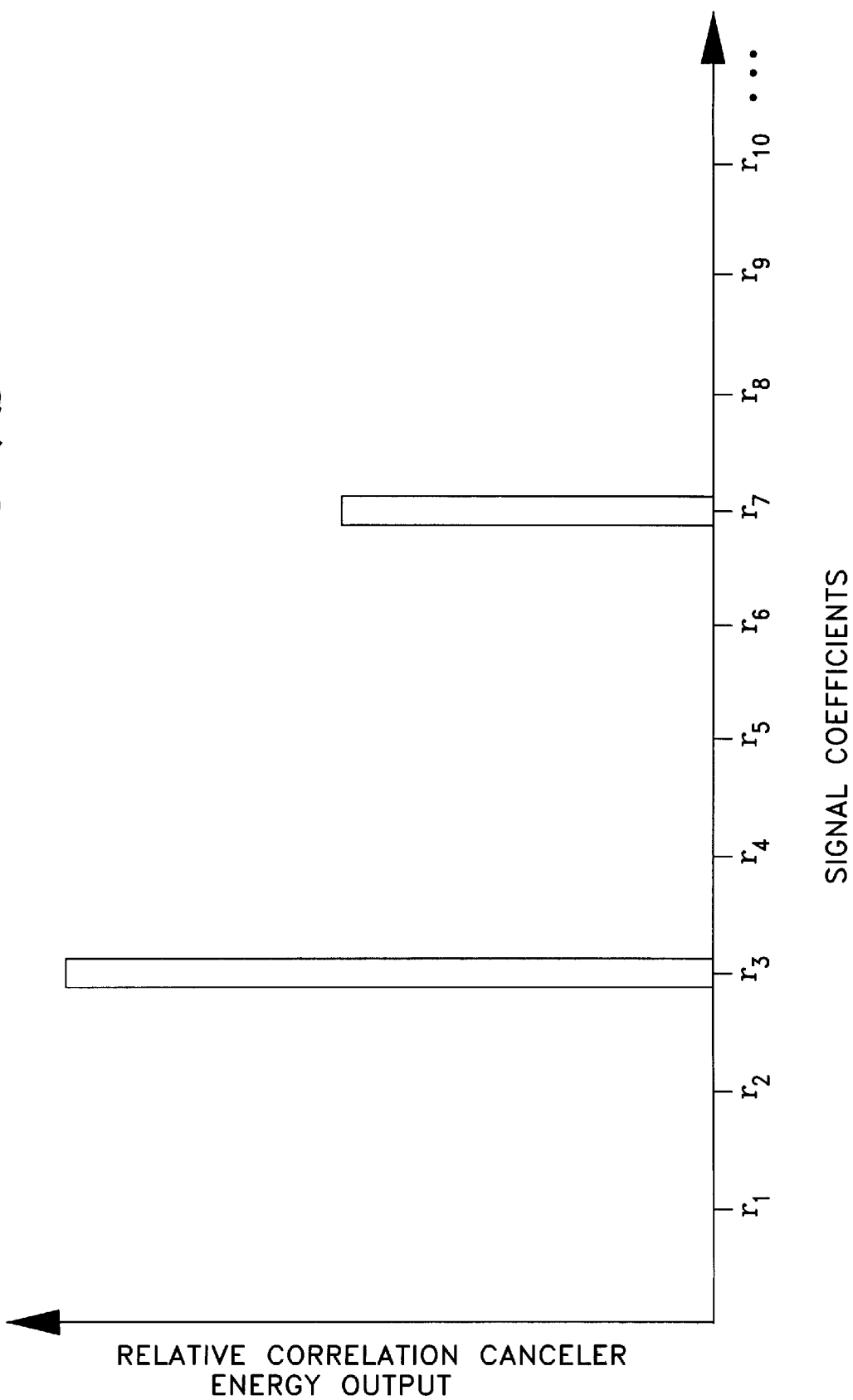
FIG. 7b illustrates the ideal correlation canceler energy or power output as a function of the signal coefficients $r_1$, $r_2$, ... $r_n$. In this particular example, $r_3 = r_a$ and $r_7 = r_v$.

One approach to determine the signal coefficients $r_a$ and $r_v$ from the plurality of coefficients $r_1, r_2, \ldots r_n$ employs the use of a correlation canceler 27, such as an adaptive noise canceler, which takes a first input which corresponds to one of the measured signals $S_{\lambda a}(t)$ or $S_{\lambda n}(t)$ and takes a second input which corresponds to successively each one of the plurality of reference signals $R'(r_1, t), R'(r_2, t), \ldots, R'(r_n, t)$ as shown in FIG. 7a. For each of the reference signals $R'(r_1, t), R'(r_2, t), \ldots, R'(r_n, t)$ the corresponding output of the correlation canceler 27 is input to a "squares" operation 28 which squares the output of the correlation canceler 27. The output of the squares operation 28 is provided to an integrator 29 for forming a cumulative output signal (a summation of the squares). The cumulative output signal is subsequently input to an extremum detector 31. The purpose of the extremum detector 31 is to chose signal coefficients $r_a$ and $r_v$ from the set $r_1, r_2, \ldots r_n$ by observing which provide a maximum in the cumulative output signal as in FIGS. 7b and 7c. In other words, coefficients which provide a maximum integrated output, such as energy or power, from the correlation canceler 27 correspond to the signal coefficients $r_a$ and $r_v$ which relate to a minimum correlation between the primary signal portions and the secondary signal portions in accordance with the signal model of the present invention. One could also configure a system geometry which would require one to locate the coefficients from the set $r_1, r_2, \ldots r_n$ which provide a minimum or inflection in the cumulative output signal to identify the signal coefficients $r_a$ and $r_v$.

Use of a plurality of coefficients in the processor of the present invention in conjunction with a correlation canceler 27 to determine the signal coefficients $r_a$ and $r_v$ may be demonstrated by using the properties of correlation cancellation. If x, y and z are taken to be any collection of three time varying signals, then the properties of some correlation cancelers C(x, y) may be defined as follows:

| Property (1) C(x, y)=0 for x, y correlated | (34a) |
| Property (2) C(x, y)=x for x, y uncorrelated | (34b) |
| Property (3) C(x+y, z)=C((x, z)+C(y, z) | (34c) |

With properties (1), (2) and (3) it is easy to demonstrate that the energy or power output of a correlation canceler with a first input which corresponds to one of the measured signals $S_{\lambda a}(t)$ or $S_{\lambda b}(t)$ and a second input which corresponds to successively each one of a plurality of reference signals $R'(r_1, t), R'(r_2, t), \ldots, R'(r_n, t)$ can determine the signal coefficients $r_a$ and $r_v$ needed to produce the primary reference s'(t) and secondary reference n'(t). If we take as a first input to the correlation canceler the measured signal $S_{\lambda a}(t)$ and as a second input the plurality of reference signals $R'(r_1, t), R'(r_2, t), \ldots, R'(r_n, t)$ then the outputs of the correlation canceler $C(S_{\lambda a}(t), R'(r_j, t))$ for $j=1, 2, \ldots, n$ may be written as $$C(s_{\lambda a}(t)+n_{\lambda a}(t), s_{\lambda a}(t)-r_j s_{\lambda b}(t)+n_{\lambda a}(t)-r_j n_{\lambda b}(t)) \qquad (35)$$

where $j=1, 2, \ldots, n$ and we have used the expressions $$R'(r, t) = S_{\lambda a}(t) - r S_{\lambda b}(t) \qquad (36)$$

$$S_{\lambda a}(t) = s_{\lambda a}(t) + n_{\lambda a}(t) \qquad (37a)$$

$$S_{\lambda b}(t) = s_{\lambda b}(t) + n_{\lambda b}(t). \qquad (37b)$$

The use of property (3) allows one to expand equation (35) into two terms $$C(S_{\lambda a}(t), R'(r, t)) = C(s_{\lambda a}(t), s_{\lambda a}(t) - r s_{\lambda b}(t) + n_{\lambda a}(t) - r n_{\lambda b}(t)) + \qquad (38)$$
$$C(n_{\lambda a}(t), s_{\lambda a}(t) - r s_{\lambda b}(t) + n_{\lambda a}(t) - r n_{\lambda b}(t))$$

so that upon use of properties (1) and (2) the correlation canceler output is given by $$C(S_{\lambda a}(t), R'(r_j, t)) s_{\lambda a}(t) \delta(r_j - r_a) + n_{\lambda a}(t) \delta(r_j - r_v) \qquad (39)$$

where $\delta(x)$ is the unit impulse function $$\delta(x) = 0 \text{ if } x \neq 0$$

$$\delta(x) = 1 \text{ if } x = 0. \qquad (40)$$

The time variable, t, of the correlation canceler output $C(S_{\lambda a}(t), R'(r_j, t))$ may be eliminated by computing its energy or power. The energy of the correlation canceler output is given by $$E_{\lambda a}(r_j) = \int C^2(S_{\lambda a}(t), R'(r_j, t)) dt \qquad (41a)$$
$$= \delta(r_j - r_a) \int s_{\lambda a}^2(t) dt + \delta(r_j - r_v) \int n_{\lambda a}^2(t) dt.$$

It should be understood that one could, equally well, have chosen the measured signal $S_{\lambda b}(t)$ as the first input to the correlation canceler and the plurality of reference signals $R'(r_1, t), R'(r_2, t), \ldots, R'(r_n, t)$ as the second input. In this event, the correlation canceler energy output is $$E_{\lambda b}(r_j) = \int C^2(S_{\lambda b}(t), R'(r, t)) dt \qquad (41b)$$
$$= \delta(r_j - r_a) \int s_{\lambda b}^2(t) dt + \delta(r_j - r_v) \int n_{\lambda b}^2(t) dt.$$

It should also be understood that in practical situations the use of discrete time measurement signals may be employed as well as continuous time measurement signals. A system which performs a discrete transform (e.g., a saturation transform in the present example) in accordance with the present invention is described with reference to FIGS. 11–22. In the event that discrete time measurement signals are used, integration approximation methods such as the trapezoid rule, midpoint rule, Tick's rule, Simpson's approximation or other techniques may be used to compute the correlation canceler energy or power output. In the discrete time measurement signal case, the energy output of the correlation canceler may be written, using the trapezoid rule, as $$E_{\lambda a}(r_j) = \delta(r_j - r_a)\Delta t \left\{ \sum_{i=0}^{n} s_{\lambda a}^2(t_i) - 0.5(s_{\lambda a}^2(t_0) + s_{\lambda a}^2(t_n)) \right\} + \quad (42a)$$

$$\delta(r_j - r_v)\Delta t \left\{ \sum_{i=0}^{n} n_{\lambda a}^2(t_i) - 0.5(n_{\lambda a}^2(t_0) + n_{\lambda a}^2(t_n)) \right\}$$

$$E_{\lambda b}(r) = \delta(r_j - r_a)\Delta t \left\{ \sum_{i=0}^{n} s_{\lambda b}^2(t_i) - 0.5(s_{\lambda b}^2(t_0) + s_{\lambda b}^2(t_n)) \right\} + \quad (42b)$$

$$\delta(r_j - r_v)\Delta t \left\{ \sum_{i=0}^{n} n_{\lambda b}^2(t_i) - 0.5(n_{\lambda b}^2(t_0) + n_{\lambda b}^2(t_n)) \right\}$$

where $t_i$ is the $i^{th}$ discrete time, $t_0$ is the initial time, $t_n$ is the final time and $\Delta t$ is the time between discrete time measurement samples.

The energy functions given above, and shown in FIG. 7b, indicate that the correlation canceler output is usually zero due to correlation between the measured signal $S_{\lambda a}(t)$ or $S_{\lambda b}(t)$ and many of the plurality of reference signals $R'(r_1, t)$, $R'(r_2, t), \ldots, R'(r_n, t)$. However, the energy functions are non zero at values of $r_j$ which correspond to cancellation of either the primary signal portions $s_{\lambda a}(t)$ and $s_{\lambda b}(t)$ or the secondary signal portions $n_{\lambda a}(t)$ and $n_{\lambda b}(t)$ in the reference signal $R'(r_j, t)$. These values correspond to the signal coefficients $r_a$ and $r_v$.

It should be understood that there may be instances in time when either the primary signal portions $s_{\lambda a}(t)$ and $s_{\lambda b}(t)$ or the secondary signal portions $n_{\lambda a}(t)$ and $n_{\lambda b}(t)$ are identically zero or nearly zero. In these cases, only one signal coefficient value will provide maximum energy or power output of the correlation canceler.

Since there may be more than one signal coefficient value which provides maximum correlation canceler energy or power output, an ambiguity may arise. It may not be immediately obvious which signal coefficient together with the reference function $R'(r, t)$ provides either the primary or secondary reference. In such cases, it is necessary to consider the constraints of the physical system at hand. For example, in pulse oximetry, it is known that arterial blood, whose signature is the primary plethysmographic wave, has greater oxygen saturation than venous blood, whose signature is the secondary erratic or random signal. Consequently, in pulse oximetry, the ratio of the primary signals due to arterial pulsation $r_a = s_{\lambda a}(t)/s_{\lambda b}(t)$ is the smaller of the two signal coefficient values while the ratio of the secondary signals due to mainly venous blood dynamics $r_v = n_{\lambda a}(t)/n_{\lambda b}(t)$ is the larger of the two signal coefficient values, assuming $\lambda a = 660$ nm and $\lambda b = 910$ nm.

Figure 7C:
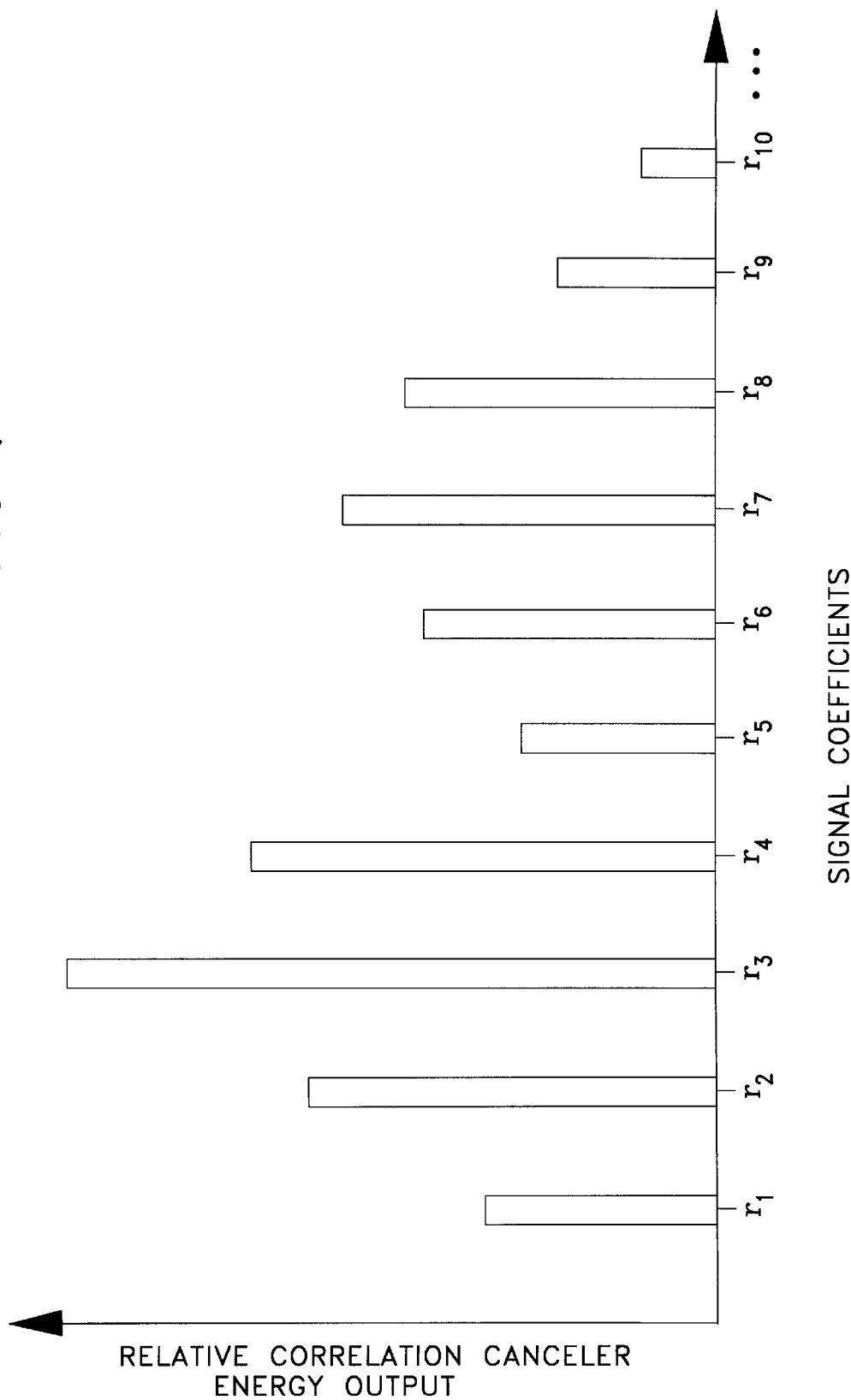
FIG. 7c illustrates the non-ideal correlation canceler energy or power output as a function of the signal coefficients $r_1$, $r_2$, ... $r_n$. In this particular example, $r_3 = r_a$ and $r_7 = r_v$.

It should also be understood that in practical implementations of the plurality of reference signals and cross correlator technique, the ideal features listed as properties (1), (2) and (3) above will not be precisely satisfied but will be approximations thereof. Therefore, in practical implementations of this embodiment of the present invention, the correlation canceler energy curves depicted in FIG. 7b will not consist of infinitely narrow delta functions but will have finite width associated with them as depicted in FIG. 7c.

It should also be understood that it is possible to have more than two signal coefficient values which produce maximum energy or power output from a correlation canceler. This situation arises when the measured signals each contain more than two components each of which are related by a ratio as follows:

$$S_\lambda a(t) = \sum_{i=0}^{n} f_{\lambda a,i}(t) \quad (43)$$

$$S_{\lambda b}(t) = \sum_{i=0}^{n} f_{\lambda b,i}(t)$$

where $$f_{\lambda a,i}(t) = r_i f_{\lambda b,i}(t)$$

$$i = 1, \ldots, n$$

$$r_i \neq r_j.$$

Thus, reference signal techniques together with a correlation cancellation, such as an adaptive noise canceler, can be employed to decompose a signal into two or more signal components each of which is related by a ratio.

PREFERRED CORRELATION CANCELER USING A JOINT PROCESS ESTIMATOR IMPLEMENTATION

Once either the secondary reference n'(t) or the primary reference s'(t) is determined by the processor of the present invention, the correlation canceler can be implemented in either hardware or software. The preferred implementation of a correlation canceler is that of an adaptive noise canceler using a joint process estimator.

The least mean squares (LMS) implementation of the internal processor 32 described above in conjunction with the adaptive noise canceler of FIG. 5a and FIG. 5b is relatively easy to implement, but lacks the speed of adaptation desirable for most physiological monitoring applications of the present invention. Thus, a faster approach for adaptive noise canceling, called a least-squares lattice joint process estimator model, is used in one embodiment. A joint process estimator 60 is shown diagrammatically in FIG. 8 and is described in detail in Chapter 9 of *Adaptive Filter Theory* by Simon Haykin, published by Prentice-Hall, copyright 1986. This entire book, including Chapter 9, is hereby incorporated herein by reference.

The function of the joint process estimator is to remove either the secondary signal portions $n_{\lambda a}(t)$ or $n_{\lambda b}(t)$ or the primary signal portions $s_{\lambda a}(t)$ or $s_{\lambda b}(t)$ from the measured signals $S_{\lambda a}(t)$ or $S_{\lambda b}(t)$, yielding either a primary signal approximation $s''_{\lambda a}(t)$ or $s''_{\lambda b}(t)$ or a secondary signal approximation $n''_{\lambda a}(t)$ or $n''_{\lambda b}(t)$. Thus, the joint process estimator estimates either the value of the primary signals $s_{\lambda a}(t)$ or $s_{\lambda b}(t)$ or the secondary signals $n_{\lambda a}(t)$ or $n_{\lambda b}(t)$. The inputs to the joint process estimator 60 are either the secondary reference n'(t) or the primary reference s'(t) and the composite measured signal $S_{\lambda a}(t)$ or $S_{\lambda b}(t)$. The output is a good approximation to the signal $S_{\lambda a}(t)$ or $S_{\lambda b}(t)$ with either the secondary signal or the primary signal removed, i.e. a good approximation to either $s_{\lambda a}(t)$, $s_{\lambda b}(t)$, $n_{\lambda a}(t)$ or $n_{\lambda b}(t)$.

Figure 8:
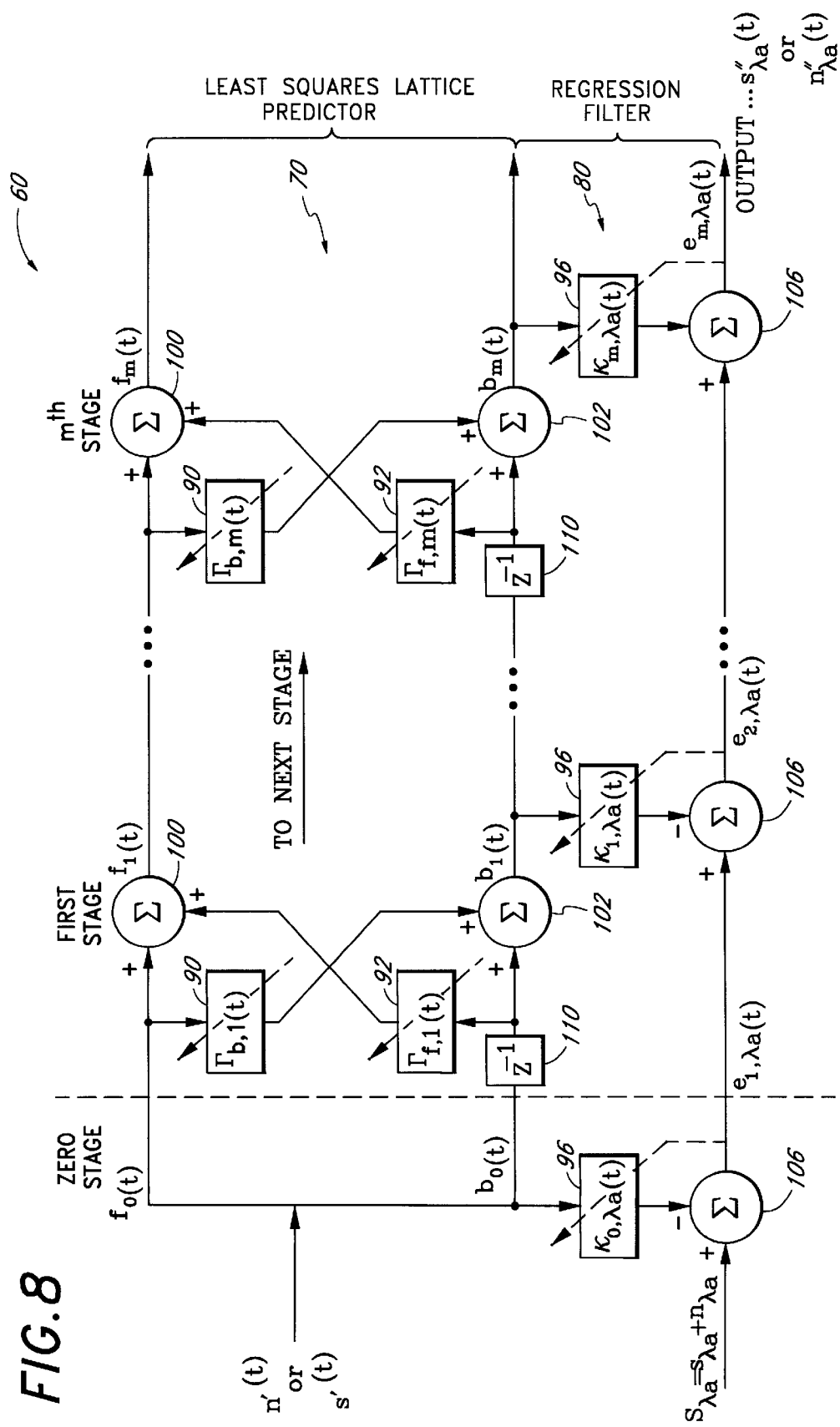
FIG. 8 is a schematic model of a joint process estimator comprising a least-squares lattice predictor and a regression filter.

The joint process estimator 60 of FIG. 8 utilizes, in conjunction, a least square lattice predictor 70 and a regression filter 80. Either the secondary reference n'(t) or the primary reference s'(t) is input to the least square lattice predictor 70 while the measured signal $S_{\lambda a}(t)$ or $S_{\lambda b}(t)$ is input to the regression filter 80. For simplicity in the following description, $S_{\lambda a}(t)$ will be the measured signal from which either the primary portion $s_{\lambda a}(t)$ or the secondary portion $n_{\lambda a}(t)$ will be estimated by the joint process estimator 60. However, it will be noted that $S_{\lambda b}(t)$ could also be input to the regression filter 80 and the primary portion $s_{\lambda b}(t)$ or the secondary portion $n_{\lambda b}(t)$ of this signal could be estimated.

The joint process estimator 60 removes all frequencies that are present in both the reference n'(t) or s'(t), and the measured signal $S_{\lambda a}(t)$. The secondary signal portion $n_{\lambda a}(t)$ usually comprises frequencies unrelated to those of the primary signal portion $s_{\lambda a}(t)$. It is improbable that the secondary signal portion $n_{\lambda a}(t)$ would be of exactly the same spectral content as the primary signal portion $s_{\lambda a}(t)$. However, in the unlikely event that the spectral content of $s_{\lambda a}(t)$ and $n_{\lambda a}(t)$ are similar, this approach will not yield accurate results. Functionally, the joint process estimator 60 compares the reference input signal n'(t) or s'(t), which is correlated to either the secondary signal portion $n_{\lambda a}(t)$ or the primary signal portion $s_{\lambda a}(t)$, and input signal $S_{\lambda a}(t)$ and removes all frequencies which are identical. Thus, the joint process estimator 60 acts as a dynamic multiple notch filter to remove those frequencies in the secondary signal component $n_{\lambda a}(t)$ as they change erratically with the motion of the patient or those frequencies in the primary signal component $s_{\lambda a}(t)$ as they change with the arterial pulsation of the patient. This yields a signal having substantially the same spectral content and amplitude as either the primary signal $s_{\lambda a}(t)$ or the secondary signal $n_{\lambda a}(t)$. Thus, the output $s''_{\lambda a}(t)$ or $n''_{\lambda a}(t)$ of the joint process estimator 60 is a very good approximation to either the primary signal $s_{\lambda a}(t)$ or the secondary signal $n_{\lambda a}(t)$.

The joint process estimator 60 can be divided into stages, beginning with a zero-stage and terminating in an $m^{th}$-stage, as shown in FIG. 8. Each stage, except for the zero-stage, is identical to every other stage. The zero-stage is an input stage for the joint process estimator 60. The first stage through the $m^{th}$-stage work on the signal produced in the immediately previous stage, i.e., the $(m-1)^{th}$-stage, such that a good primary signal approximation $s''_{\lambda a}(t)$ or secondary signal approximation $n''_{\lambda a}(t)$ is produced as output from the $m^{th}$-stage.

The least-squares lattice predictor 70 comprises registers 90 and 92, summing elements 100 and 102, and delay elements 110. The registers 90 and 92 contain multiplicative values of a forward reflection coefficient $\Gamma_{f,m}(t)$ and a backward reflection coefficient $\Gamma_{b,m}(t)$ which multiply the reference signal n'(t) or s'(t) and signals derived from the reference signal n'(t) or s'(t). Each stage of the least-squares lattice predictor outputs a forward prediction error $f_m(t)$ and a backward prediction error $b_m(t)$. The subscript m is indicative of the stage.

For each set of samples, i.e. one sample of the reference signal n'(t) or s'(t) derived substantially simultaneously with one sample of the measured signal $S_{\lambda a}(t)$, the sample of the reference signal n'(t) or s'(t) is input to the least-squares lattice predictor 70. The zero-stage forward prediction error $f_0(t)$ and the zero-stage backward prediction error $b_0(t)$ are set equal to the reference signal n'(t) or s'(t). The backward prediction error $b_0(t)$ is delayed by one sample period by the delay element 110 in the first stage of the least-squares lattice predictor 70. Thus, the immediately previous value of the reference n'(t) or s'(t) is used in calculations involving the first-stage delay element 110. The zero-stage forward prediction error is added to the negative of the delayed zero-stage backward prediction error $b_0(t-1)$ multiplied by the forward reflection coefficient value $\Gamma_{f,1}(t)$ register 90 value, to produce a first-stage forward prediction error $f_1(t)$. Additionally, the zero-stage forward prediction error $f_0(t)$ is multiplied by the backward reflection coefficient $\Gamma_{b,1}(t)$ register 92 value and added to the delayed zero-stage backward prediction error $b_0(t-1)$ to produce a first-stage backward prediction error $b_1(t)$. In each subsequent stage, m, of the least square lattice predictor 70, the previous forward and backward prediction error values, $f_{m-1}(t)$ and $b_{m-1}(t-1)$, the backward prediction error being delayed by one sample period, are used to produce values of the forward and backward prediction errors for the present stage, $f_m(t)$ and $b_m(t)$.

The backward prediction error $b_m(t)$ is fed to the concurrent stage, m, of the regression filter 80. There it is input to a register 96, which contains a multiplicative regression coefficient value $\kappa_{m,\lambda a}(t)$. For example, in the zero-stage of the regression filter 80, the zero-stage backward prediction error $b_0(t)$ is multiplied by the zero-stage regression coefficient $\kappa_{0,\lambda a}(t)$ register 96 value and subtracted from the measured value of the signal $S_{\lambda a}(t)$ at a summing element 106 to produce a first stage estimation error signal $e_{1,\lambda a}(t)$. The first-stage estimation error signal $e_{1,\lambda a}(t)$ is a first approximation to either the primary signal or the secondary signal. This first-stage estimation error signal $e_{1,\lambda a}(t)$ is input to the first-stage of the regression filter 80. The first-stage backward prediction error $b_1(t)$, multiplied by the first-stage regression coefficient $\kappa_{1,\lambda a}(t)$ register 96 value is subtracted from the first-stage estimation error signal $e_{1,\lambda a}(t)$ to produce the second-stage estimation error $e_{2,\lambda a}(t)$. The second-stage estimation error signal $e_{2,\lambda a}(t)$ is a second, somewhat better approximation to either the primary signal $s_{\lambda a}(t)$ or the secondary signal $n_{\lambda a}(t)$.

The same processes are repeated in the least-squares lattice predictor 70 and the regression filter 80 for each stage until a good approximation $e_{m,\lambda a}(t)$, to either the primary signal $s_{\lambda a}(t)$ or the secondary signal $n_{\lambda a}(t)$ is determined. Each of the signals discussed above, including the forward prediction error $f_m(t)$, the backward prediction error $b_m(t)$, the estimation error signal $e_{m,\lambda a}(t)$, is necessary to calculate the forward reflection coefficient $\Gamma_{f,m}(t)$, the backward reflection coefficient $\Gamma_{b,m}(t)$, and the regression coefficient $\kappa_{m,\lambda a}(t)$ register 90, 92, and 96 values in each stage, m. In addition to the forward prediction error $f_m(t)$, the backward prediction error $b_m(t)$, and the estimation error $e_{m,\lambda a}(t)$ signals, a number of intermediate variables, not shown in FIG. 8 but based on the values labeled in FIG. 8, are required to calculate the forward reflection coefficient $\Gamma_{f,m}(t)$, the backward reflection coefficient $\Gamma_{b,m}(t)$, and the regression coefficient $\kappa_{m,\lambda a}(t)$ register 90, 92, and 96 values.

Intermediate variables include a weighted sum of the forward prediction error squares $\Im_m(t)$, a weighted sum of the backward prediction error squares $\beta_m(t)$, a scalar parameter $\Delta_m(t)$, a conversion factor $\gamma_m(t)$, and another scalar parameter $\rho_{m,\lambda a}(t)$. The weighted sum of the forward prediction errors $\Im_m(t)$ is defined as:

$$\Im_m(t) = \sum_{i=1}^{t} \lambda^{t-i} |f_m(i)|^2; \qquad (44)$$

where $\lambda$ without a wavelength identifier, a or b, is a constant multiplicative value unrelated to wavelength and is typically less than or equal to one, i.e., $\lambda \leq 1$. The weighted sum of the backward prediction errors $\beta_m(t)$ is defined as:

$$\beta_m(t) = \sum_{i=1}^{t} \lambda^{t-i} |b_m(i)|^2 \qquad (45)$$

where, again, λ without a wavelength identifier, a or b, is a constant multiplicative value unrelated to wavelength and is typically less than or equal to one, i.e., $\lambda \leq 1$. These weighted sum intermediate error signals can be manipulated such that they are more easily solved for, as described in Chapter 9, § 9.3 of the Haykin book referenced above and defined hereinafter in equations (59:1 and (60).

DESCRIPTION OF THE JOINT PROCESS ESTIMATOR

The operation of the joint process estimator 60 is as follows. When the joint process estimator 60 is turned on, the initial values of intermediate variables and signals including the parameter $\Delta_{m-1}(t)$, the weighted sum of the forward prediction error signals $\Im_{m-1}(t)$, the weighted sum of the backward prediction error signals $\beta_{m-1}(t)$, the parameter $\rho_{m,\lambda a}(t)$, and the zero-stage estimation error $e_{0,\lambda a}(t)$ are initialized, some to zero and some to a small positive number δ:

$$\Delta_{m-1}(0)=0; \qquad (46)$$

$$\Im_{m-1}(0)=\delta; \qquad (47)$$

$$\beta_{m-1}(0)=\delta; \qquad (48)$$

$$\rho_{m,\lambda a}(0)=0; \qquad (49)$$

$$e_{0,\lambda a}(t)=S_{\lambda a}(t) \text{ for } t \geq 0. \qquad (50)$$

After initialization, a simultaneous sample of the measured signal $S_{\lambda a}(t)$ or $S_{\lambda b}(t)$ and either the secondary reference n'(t) or the primary reference s'(t) are input to the joint process estimator 60, as shown in FIG. 8. The forward and backward prediction error signals $f_0(t)$ and $b_0(t)$, and intermediate variables including the weighted sums of the forward and backward error signals $\Im_0(t)$ and $\beta_0(t)$, and the conversion factor $\gamma_0(t)$ are calculated for the zero-stage according to:

$$f_0(t)=b_0(t)=n'(t) \qquad (51a)$$

$$\Im_0(t)=\beta_0(t)=\lambda \Im_0(t-1)+|n'(t)|^2 \qquad (52a)$$

$$\gamma_0(t-1)=1 \qquad (53a)$$

if a secondary reference n'(t) is used or according to:

$$f_0(t)=b_0(t)=s'(t) \qquad (51b)$$

$$\Im_0(t)=\beta_0(t)=\lambda \Im_0(t-1)+|s'(t)|^2 \qquad (52b)$$

$$\gamma_0(t-1)=1 \qquad (53b)$$

if a primary reference s'(t) is used where, again, λ without a wavelength identifier, a or b, is a constant multiplicative value unrelated to wavelength.

Forward reflection coefficient $\Gamma_{f,m}(t)$, backward reflection coefficient $\Gamma_{b,m}(t)$, and regression coefficient $\kappa_{m,\lambda a}(t)$ register 90, 92 and 96 values in each stage thereafter are set according to the output of the previous stage. The forward reflection coefficient $\Gamma_{f,1}(t)$, backward reflection coefficient $\Gamma_{b,1}(t)$, and regression coefficient $\kappa_{1,\lambda a}(t)$ register 90, 92 and 96 values in the first stage are thus set according to the algorithm using values in the zero-stage of the joint process estimator 60. In each stage, $m \geq 1$, intermediate values and register values including the parameter $\Delta_{m-1}(t)$; the forward reflection coefficient $\Gamma_{f,m}(t)$ register 90 value; the backward reflection coefficient $\Gamma_{b,m}(t)$ register 92 value; the forward and backward error signals $f_m(t)$ and $b_m(t)$; the weighted sum of squared forward prediction errors $\Im_{f,m}(t)$, as manipulated in § 9.3 of the Haykin book; the weighted sum of squared backward prediction errors $\beta_{b,m}(t)$, as manipulated in § 9.3 of the Haykin book; the conversion factor $\gamma_m(t)$; the parameter $\rho_{m,\lambda a}(t)$; the regression coefficient $\kappa_{m,\lambda a}(t)$ register 96 value; and the estimation error $e_{m+1\lambda a}(t)$ value are set according to:

$$\Delta_{m-1}(t)=\lambda \Delta_{m-1}(t-1)+\{b_{m-1}(t-1)f^*_{m-1}(t)/\gamma_{m-1}(t-1)\} \qquad (54)$$

$$\Gamma_{f,m}(t)=-\{\Delta_{m-1}(t)/\beta_{m-1}(t-1)\} \qquad (55)$$

$$\Gamma_{b,m}(t)=-\{\Delta^*_{m-1}(t)/\Im_{m-1}(t)\} \qquad (56)$$

$$f_m(t)=f_{m-1}(t)+\Gamma^*_{f,m}(t)b_{m-1}(t-1) \qquad (57)$$

$$b_m(t)=b_{m-1}(t-1)+\Gamma^*_{b,m}(t)f_{m-1}(t) \qquad (58)$$

$$\Im_m(t)=\Im_{m-1}(t)-\{|\Delta_{m-1}(t)|^2/\beta_{m-1}(t-1)\} \qquad (59)$$

$$\beta_m(t)=\beta_{m-1}(t-1)-\{|\Delta_{m-1}(t)|^2/\Im_{m-1}(t)\} \qquad (60)$$

$$\gamma_m(t-1)=\gamma_{m-1}(t-1)-\{|b_{m-1}(t-1)|^2/\beta_{m-1}(t-1)\} \qquad (61)$$

$$\rho_{m,\lambda a}(t)=\lambda \rho_{m,\lambda a}(t-1)+\{b_m(t)\epsilon^*_{m,\lambda a}(t)/\gamma_m(t)\} \qquad (62)$$

$$\kappa_{m,\lambda a}(t)=\{\rho_{m,\lambda a}(t)/\beta_m(t)\} \qquad (63)$$

$$\epsilon_{m+1,\lambda a}(t)=\epsilon_{m,\lambda a}(t)-\kappa^*_m(t)b_m(t) \qquad (64)$$

where a (*) denotes a complex conjugate.

These equations cause the error signals $f_m(t)$, $b_m(t)$, $e_{m,\lambda a}(t)$ to be squared or to be multiplied by one another, in effect squaring the errors, and creating new intermediate error values, such as $\Delta_{m-1}(t)$. The error signals and the intermediate error values are recursively tied together, as shown in the above equations (54) through (64). They interact to minimize the error signals in the next stage.

After a good approximation to either the primary signal $s_{\lambda a}(t)$ or the secondary signal $n_{\lambda a}(t)$ has been determined by the joint process estimator 60, a next set of samples, including a sample of the measured signal $S_{\lambda a}(t)$ and a sample of either the secondary reference n'(t) or the primary reference s'(t), are input to the joint process estimator 60. The re-initialization process does not re-occur, such that the forward and backward reflection coefficient $\Gamma_{f,m}(t)$ and $\Gamma_{b,m}(t)$ register 90, 92 values and the regression coefficient $\kappa_{m,\lambda a}(t)$ register 96 value reflect the multiplicative values required to estimate either the primary signal portion $s_{\lambda a}(t)$ or the secondary signal portion $n_{\lambda a}(t)$ of the sample of $S_{\lambda a}(t)$ input previously. Thus, information from previous samples is used to estimate either the primary or secondary signal portion of a present set of samples in each stage.

In a more numerically stable and preferred embodiment of the above described joint process estimator, a normalized joint process estimator is used. This version of the joint process estimator normalizes several variables of the above-described joint process estimator such that the normalized variables fall between −1 and 1. The derivation of the normalized joint process estimator is motivated in the Haykin text as problem 12 on page 640 by redefining the variables defined according to the following conditions:

$$\overline{f}_m(t) = \frac{f_m(t)}{\sqrt{\mathcal{F}_m(t)\gamma_m(t-1)}}$$

$$\overline{b}(t) = \frac{b_m(t)}{\sqrt{\beta_m(t)\gamma_m(t)}}$$

$$\overline{\Delta}_m(t) = \frac{\Delta_m(t)}{\sqrt{\mathcal{F}_m(t)\beta_m(t-1)}}$$

This transformation allows the conversion of Equations (54)–(64) to the following normalized equations:

$$\overline{\Delta}_{m-1}(t) = \overline{\Delta}_{m-1}(t-1)[1-|\overline{f}_{m-1}(t)|^2]^{1/2}[1-|\overline{b}_{m-1}(t-1)|^2]^{1/2} +$$
$$\overline{b}_{m-1}(t-1)\overline{f}_{m-1}(t)$$

$$\overline{b}_m(t) = \frac{[\overline{b}_{m-1}(t-1) - \overline{\Delta}_{m-1}(t)\overline{f}_{m-1}(t)]}{\left[1-|\overline{\Delta}_{m-1}(t)|^2\right]^{1/2}\left[1-|\overline{f}_{m-1}(t)|^2\right]^{1/2}}$$

$$\overline{f}_m(t) = \frac{[\overline{f}_{m-1}(t) - \overline{\Delta}_{m-1}(t)\overline{b}_{m-1}(t-1)]}{\left[1-|\overline{\Delta}_{m-1}(t)|^2\right]^{1/2}\left[1-|\overline{b}_{m-1}(t-1)|^2\right]^{1/2}}$$

$$\beta_m(t) = \left[1-|\overline{\Delta}_{m-1}(t)|^2\right]\beta_{m-1}(t-1)$$

$$\gamma_m(t) = \gamma_{m-1}(t)\left[1-|\overline{b}_{m-1}(t)|^2\right]$$

$$\rho_m(t) = \lambda \cdot \left[\frac{\gamma_m(t)\beta_m(t-1)}{\gamma_m(t-1)\beta_m(t)}\right]^{1/2}\rho_m(t-1) + \overline{b}_m(t)\varepsilon_m(t)$$

$$\varepsilon_{m+1,\lambda a}(t) = \varepsilon_{m,\lambda a}(t) - \rho_m(t)\overline{b}_m(t)$$

Initialization of Normalized Joint Process Estimator

Let N(t) be defined as the reference noise input at time index n and U(t) be defined as combined signal plus noise input at time index t the following equations apply (see Haykin, p. 619):

1. To initialize the algorithm, at time t=0 set $$\overline{\Delta}_{m-1}(0)=0$$

$$\beta_{m-1}(0)=\delta=10^{-6}$$

$$\gamma_0(0)=1$$

2. At each instant $t \geq 1$, generate the various zeroth-order variables as follows:

$$\gamma_0(t-1)=1$$

$$\beta_0(t)=\lambda\beta_0(t-1)+N^2(t)$$

$$\overline{b}_0(t) = \overline{f}_0(t) = \frac{N(t)}{\sqrt{\beta_0(t)}}$$

3. For regression filtering, initialize the algorithm by setting at time index t=0

$$\rho_m(0)=0$$

4. At each instant $t \geq 1$, generate the zeroth-order variable $$\varepsilon_0(t)=U(t).$$

Accordingly, a normalized joint process estimator can be used for a more stable system.

Figure 8A:
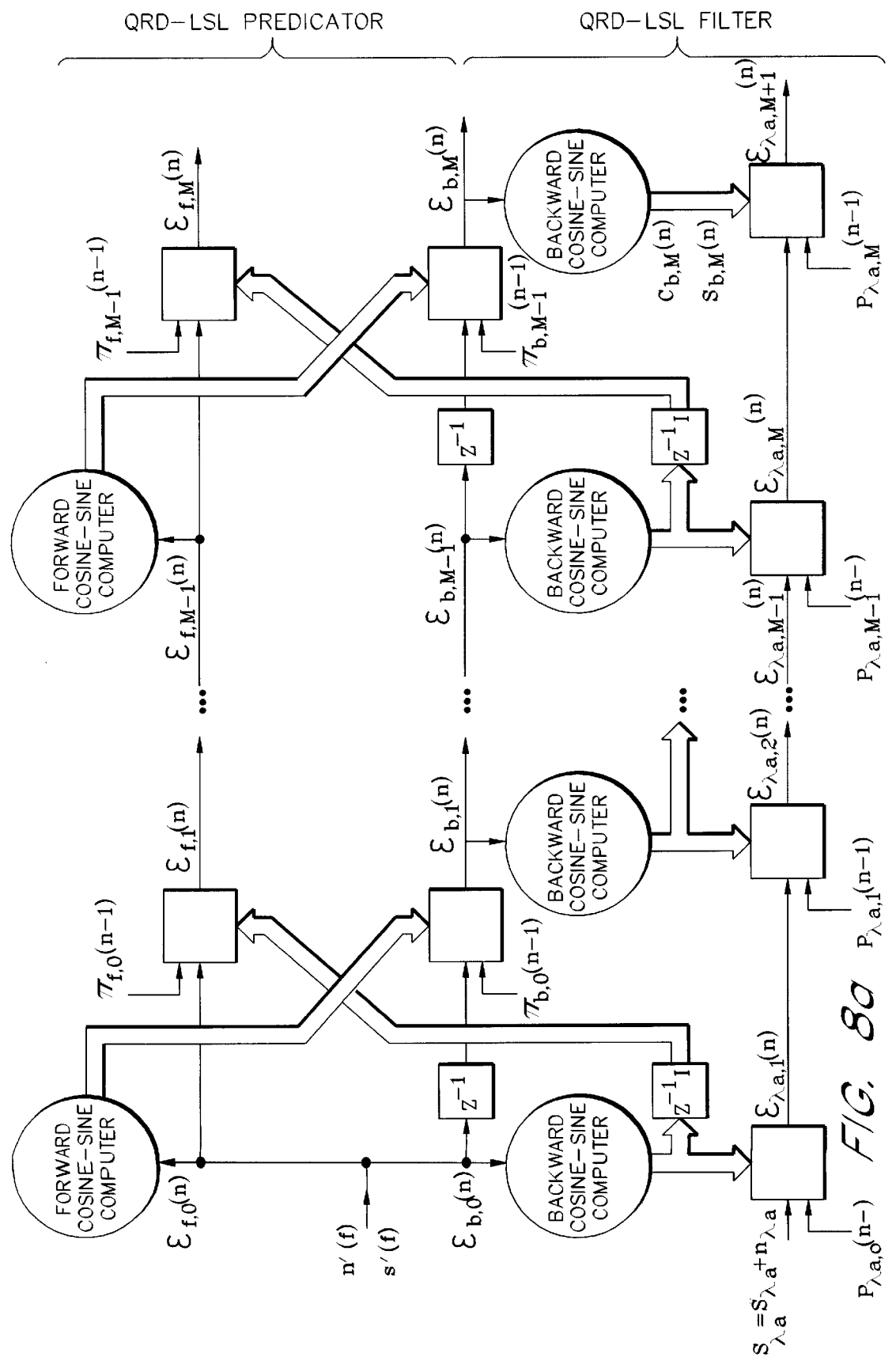
FIG. 8a is a schematic model of a joint process estimator comprising a QRD least-squares lattice (LSL) predictor and a regression filter.

In yet another embodiment, the correlation cancellation is performed with a QRD algorithm as shown diagrammatically in FIG. 8a and as described in detail in Chapter 18 of *Adaptive Filter Theory* by Simon Haykin, published by Prentice-Hall, copyright 1986.

The following equations adapted from the Haykin book correspond to the QRD-LSL diagram of FIG. 8a (also adapted from the Haykin book).

Computations a. Predictions: For time t=1, 2, . . . , and prediction order m=1, 2, . . . , M, where M is the final prediction order, compute:

$$\beta_{m-1}(t-1) = \lambda\beta_{m-1}(t-2) + |\epsilon_{b,m-1}(t-1)|^2$$

$$c_{b,m-1}(t+1) = \frac{\lambda^{1/2}\beta_{m-1}^{1/2}(t-2)}{\beta_{m-1}^{1/2}(t-1)}$$

$$s_{b,m-1}(t-1) = \frac{\epsilon_{b,m-1}^*(t-1)}{\beta_{m-1}^{1/2}(t-1)}$$

$$\epsilon_{f,m}(t) = c_{b,m-1}(t-1)\epsilon_{f,m-1}(t) - s_{b,m-1}^*(t-1)\lambda^{1/2}\pi_{f,m-1}^*(t-1)$$

$$\pi_{f,m-1}^*(t) = c_{b,m-1}(t-1)\lambda^{1/2}\pi_{f,m-1}^*(t-1) + s_{b,m-1}(t-1)\epsilon_{f,m-1}(t)$$

$$\gamma_m^{1/2}(t-1) = c_{b,m-1}(t-1)\gamma_{m-1}^{1/2}(t-1)$$

$$\mathcal{F}_{m-1}(t) = \lambda\mathcal{F}_{m-1}(t-1) + |\epsilon_{f,m-1}(t)|^2$$

$$c_{f,m-1}(t) = \frac{\lambda^{1/2}\mathcal{F}_{m-1}^{1/2}(t-1)}{\mathcal{F}_{m-1}^{1/2}(t)}$$

$$s_{f,m-1}(t) = \frac{\epsilon_{f,m-1}^*(t)}{\mathcal{F}_{m-1}^{1/2}(t)}$$

$$\epsilon_{b,m}(t) = c_{f,m-1}(t)\epsilon_{b,m-1}(t-1) - s_{f,m-1}^*(t)\lambda^{1/2}\pi_{b,m-1}^*(t-1)$$

$$\pi_{b,m-1}^*(t) = c_{f,m-1}(t)\lambda^{1/2}\pi_{b,m-1}^*(t-1) + s_{f,m-1}(t)\epsilon_{b,m-1}(t-1)$$

b. Filtering: For order m=0, 1, . . . , M−1; and time t=1, 2, . . . , compute $$\beta_m(t) = \lambda\beta_m(t-1) + |\epsilon_{b,m}(t)|^2$$

$$c_{b,m}(t) = \frac{\lambda^{1/2}\beta_m^{1/2}(t-1)}{\beta_m^{1/2}(t)}$$

$$s_{b,m}(t) = \frac{\epsilon_{b,m}^*(t)}{\beta_m^{1/2}(t)}$$

$$\epsilon_{m+1}(t) = c_{b,m}(t)\epsilon_m(t) - s_{b,m}^*(t)\lambda^{1/2}\rho_m^*(t-1)$$

$$\rho_m^*(t) = c_{b,m}(t)\lambda^{1/2}\rho_m^*(t-1) + s_{b,m}(t)\epsilon_m(t)$$

$$\gamma_{m+1}^{1/2}(t) = c_{b,m}(t)\gamma_m^{1/2}(t)$$

$$\epsilon_{m+1}(t) = \lambda_{m+1}^{1/2}(t)\epsilon_{m+1}(t)$$

5. Initialization a. Auxiliary parameter initialization: for order m=1, 2, . . . , M, set $$\pi_{f,m-1}(0)=\pi_{b,m-1}(0)=0$$

$$p_m(0)=0$$

b. Soft constraint initialization: For order m=0, 1, . . . , M, set $$\beta_m(-1)=\delta$$

$$\mathcal{F}_m(0) = \delta$$

where $\delta$ is a small positive constant.

c. Data initialization: For t=1, 2, ..., compute $$\epsilon_{f,0}(t) = \epsilon_{b,0}(t) = \mu(t)$$

$$\epsilon_0(t) = d(t)$$

$$\gamma_0(t) = 1$$

where $\mu(t)$ is the input and $d(t)$ is the desired response at time t.

FLOWCHART OF JOINT PROCESS ESTIMATOR

In a signal processor, such as a physiological monitor incorporating a reference processor of the present invention to determine a reference n'(t) or s'(t) for input to a correlation canceler, a joint process estimator 60 type adaptive noise canceler is generally implemented via a software program having an iterative loop. One iteration of the loop is analogous to a single stage of the joint process estimator as shown in FIG. 8. Thus, if a loop is iterated m times, it is equivalent to an m stage joint process estimator 60.

Figure 9:
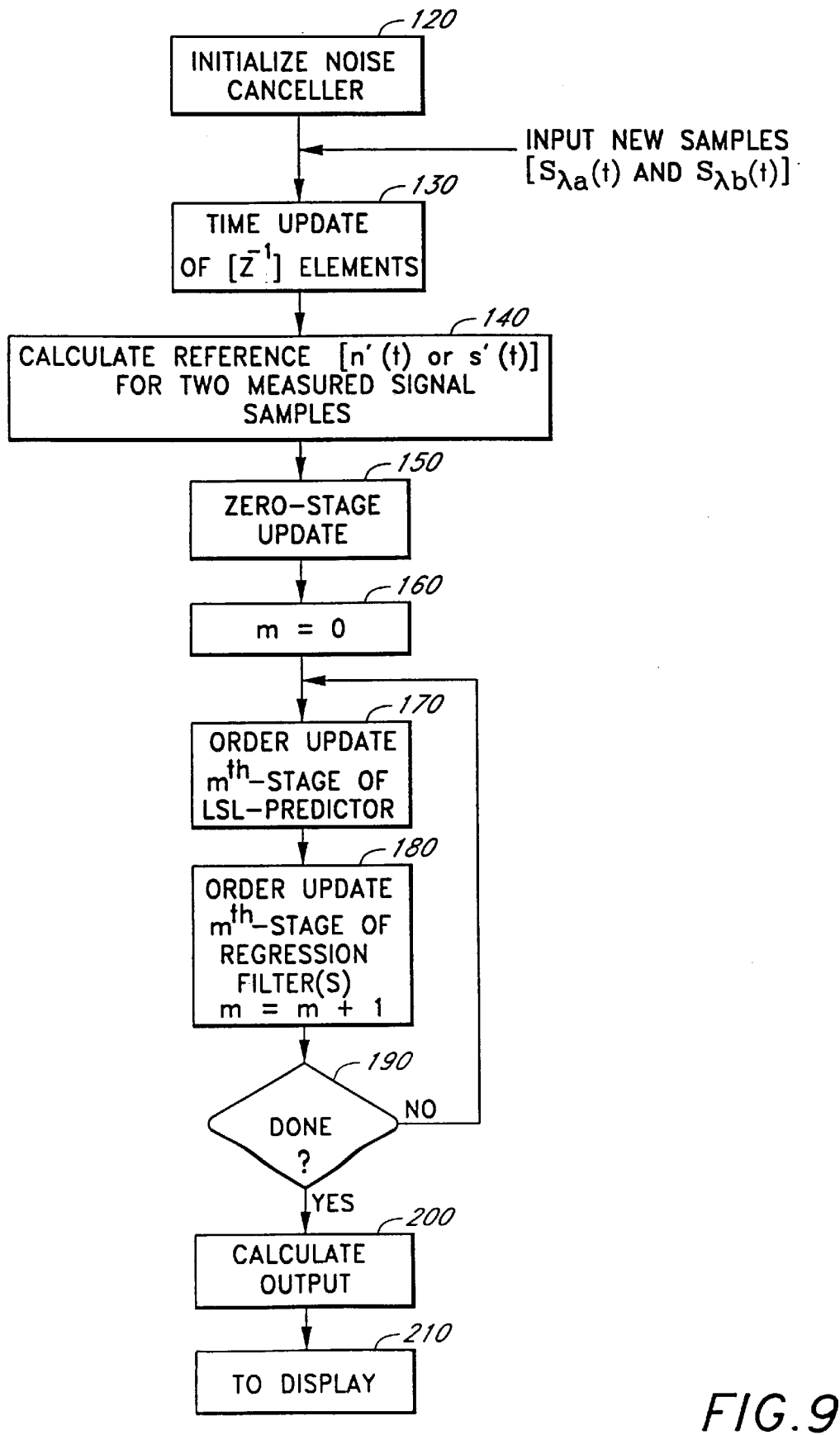
FIG. 9 is a flowchart representing a subroutine for implementing in software a joint process estimator as modeled in FIG. 8.

A flow chart of a subroutine to estimate the primary signal portion $s_{\lambda a}(t)$ or the secondary signal portion $n_{\lambda a}(t)$ of a measured composite signal, $S_{\lambda a}(t)$ is shown in FIG. 9. The flow chart illustrates the function of a reference processor for determining either the secondary reference n'(t) or the primary reference s'(t). The flowchart for the joint process estimator is implemented in software.

A one-time initialization is performed when the physiological monitor is powered-on, as indicated by an "INITIALIZE NOISE CANCELER" action block 120. The initialization sets all registers 90, 92, and 96 and delay element variables 110 to the values described above in equations (46) through (50).

Next, a set of simultaneous samples of the composite measured signals $S_{\lambda a}(t)$ and $S_{\lambda b}(t)$ is input to the subroutine represented by the flowchart in FIG. 9. Then a time update of each of the delay element program variables occurs, as indicated in a "TIME UPDATE OF [$Z^{-1}$] ELEMENTS" action block 130. The value stored in each of the delay element variables 110 is set to the value at the input of the delay element variable 110. Thus, the zero-stage backward prediction error $b_0(t)$ is stored as the first-stage delay element variable, and the first-stage backward prediction error $b_1(t)$ is stored as the second-stage delay element variable, and so on.

Then, using the set of measured signal samples $S_{\lambda a}(t)$ and $S_{\lambda b}(t)$, the reference signal is obtained using the ratiometric or the constant saturation methods described above. This is indicated by a "CALCULATE REFERENCE [n'(t) or s'(t)] FOR TWO MEASURED SIGNAL SAMPLES" action block 140.

A zero-stage order update is performed next as indicated in a "ZERO-STAGE UPDATE" action block 150. The zero-stage backward prediction error $b_0(t)$, and the zero-stage forward prediction error $f_0(t)$ are set equal to the value of the reference signal n'(t) or s'(t). Additionally, the weighted sum of the forward prediction errors $\mathfrak{I}_m(t)$ and the weighted sum of backward prediction errors $\beta_m(t)$ are set equal to the value defined in equations (47) and (48).

Next, a loop counter, m, is initialized as indicated in a "m=0" action block 160. A maximum value of m, defining the total number of stages to be used by the subroutine corresponding to the flowchart in FIG. 9, is also defined. Typically, the loop is constructed such that it stops iterating once a criterion for convergence upon a best approximation to either the primary signal or the secondary signal has been met by the joint process estimator 60. Additionally, a maximum number of loop iterations may be chosen at which the loop stops iteration. In a preferred embodiment of a physiological monitor of the present invention, a maximum number of iterations, m=6 to m=10, is advantageously chosen.

Within the loop, the forward and backward reflection coefficient $\Gamma_{f,m}(t)$ and $\Gamma_{b,m}(t)$ register 90 and 92 values in the least-squares lattice filter are calculated first, as indicated by the "ORDER UPDATE MTH CELL OF LSL-LATTICE" action block 170 in FIG. 9. This requires calculation of intermediate variable and signal values used in determining register 90, 92, and 96 values in the present stage, the next stage, and in the regression filter 80.

The calculation of regression filter register 96 value $\kappa_{m,\lambda a}(t)$ is performed next, indicated by the "ORDER UPDATE MTH STAGE OF REGRESSION FILTER(S)" action block 180. The two order update action blocks 170 and 180 are performed in sequence m times, until m has reached its predetermined maximum (in the preferred embodiment, m=6 to m=10) or a solution has been converged upon, as indicated by a YES path from a "DONE" decision block 190. In a computer subroutine, convergence is determined by checking if the weighted sums of the forward and backward prediction errors $\mathfrak{I}_m(t)$ and $\beta_m(t)$ are less than a small positive number. An output is calculated next, as indicated by a "CALCULATE OUTPUT" action block 200. The output is a good approximation to either the primary signal or secondary signal, as determined by the reference processor 26 and joint process estimator 60 subroutine corresponding to the flow chart of FIG. 9. This is displayed (or used in a calculation in another subroutine), as indicated by a "TO DISPLAY" action block 210.

A new set of samples of the two measured signals $S_{\lambda a}(t)$ and $S_{\lambda b}(t)$ is input to the processor and joint process estimator 60 adaptive noise canceler subroutine corresponding to the flowchart of FIG. 9 and the process reiterates for these samples. Note, however, that the initialization process does not re-occur. New sets of measured signal samples $S_{\lambda a}(t)$ and $S_{\lambda b}(t)$ are continuously input to the reference processor 26 and joint process estimator adaptive noise canceler subroutine. The output forms a chain of samples which is representative of a continuous wave. This waveform is a good approximation to either the primary signal waveform $s_{\lambda a}(t)$ or the secondary waveform $n_{\lambda a}(t)$ at wavelength $\lambda a$. The waveform may also be a good approximation to either the primary signal waveform $s_{\lambda b}(t)$ or the secondary waveform $n''_{\lambda b}(t)$ at wavelength $\lambda b$.

Figure 9A:
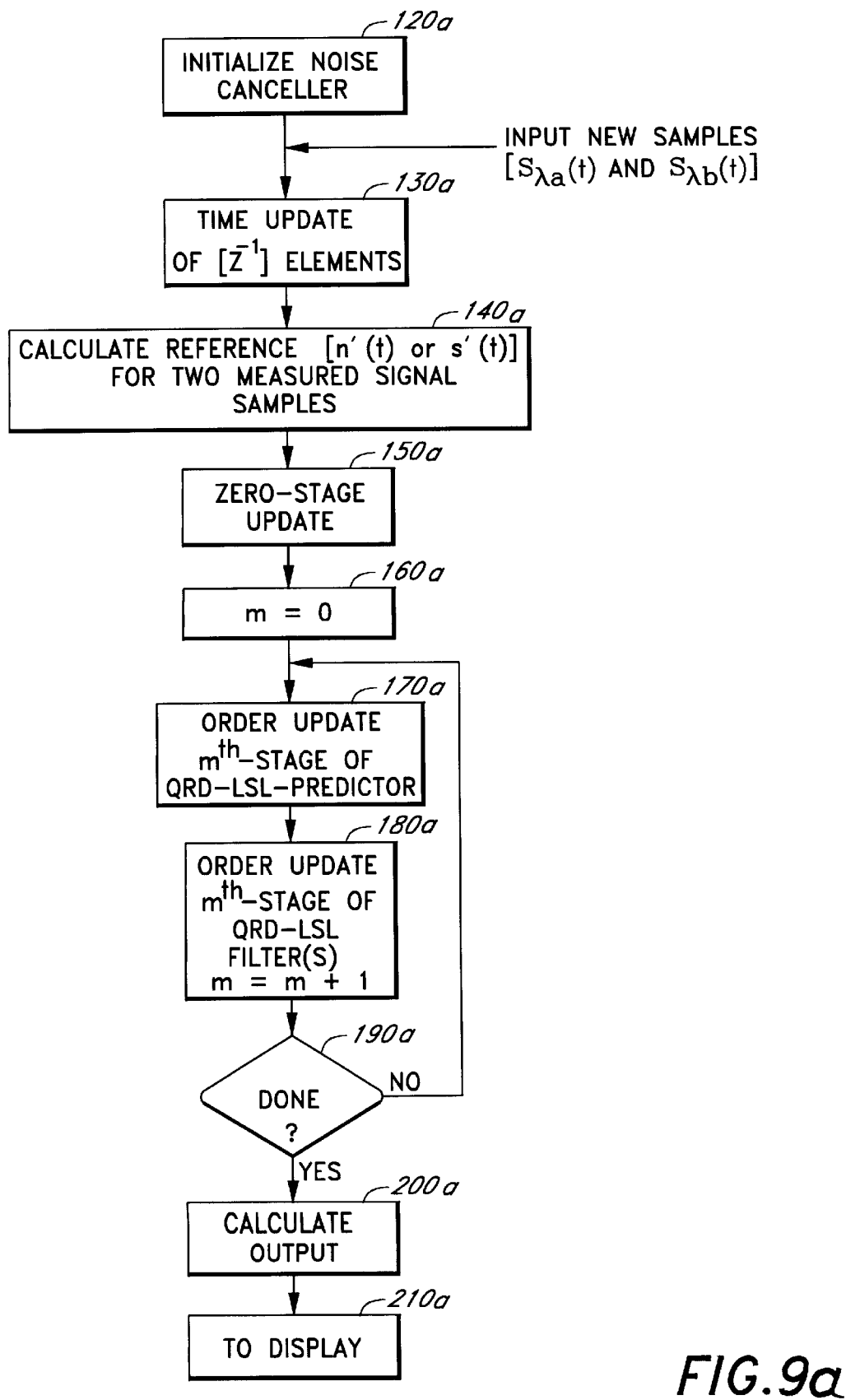

A corresponding flowchart for the QRD algorithm of FIG. 8a is depicted in FIG. 9a, with reference numeral corresponding in number with an 'a' extension

CALCULATION OF SATURATION FROM CORRELATION CANCELER OUTPUT

Physiological monitors may use the approximation of the primary signals $s''_{\lambda a}(t)$ or $s''_{\lambda b}(t)$ or the secondary signals $n''_{\lambda a}(t)$ or $n''_{\lambda b}(t)$ to calculate another quantity, such as the saturation of one constituent in a volume containing that constituent plus one or more other constituents. Generally, such calculations require information about either a primary or secondary signal at two wavelengths. For example, the constant saturation method requires a good approximation of the primary signal portions $s_{\lambda a}(t)$ and $s_{\lambda b}(t)$ of both measured signals $S_{\lambda a}(t)$ and $S_{\lambda b}(t)$. The arterial saturation is determined from the approximations to both signals, i.e. $s''_{\lambda a}(t)$ and $s''_{\lambda b}(t)$. The constant saturation method also requires a good approximation of the secondary signal portions $n_{\lambda a}(t)$ or $n_{\lambda b}(t)$. An estimate of the venous saturation may be determined from the approximations to these signals i. e. $n''_{\lambda a}(t)$ and $n''_{\lambda b}(t)$.

Figure 10:
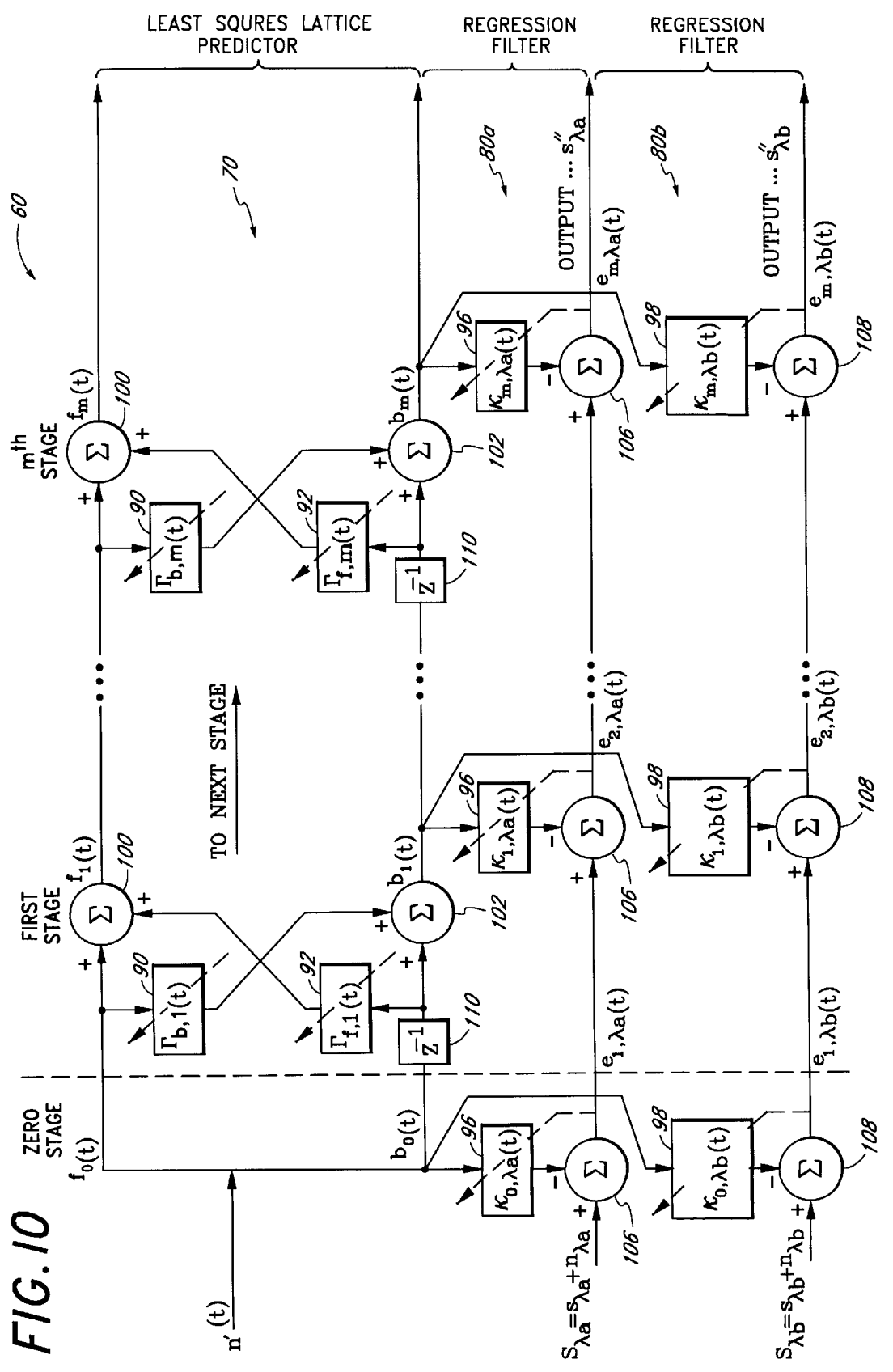

A joint process estimator 60 having two regression filters 80a and 80b is shown in FIG. 10. A first regression filter 80a accepts a measured signal $S_{\lambda a}(t)$. A second regression filter 80b accepts a measured signal $S_{\lambda b}(t)$ for a use of the constant saturation method to determine the reference signal n'(t) or s'(t). The first and second regression filters 80a and 80b are independent. The backward prediction error $b_m(t)$ is input to each regression filter 80a and 80b, the input for the second regression filter 80b bypassing the first regression filter 80a.

The second regression filter 80b comprises registers 98, and summing elements 108 arranged similarly to those in the first regression filter 80a. The second regression filter 80b operates via an additional intermediate variable in conjunction with those defined by equations (54) through (64), i.e.:

$$\rho_{m,\lambda b}(t) = \lambda \rho_{m,\lambda b}(t-1) + \{b_m(t)e^*_{m,\lambda b}(t)/\gamma_m(t)\}; \text{ and} \tag{65}$$

$$\rho_{0,\lambda b}(0) = 0. \tag{66}$$

The second regression filter 80b has; an error signal value defined similar to the first regression filter error signal values, $e_{m+1,\lambda a}(t)$, i.e.:

$$e_{m+1,\lambda b}(t) = e_{m,\lambda b}(t) - \kappa K^*_{m,\lambda b}(t) b_m(t); \text{ and} \tag{67}$$

$$e_{0,\lambda b}(t) = S_{\lambda b}(t) \text{ for } t \geq 0. \tag{68}$$

The second regression filter has a regression coefficient $\kappa_{m,\lambda b}(t)$ register 98 value defined similarly to the first regression filter error signal values, i.e.:

$$\kappa_{m,\lambda b}(t) = \{\rho_{m,\lambda b}(t)/\beta_m(t)\}; \text{ or} \tag{69}$$

These values are used in conjunction with those intermediate variable values, signal values, register and register values defined in equations (46) through (64). These signals are calculated in an order defined by placing the additional signals immediately adjacent a similar signal for the wavelength $\lambda a$.

For the constant saturation method, $S_{\lambda b}(t)$ is input to the second regression filter 80b. The output is then a good approximation to the primary signal $s''_{\lambda b}(t)$ or secondary signal $s''_{\lambda b}(t)$.

The addition of the second regression filter 80b does not substantially change the computer program subroutine represented by the flowchart of FIG. 9. Instead of an order update of the $m^{th}$ stage of only one regression filter, an order update of the $m^{th}$ stage of both regression filters 80a and 80b is performed. This is characterized by the plural designation in the "ORDER UPDATE OF $m^{th}$ STAGE OF REGRESSION FILTER(S)" activity block 180 in FIG. 9. Since the regression filters 80a and 80b operate independently, independent calculations can be performed in the reference processor and joint process estimator 60 adaptive noise canceler subroutine modeled by the flowchart of FIG. 9.

Figure 10A:
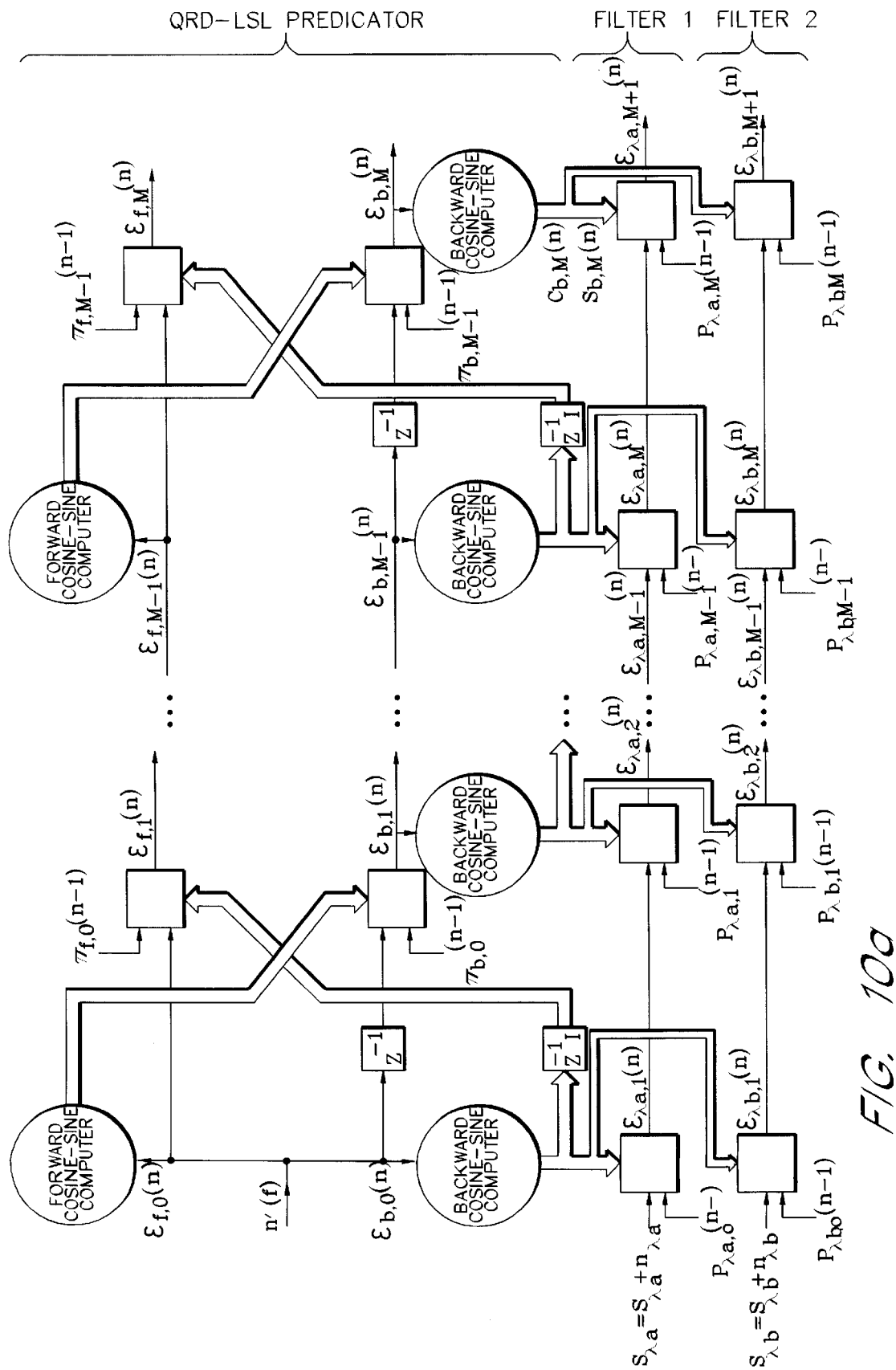
FIG. 10a is a schematic model of a joint process estimator with a QRD least-squares lattice predictor and two regression filters.

An alternative diagram for the joint process estimator of FIG. 10, using the QRD algorithm and having two regression filters is shown in FIG. 10a. This type of joint process estimator would be used for correlation cancellation using the QRD algorithm described in the Haykin book.

CALCULATION OF SATURATION

Once good approximations to the primary signal portions $s''_{\lambda a}(t)$ and $s''_{\lambda b}(t)$ or the secondary signal portion, $n''_{\lambda a}(t)$ and $n''_{\lambda b}(t)$, have been determined by the joint process estimator 60, the saturation of $A_5$ in a volume containing $A_5$ and $A_6$, for example, may be calculated according to various known methods. Mathematically, the approximations to the primary signals can be written in terms of $\lambda a$ and $\lambda b$, as:

$$s''_{\lambda a}(t) \approx \epsilon_{5,\lambda a} c_5 x_{5,6}(t) + \epsilon_{6,\lambda a} c_6 x_{5,6}(t); \text{ and} \tag{70}$$

$$s''_{\lambda b}(t) \approx \epsilon_{5,\lambda b} c_5 x_{5,6}(t) + \epsilon_{6,\lambda b} c_6 x_{5,6}(t). \tag{71}$$

Equations (70) and (71) are equivalent to two equations having three unknowns, namely $c_5(t)$, $c_6(t)$ and $x_{5,6}(t)$. The saturation can be determined by acquiring approximations to the primary or secondary signal portions at two different, yet proximate times $t_1$ and $t_2$ over which the saturation of $A_5$ in the volume containing $A_5$ and $A_6$ and the saturation of $A_3$ in the volume containing $A_3$ and $A_4$ does not change substantially. For example, for the primary signals estimated at times $t_1$ and $t_2$:

$$s''_{\lambda a}(t_1) \approx \epsilon_{5,\lambda a} c_5 x_{5,6}(t_1) + \epsilon_{6,\lambda a} c_6 x_{5,6}(t_1) \tag{72}$$

$$s''_{\lambda b}(t_1) \approx \epsilon_{5,\lambda b} c_5 x_{5,6}(t_1) + \epsilon_{6,\lambda b} c_6 x_{5,6}(t_1) \tag{73}$$

$$s''_{\lambda a}(t_2) \approx \epsilon_{5,\lambda a} c_5 x_{5,6}(t_2) + \epsilon_{6,\lambda a} c_6 x_{5,6}(t_2) \tag{74}$$

$$s''_{\lambda b}(t_2) \approx \epsilon_{5,\lambda b} c_5 x_{5,6}(t_2) + \epsilon_{6,\lambda b} c_6 x_{5,6}(t_2) \tag{75}$$

Then, difference signals may be determined which relate the signals of equations (72) through (75), i.e.:

$$\Delta s_{\lambda a} = s''_{\lambda a}(t_1) - s''_{\lambda a}(t_2) \approx \epsilon_{5,\lambda a} c_5 \Delta x + \epsilon_{6,\lambda a} c_6 \Delta x; \text{ and} \tag{76}$$

$$\Delta s_{\lambda b} = s''_{\lambda b}(t_1) - s''_{\lambda b}(t_2) \approx \epsilon_{5,\lambda b} c_5 \Delta x + \epsilon_{6,\lambda b} c_6 \Delta x; \tag{77}$$

where $\Delta x = x_{5,6}(t_1) - x_{5,6}(t_2)$. The average saturation at time $t = (t_1 + t_2)/2$ is:

$$\text{Saturation }(t) = c_5(t)/[c_5(t) + c_6(t)] \tag{78}$$

$$= \frac{\epsilon_{6,\lambda a} - \epsilon_{6,\lambda b}(\Delta s_{\lambda a}/\Delta s_{\lambda b})}{\epsilon_{6,\lambda a} - \epsilon_{5,\lambda a} - (\epsilon_{6,\lambda b} - \epsilon_{5,\lambda b})(\Delta s_{\lambda a}/\Delta s_{\lambda b})} \tag{79}$$

It will be understood that the $\Delta x$ term drops out from the saturation calculation because of the division. Thus, knowledge of the thickness of the primary constituents is not required to calculate saturation.

PULSE OXIMETRY MEASUREMENTS

A specific example of a physiological monitor utilizing a processor of the present invention to determine a secondary reference n'(t) for input to a correlation canceler that removes erratic motion-induced secondary signal portions is a pulse oximeter. Pulse oximetry may also be performed utilizing a processor of the present invention to determine a primary signal reference s'(t) which may be used for display purposes or for input to a correlation canceler to derive information about patient movement and venous blood oxygen saturation.

A pulse oximeter typically causes energy to propagate through a medium where blood flows close to the surface for example, an ear lobe, or a digit such as a finger, a forehead or a fetus' scalp. An attenuated signal is measured after propagation through or reflected from the medium. The pulse oximeter estimates the saturation of oxygenated blood.

Freshly oxygenated blood is pumped at high pressure from the heart into the arteries for use by the body. The volume of blood in the arteries varies with the heartbeat, giving rise to a variation in absorption of energy at the rate of the heartbeat, or the pulse.

Oxygen depleted, or deoxygenated, blood is returned to the heart by the veins along with unused oxygenated blood. The volume of blood in the veins varies with the rate of breathing, which is typically much slower than the heartbeat. Thus, when there is no motion induced variation in the thickness of the veins, venous blood causes a low frequency variation in absorption of energy. When there is motion induced variation in the thickness of the veins, the low frequency variation in absorption is coupled with the erratic variation in absorption due to motion artifact.

In absorption measurements using the transmission of energy through a medium, two light emitting diodes (LED's) are positioned on one side of a portion of the body where blood flows close to the surface, such as a finger, and a photodetector is positioned on the opposite side of the finger. Typically, in pulse oximetry measurements, one LED emits a visible wavelength, preferably red, and the other LED emits an infrared wavelength. However, one skilled in the art will realize that other wavelength combinations could be used. The finger comprises skin, tissue, muscle, both arterial blood and venous blood, fat, etc., each of which absorbs light energy differently due to different absorption coefficients, different concentrations, different thicknesses, and changing optical pathlengths. When the patient is not moving, absorption is substantially constant except for the flow of blood. The constant attenuation can be determined and subtracted from the signal via traditional filtering techniques. When the patient moves, this causes perturbation such as changing optical pathlength due to movement of background fluids (e.g., venous blood having a different saturation than the arterial blood). Therefore, the measured signal becomes erratic. Erratic motion induced noise typically cannot be predetermined and/or subtracted from the measured signal via traditional filtering techniques. Thus, determining the oxygen saturation of arterial blood and venous blood becomes more difficult.

Figure 11:
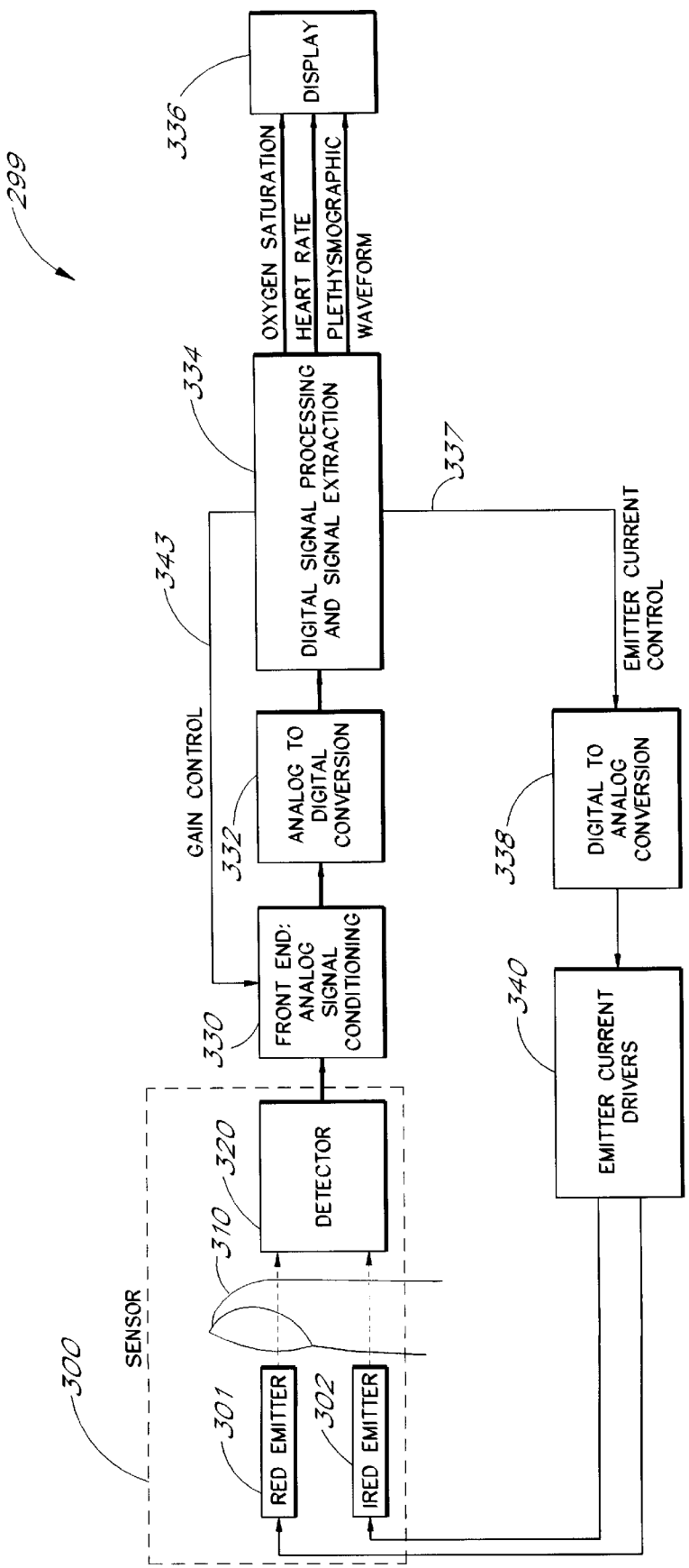
FIG. 11 is an example of a physiological monitor in accordance with the teachings of one aspect of the present invention.
Figure 12:
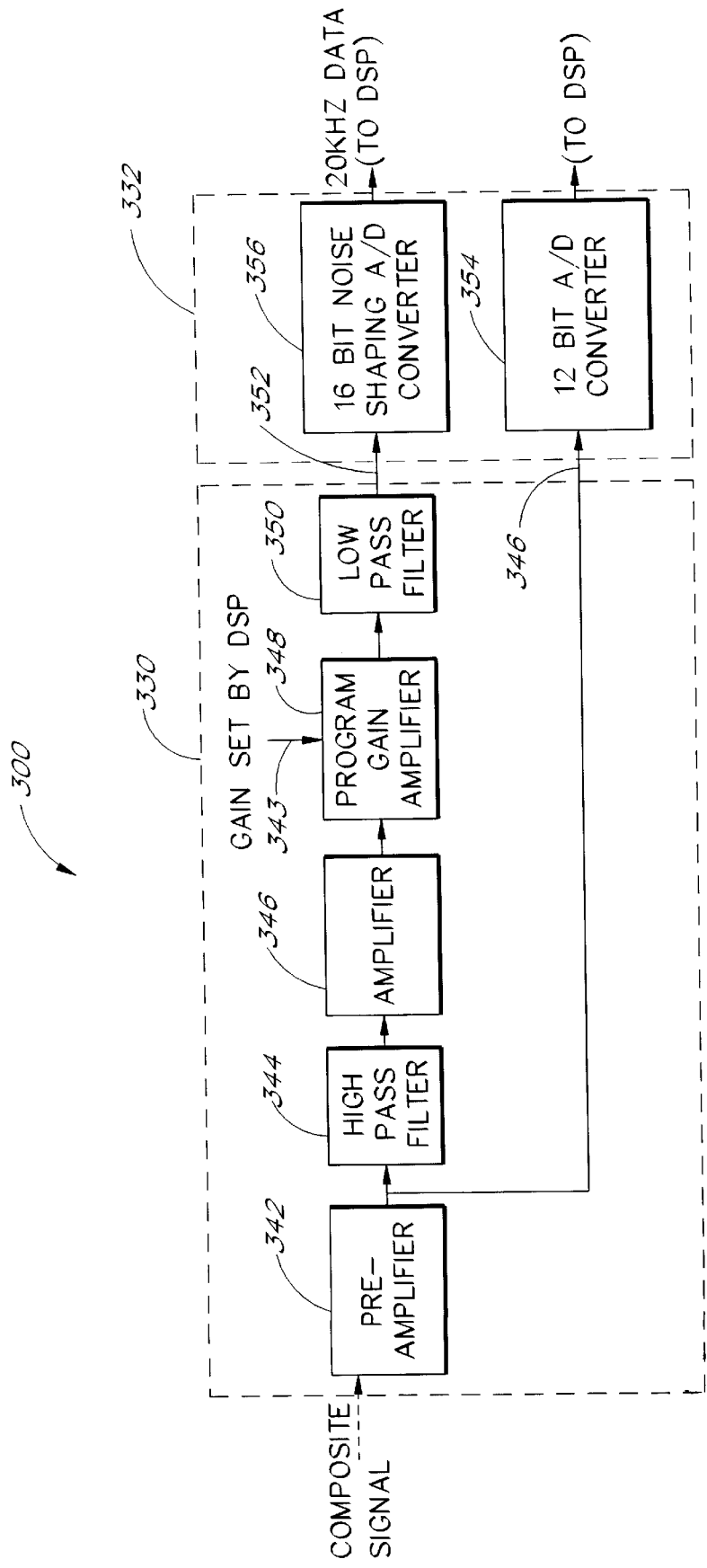
FIG. 12 illustrates the front end analog signal conditioning circuitry and the analog to digital conversion circuitry of the physiological monitor of FIG. 11.
Figure 13:
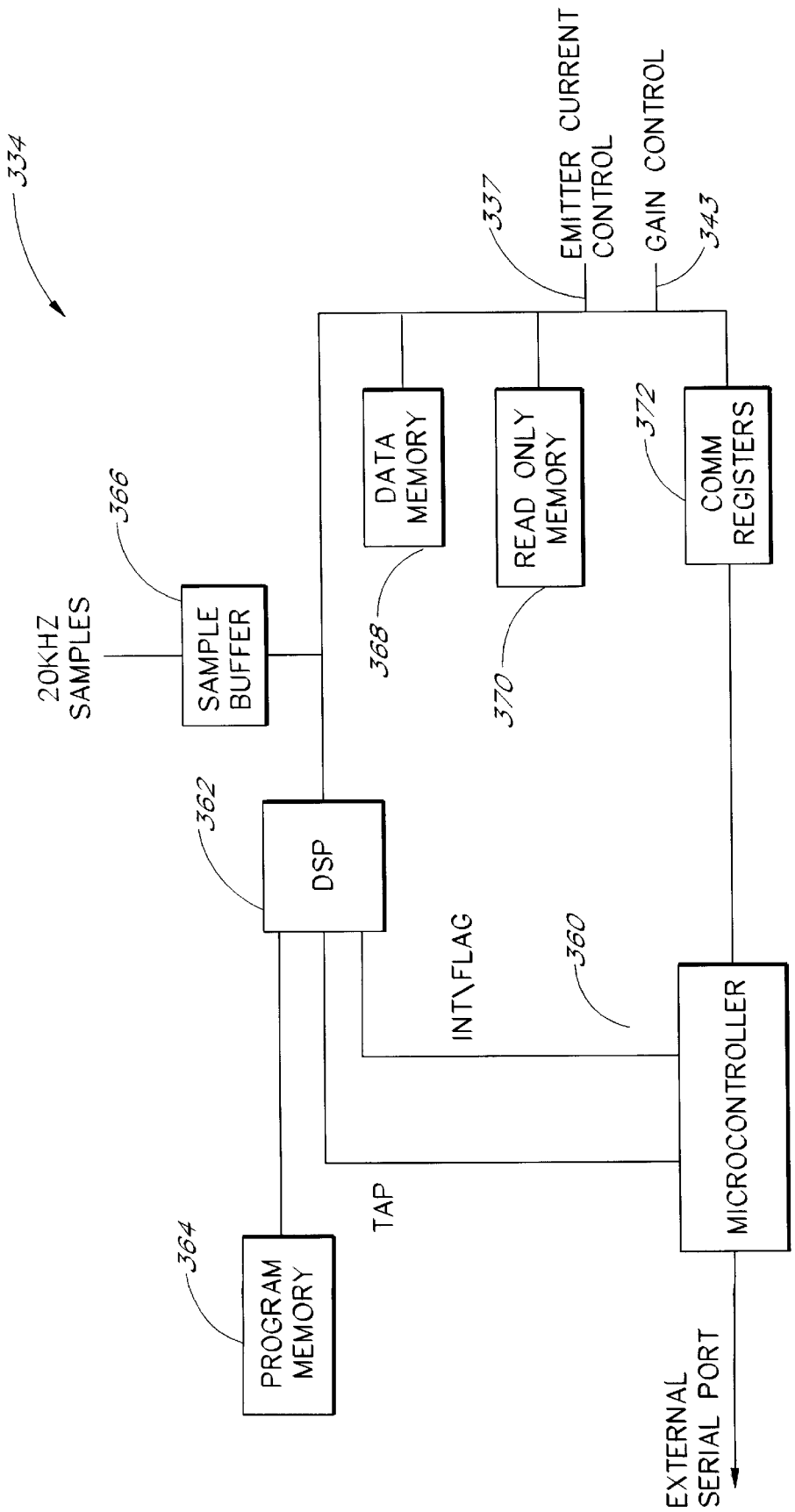
FIG. 13 illustrates further detail of the digital signal processing circuitry of FIG. 11.

A schematic of a physiological monitor for pulse oximetry is shown in FIGS. 11–13. FIG. 11 depicts a general hardware block diagram of a pulse oximeter 299. A sensor 300 has two light emitters 301 and 302 such as LED's. One LED 301 emitting light of red wavelengths and another LED 302 emitting light of infrared wavelengths are placed adjacent a finger 310. A photodetector 320, which produces an electrical signal corresponding to the attenuated visible and infrared light energy signals is located opposite the LED's 301 and 302. The photodetector 320 is connected to front end analog signal conditioning circuitry 330.

The front end analog signal conditioning circuitry 330 has outputs coupled to analog to digital conversion circuit 332. The analog to digital conversion circuitry 332 has outputs coupled to a digital signal processing system 334. The digital signal processing system 334 provides the desired parameters as outputs for a display 336. Outputs for display are, for example, blood oxygen saturation, heart rate, and a clean plethysmographic waveform.

The signal processing system also provides an emitter current control output 337 to a digital-to-analog converter circuit 338 which provides control information for light emitter drivers 340. The light emitter drivers 340 couple to the light emitters 301, 302. The digital signal processing system 334 also provides a gain control output 342 for the front end analog signal conditioning circuitry 330.

Figure 11A:
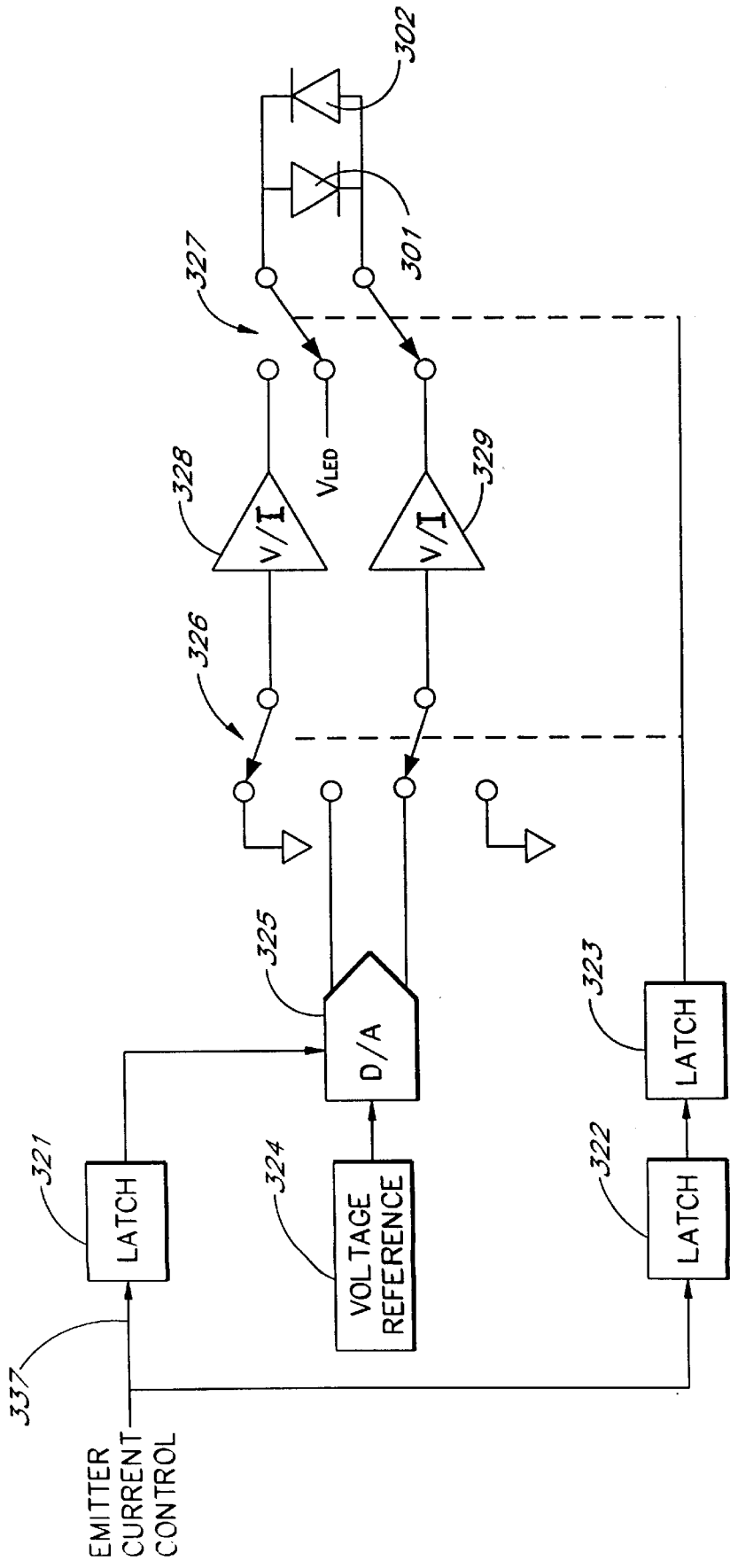
FIG. 11a illustrates an example of a low noise emitter current driver with accompanying digital to analog converter.

FIG. 11a illustrates a preferred embodiment for the combination of the emitter drivers 340 and the digital to analog conversion circuit 338. As depicted in FIG. 11a, the driver comprises first and second input latches 321, 322, a synchronizing latch 323, a voltage reference 324, a digital to analog conversion circuit 325, first and second switch banks 326, 327, first and second voltage to current converters 328, 329 and the LED emitters 301, 302 corresponding to the LED emitters 301, 302 of FIG. 11.

The preferred driver depicted in FIG. 11a is advantageous in that the present inventors recognized that much of the noise in the oximeter 299 of FIG. 11 is caused by the LED emitters 301, 302. Therefore, the emitter driver circuit of FIG. 11a is designed to minimize the noise from the emitters 301, 302. The first and second input latches 321, 324 are connected directly to the DSP bus. Therefore, these latches significantly minimizes the bandwidth (resulting in noise) present on the DSP bus which passes through to the driver circuitry of FIG. 11a. The output of the first and second input latches only changes when these latched detect their address on the DSP bus. The first input latch receives the setting for the digital to analog converter circuit 325. The second input latch receives switching control data for the switch banks 326, 327. The synchronizing latch accepts the synchronizing pulses which maintain synchronization between the activation of emitters 301, 302 and the analog to digital conversion circuit 332.

The voltage reference is also chosen as a low noise DC voltage reference for the digital to analog conversion circuit 325. In addition, in the present embodiment, the voltage reference has an lowpass output filter with a very low corner frequency (e.g., 1 Hz in the present embodiment). The digital to analog converter 325 also has a lowpass filter at its output with a very low corner frequency (e.g., 1 Hz). The digital to analog converter provides signals for each of the emitters 301, 302.

In the present embodiment, the output of the voltage to current converters 328, 329 are switched such that with the emitters 301, 302 connected in back-to-back configuration, only one emitter is active an any given time. In addition, the voltage to current converter for the inactive emitter is switched off at its input as well, such that it is completely deactivated. This reduces noise from the switching and voltage to current conversion circuitry. In the present embodiment, low noise voltage to current converters are selected (e.g., Op 27 Op Amps), and the feedback loop is configured to have a low pass filter to reduce noise. In the present embodiment, the low pass filtering function of the voltage to current converter 328, 329 has a corner frequency of just above 625 Hz, which is the switching speed for the emitters, as further discussed below. Accordingly, the preferred driver circuit of FIG. 11a, minimizes the noise of the emitters 301, 302.

In general, the red and infrared light emitters 301, 302 each emits energy which is absorbed by the finger 310 and received by the photodetector 320. The photodetector 320 produces an electrical signal which corresponds to the intensity of the light energy striking the photodetector 320. The front end analog signal conditioning circuitry 330 receives the intensity signals and filters and conditions these signals as further described below for further processing. The resultant signals are provided to the analog-to-digital conversion circuitry 332 which converts the analog signals to digital signals for further processing by the digital signal processing system 334. The digital signal processing system 334 utilizes the two signals in order to provide a what will be called herein a "saturation transform." It should be understood, that for parameters other than blood saturation monitoring, the saturation transform could be better termed as a concentration transform, in-vivo transform, or the like, depending on the desired parameter. The term saturation transform is used to describe an operation which converts the sample data from time domain to saturation domain values as will be apparent from the discussion below. In the present embodiment, the output of the digital signal processing system 334 provides clean plethysmographic waveforms of the detected signals and provides values for oxygen saturation and pulse rate to the display 336.

It should be understood that in different embodiments of the present invention, one or more of the outputs may be provided. The digital signal processing system 334 also provides control for driving the light emitters 301, 302 with an emitter current control signal on the emitter current control output 337. This value is a digital value which is converted by the digital-to-analog conversion circuit 338 which provides a control signal to the emitter current drivers 340. The emitter current drivers 340 provide the appropriate current drive for the red emitter 301 and the infrared emitter 302. Further detail of the operation of the physiological monitor for pulse oximetry is explained below.

In the present embodiment, the light emitters are driven via the emitter current driver 340 to provide light transmission with digital modulation at 625 Hz. In the present embodiment, the light emitters 301, 302 are driven at a power level which provides an acceptable intensity for detection by the detector and for conditioning by the front end analog signal conditioning circuitry 330. Once this energy level is determined for a given patient by the digital signal processing system 334, the current level for the red and infrared emitters is maintained constant. It should be understood, however, that the current could be adjusted for changes in the ambient room light and other changes which would effect the voltage input to the front end analog signal conditioning circuitry 330. In the present invention, the red and infrared light emitters are modulated as follows: for one complete 625 Hz red cycle, the red emitter 301 is activated for the first quarter cycle, and off for the remaining three-quarters cycle; for one complete 625 Hz infrared cycle, the infrared light emitter 302 is activated for one quarter cycle and is off for the remaining three-quarters cycle. In order to only receive one signal at a time, the emitters are cycled on and off alternatively, in sequence, with each only active for a quarter cycle per 625 Hz cycle and a quarter cycle separating the active times.

The light signal is attenuated (amplitude modulated) by the pumping of blood through the finger 310 (or other sample medium). The attenuated (amplitude modulated) signal is detected by the photodetector 320 at the 625 Hz carrier frequency for the red and infrared light. Because only a single photodetector is used, the photodetector 320 receives both the red and infrared signals to form a composite time division signal.

The composite time division signal is provided to the front analog signal conditioning circuitry 330. Additional detail regarding the front end analog signal conditioning circuitry 330 and the analog to digital converter circuit 332 is illustrated in FIG. 12. As depicted in FIG. 12, the front end circuitry 302 has a preamplifier 342, a high pass filter 344, an amplifier 346, a programmable gain amplifier 348, and a low pass filter 350. The preamplifier 342 is a transimpedance amplifier that converts the composite current signal from the photodetector 320 to a corresponding voltage signal, and amplifies the signal. In the present embodiment, the preamplifier has a predetermined gain to boost the signal amplitude for ease of processing. In the present embodiment, the source voltages for the preamplifier 342 are −15 VDC and +15 VDC. As will be understood, the attenuated signal contains a component representing ambient light as well as the component representing the infrared or the red light as the case may be in time. If there is light in the vicinity of the sensor 300 other than the red and infrared light, this ambient light is detected by the photodetector 320. Accordingly, the gain of the preamplifier is selected in order to prevent the ambient light in the signal from saturating the preamplifier under normal and reasonable operating conditions.

In the present embodiment, the preamplifier 342 comprises an Analog Devices AD743JR OpAmp. This transimpedance amplifier is particularly advantageous in that it exhibits several desired features for the system described, such as: low equivalent input voltage noise, low equivalent input current noise, low input bias current, high gain bandwidth product, low total harmonic distortion, high common mode rejection, high open loop gain, and a high power supply rejection ratio.

The output of the preamplifier 342 couples as an input to the high pass filter 344. The output of the preamplifier also provides a first input 346 to the analog to digital conversion circuit 332. In the present embodiment, the high pass filter is a single-pole filter with a corner frequency of about ½–1 Hz. However, the corner frequency is readily raised to about 90 Hz in one embodiment. As will be understood, the 625 Hz carrier frequency of the red and infrared signals is well above a 90 Hz corner frequency. The high-pass filter 344 has an output coupled as an input to an amplifier 346. In the present embodiment, the amplifier 346 comprises a unity gain amplifier. However, the gain of the amplifier 346 is adjustable by the variation of a single resistor. The gain of the amplifier 346 would be increased if the gain of the preamplifier 342 is decreased to compensate for the effects of ambient light.

The output of the amplifier 346 provides an input to a programmable gain amplifier 348. The programmable gain amplifier 348 also accepts a programming input from the digital signal processing system 334 on a gain control signal line 343. The gain of the programmable gain amplifier 348 is digitally programmable. The gain is adjusted dynamically at initialization or sensor placement for changes in the medium under test from patient to patient. For example, the signal from different fingers differs somewhat. Therefore, a dynamically adjustable amplifier is provided by the programmable gain amplifier 348 in order to obtain a signal suitable for processing.

The programmable gain amplifier is also advantageous in an alternative embodiment in which the emitter drive current is held constant. In the present embodiment, the emitter drive current is adjusted for each patient in order to obtain the proper dynamic range at the input of the analog to digital conversion circuit 332. However, changing the emitter drive current can alter the emitter wavelength, which in turn affects the end result in oximetry calculations. Accordingly, it would be advantageous to fix the emitter drive current for all patients. In an alternative embodiment of the present invention, the programmable gain amplifier can be adjusted by the DSP in order to obtain a signal at the input to the analog to digital conversion circuit which is properly within the dynamic range (+3v to −3v in the present embodiment) of the analog to digital conversion circuit 332. In this manner, the emitter drive current could be fixed for all patients, eliminating the wavelength shift due to emitter current drive changes.

The output of the programmable gain amplifier 348 couples as an input to a low-pass filter 350. Advantageously, the low pass filter 350 is a single-pole filter with a corner frequency of approximately 10 Khz in the present embodiment. This low pass filter provides anti-aliasing in the present embodiment.

The output of the low-pass filter 350 provides a second input 352 to the analog-to-digital conversion circuit 332. FIG. 12 also depicts additional defect of the analog-to-digital conversion circuit. In the present embodiment, the analog-to-digital conversion circuit 332 comprises a first analog-to-digital converter 354 and a second analog-to-digital converter 356. Advantageously, the first analog-to-digital converter 354 accepts input from the first input 346 to the analog-to-digital conversion circuit 332, and the second analog to digital converter 356 accepts input on the second input 352 to the analog-to-digital conversion circuitry 332.

In one advantageous embodiment, the first analog-to-digital converter 354 is a diagnostic analog-to-digital converter. The diagnostic task (performed by the digital signal processing system) is to read the output of the detector as amplified by the preamplifier 342 in order to determine if the signal is saturating the input to the high-pass filter 344. In the present embodiment, if the input to the high pass filter 344 becomes saturated, the front end analog signal conditioning circuits 330 provides a '0' output. Alternatively, the first analog-to-digital converter 354 remains unused.

The second analog-to-digital converter 352 accepts the conditioned composite analog signal from the front end signal conditioning circuitry 330 and converts the signal to digital form. In the present embodiment, the second analog to digital converter 356 comprises a single-channel, delta-sigma converter. In the present embodiment, a Crystal Semiconductor CS5317-KS delta-sigma analog to digital converter is used. Such a converter is advantageous in that it is low cost, and exhibits low noise characteristics. More specifically, a delta-sigma converter consists of two major portions, a noise modulator and a decimation filter. The selected converter uses a second order analog delta-sigma modulator to provide noise shaping. Noise shaping refers to changing the noise spectrum from a flat response to a response where noise at the lower frequencies has been reduced by increasing noise at higher frequencies. The decimation filter then cuts out the reshaped, higher frequency noise to provide 16-bit performance at a lower frequency. The present converter samples the data 128 times for every 16 bit data word that it produces. In this manner, the converter provides excellent noise rejection, dynamic range and low harmonic distortion, that help in critical measurement situations like low perfusion and electrocautery.

In addition, by using a single-channel converter, there is no need to tune two or more channels to each other. The delta-sigma converter is also advantageous in that it exhibits noise shaping, for improved noise control. An exemplary analog to digital converter is a Crystal Semiconductor CS5317. In the present embodiment, the second analog to digital converter 356 samples the signal at a 20 Khz sample rate. The output of the second analog to digital converter 356 provides data samples at 20 Khz to the digital signal processing system 334 (FIG. 11).

The digital signal processing system 334 is illustrated in additional detail in FIG. 13. In the present embodiment, the digital signal processing system comprises a microcontroller 360, a digital signal processor 362, a program memory 364, a sample buffer 366, a data memory 368, a read only memory 370 and communication registers 372. In the present embodiment, the digital signal processor 362 is an Analog Devices AD 21020. In the present embodiment, the microcontroller 360 comprises a Motorola 68HC05, with built in program memory. In the present embodiment, the sample buffer 366 is a buffer which accepts the 20 Khz sample data from the analog to digital conversion circuit 332 for storage in the data memory 368. In the present embodiment, the data memory 368 comprises 32 KWords (words being 40 bits in the present embodiment) of static random access memory.

The microcontroller 360 is connected to the DSP 362 via a conventional JTAG Tap line. The microcontroller 360 transmits the boot loader for the DSP 362 to the program memory 364 via the Tap line, and then allows the DSP 362 to boot from the program memory 364. The boot loader in program memory 364 then causes the transfer of the operating instructions for the DSP 362 from the read only memory 370 to the program memory 364. Advantageously, the program memory 364 is a very high speed memory for the DSP 362.

The microcontroller 360 provides the emitter current control and gain control signals via the communications register 372.

Figure 14:
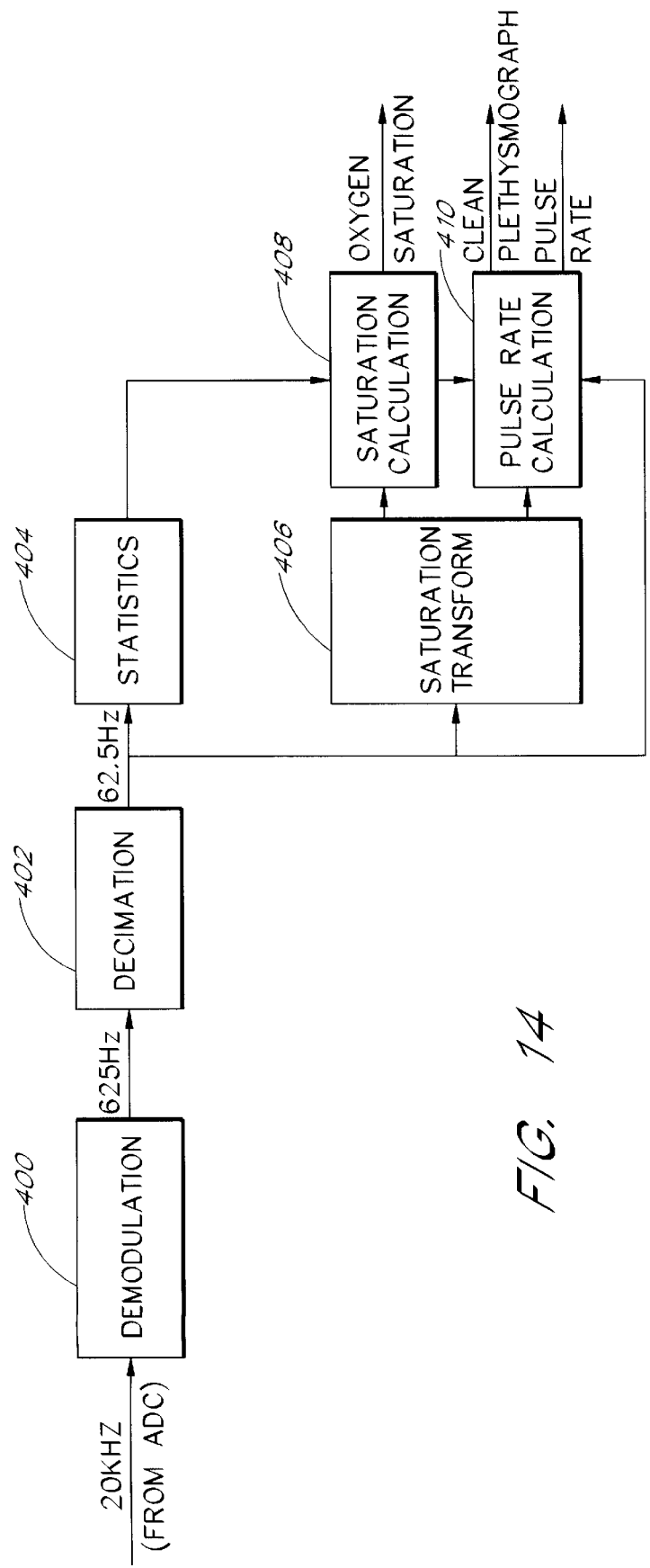
FIG. 14 illustrates additional detail of the operations performed by the digital signal processing circuitry of FIG. 11.

FIGS. 14–20 depict functional block diagrams of the operations of the pulse oximeter 299 carried out by the digital signal processing system 334. The signal processing functions described below are carried out by the DSP 362 in the present embodiment with the microcontroller 360 providing system management. In the present embodiment, the operation is software/firmware controlled. FIG. 14 depicts a generalized functional block diagram for the operations performed on the 20 Khz sample data entering the digital signal processing system 334. As illustrated in FIG. 14, a demodulation, as represented in a demodulation module 400, is first performed. Decimation, as represented in a decimation module 402 is then performed on the resulting data. Certain statistics are calculated, as represented in a statistics module 404 and a saturation transform is performed, as represented in a saturation transform module 406, on the data resulting from the decimation operation. The data subjected to the statistics operations and the data subjected to the saturation transform operations are forwarded to saturation operations, as represented by a saturation calculation module 408 and pulse rate operations, as represented in a pulse rate calculation module 410.

In general, the demodulation operation separates the red and infrared signals from the composite signal and removes the 625 Hz carrier frequency, leaving raw data points. The raw data points are provided at 625 Hz intervals to the decimation operation which reduces the samples by an order of 10 to samples at 62.5 Hz. The decimation operation also provides some filtering on the samples. The resulting data is subjected to statistics and to the saturation transform operations in order to calculate a saturation value which is very tolerant to motion artifacts and other noise in the signal. The saturation value is ascertained in the saturation calculation module 408, and a pulse rate and a clean plethysmographic waveform is obtained through the pulse rate module 410. Additional detail regarding the various operations is provided in connection with FIGS. 15–21.

Figure 15:
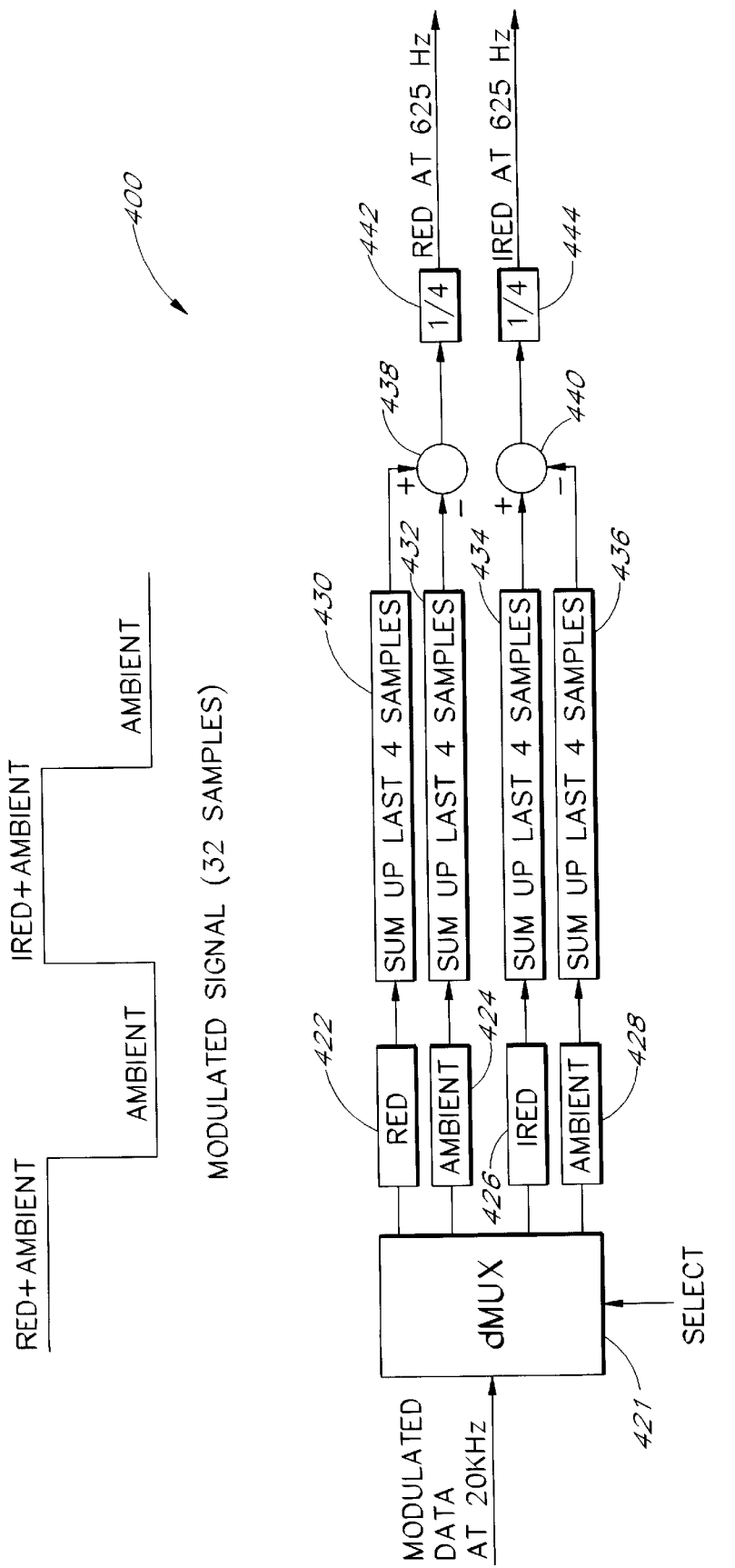
FIG. 15 illustrates additional detail regarding the demodulation module of FIG. 14.

FIG. 15 illustrates the operation of the demodulation module 400. The modulated signal format is depicted in FIG. 15. One full 625 Hz cycle of the composite signal is depicted in FIG. 15 with the first quarter cycle being the active red light plus ambient light signal, the second quarter cycle being an ambient light signal, the third quarter cycle being the active infrared plus ambient light signal, and the fourth quarter cycle being an ambient light signal. As depicted in FIG. 15, with a 20 KHz sampling frequency, the single full cycle at 625 Hz described above comprises 32 samples of 20 KHz data, eight samples relating to red plus ambient light, eight samples relating to ambient light, eight samples relating to infrared plus ambient light, and finally eight samples related to ambient light.

Because the signal processing system 334 controls the activation of the light emitters 300, 302, the entire system is synchronous. The data is synchronously divided (and thereby demodulated) into four 8-sample packets, with a time division demultiplexing operation as represented in a demultiplexing module 421. One eight-sample packet 422 represents the red plus ambient light signal; a second eight-sample packet 424 represents an ambient light signal; a third eight-sample packet 426 represents the attenuated infrared light plus ambient light signal; and a fourth eight-sample packet 428 represents the ambient light signal. A select signal synchronously controls the demultiplexing operation so as to divide the time-division multiplexed composite signal at the input of the demultiplexer 421 into its four subparts.

A sum of the last four samples from each packet is then calculated, as represented in the summing operations 430, 432, 434, 436 of FIG. 15. In the present embodiment, the last four samples are used because a low pass filter in the analog to digital converter 356 of the present embodiment has a settling time. Thus, collecting the last four samples from each 8-sample packet allows the previous signal to clear. This summing operation provides an integration operation which enhances noise immunity. The sum of the respective ambient light samples is then subtracted from the sum of the red and infrared samples, as represented in the subtraction modules 438, 440. The subtraction operation provides some attenuation of the ambient light signal present in the data. In the present embodiment, it has been found that approximately 20 dB attenuation of the ambient light is provided by the operations of the subtraction modules 438, 440. The resultant red and infrared sum values are divided by four, as represented in the divide by four modules 442, 444. Each resultant value provides one sample each of the red and infrared signals at 625 Hz.

It should be understood that the 625 Hz carrier frequency has been removed by the demodulation operation 400. The 625 Hz sample data at the output of the demodulation operation 400 is sample data without the carrier frequency. In order to satisfy Nyquist sampling requirements, less than 20 Hz is needed (understanding that the human pulse is about 25 to 250 beats per minute, or about 0.4 Hz–4 Hz). Accordingly, the 625 Hz resolution is reduced to 62.5 Hz in the decimation operation.

Figure 16:
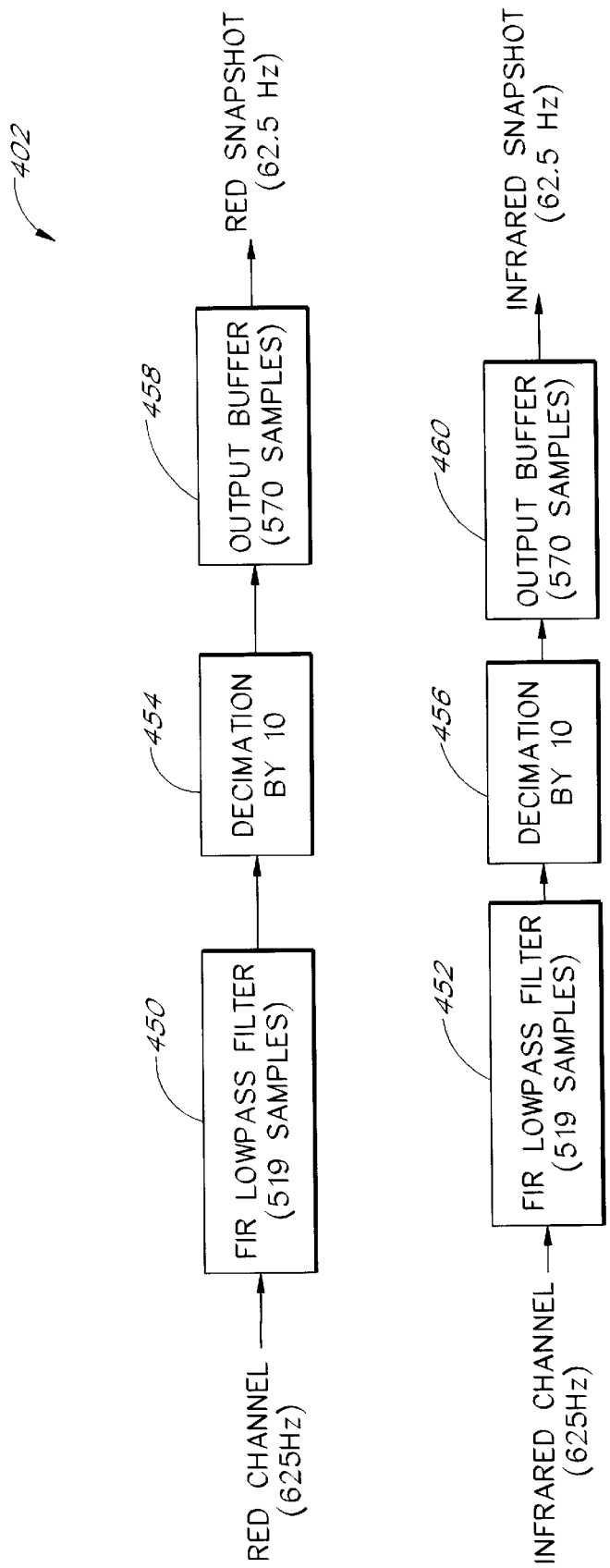
FIG. 16 illustrates additional detail regarding the decimation module of FIG. 14.

FIG. 16 illustrates the operations of the decimation module 402. The red and infrared sample data is provided at 625 Hz to respective red and infrared buffer/filters 450, 452. In the present embodiment, the red and infrared buffer/filters are 519 samples deep. Advantageously, the buffer filters 450, 452 function as continuous first-in, first-out buffers. The 519 samples are subjected to low-pass filtering. Preferably, the low-pass filtering has a cutoff frequency of approximately 7.5 Hz with attenuation of approximately −110 dB. The buffer/filters 450, 452 form a Finite Impulse Response (FIR) filter with coefficients for 519 taps. In order to reduce the sample frequency by ten, the low-pass filter calculation is performed every ten samples, as represented in respective red and infrared decimation by 10 modules 454, 456. In other words, with the transfer of each new ten samples into the buffer/filters 450, 452, a new low pass filter calculation is performed by multiplying the impulse response (coefficients) by the 519 filter taps. Each filter calculation provides one output sample for respective red and infrared output buffers 458, 460. In the present embodiment, the red and infrared output buffers 458, 460 are also continuous FIFO buffers that hold 570 samples of data. The 570 samples provide respective infrared and red samples or packets (also denoted "snapshot" herein) of samples. As depicted in FIG. 14, the output buffers provide sample data for the statistics operation module 404, saturation transform module 406, and the pulse rate module 410.

Figure 17:
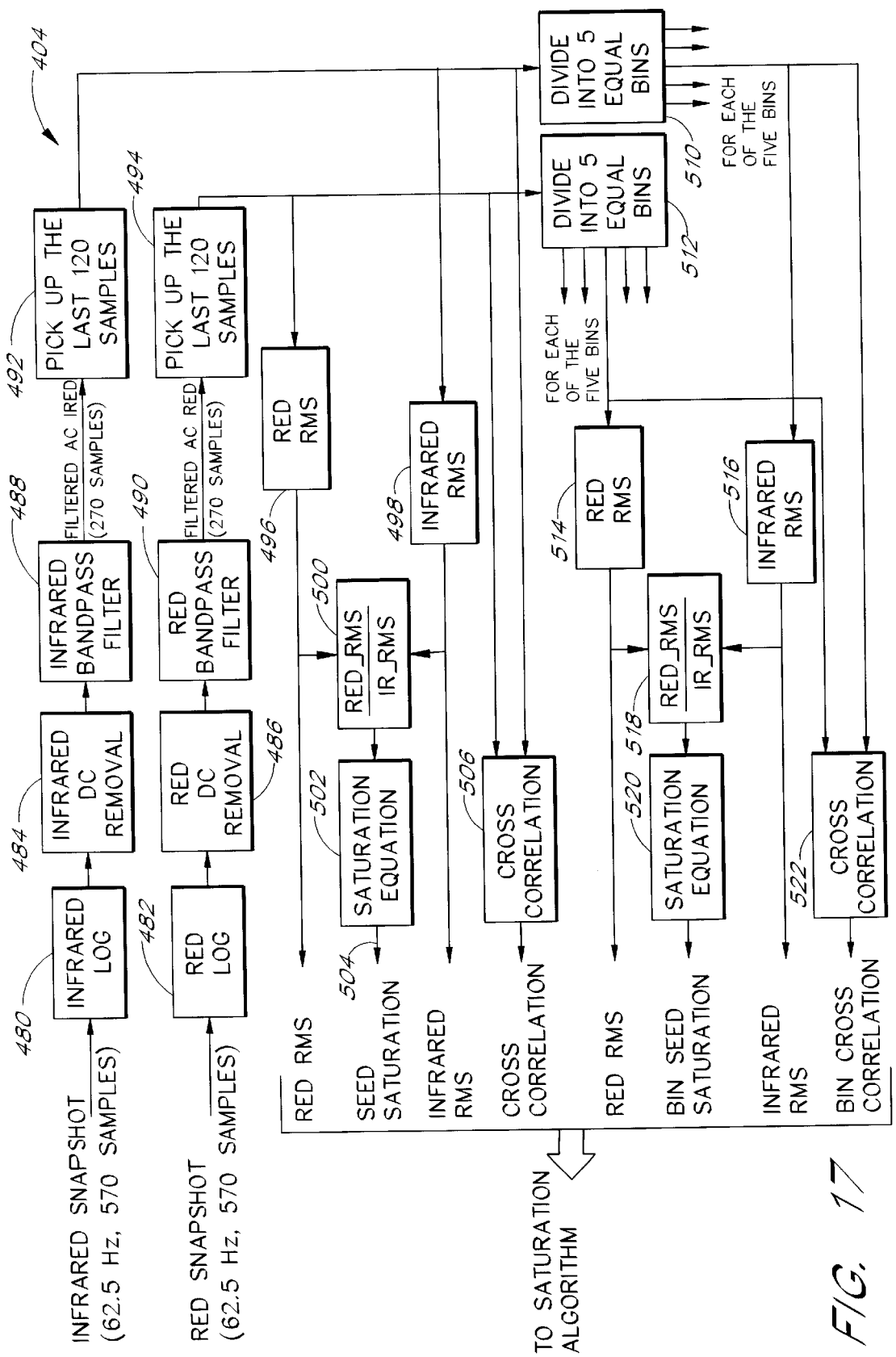
FIG. 17 represents a more detailed block diagram of the operations of the statistics module of FIG. 14.

FIG. 17 illustrates additional functional operation details of the statistics module 404. In summary, the statistics module 404 provides first order oximetry calculations and RMS signal values for the red and infrared channels. The statistics module also provides a cross-correlation output which indicates a cross-correlation between the red and infrared signals.

As represented in FIG. 17, the statistics operation accepts two packets of samples (e.g., 570 samples at 62.5 Hz in the present embodiment) representing the attenuated infrared and red signals, with the carrier frequency removed. The respective packets for infrared and red signals are normalized with a log function, as represented in the Log modules 480, 482. The normalization is followed by removal of the DC portion of the signals, as represented in the DC Removal modules 484, 486. In the present embodiment, the DC removal involves ascertaining the DC value of the first one of the samples (or the mean of the first several or the mean of an entire snapshot) from each of the respective red and infrared snapshots, and removing this DC value from all samples in the respective packets.

Once the DC signal is removed, the signals are subjected to bandpass filtering, as represented in red and infrared Bandpass Filter modules 488, 490. In the present embodiment, with 570 samples in each packet, the bandpass filters are configured with 301 taps to provide a FIR filter with a linear phase response and little or no distortion. In the present embodiment, the bandpass filter has a pass band from 34 beats/minute to 250 beats/minute. The 301 taps slide over the 570 samples in order to obtain 270 filtered samples representing the filtered red signal and 270 filtered samples representing the filtered infrared signal. In an ideal case, the bandpass filters 488, 490 remove the DC in the signal. However, the DC removal operations 484, 486 assist in DC removal in the present embodiment.

After filtering, the last 120 samples from each packet (of now 270 samples in the present embodiment) are selected for further processing as represented in Select Last 120 Samples modules 492, 494. The last 120 samples are selected because, in the present embodiment, the first 150 samples fall within the settling time for the Saturation Transfer module 406, which processes the same data packets, as further discussed below.

Conventional saturation equation calculations are performed on the red and infrared 120-sample packets. In the present embodiment, the conventional saturation calculations are performed in two different ways. For one calculation, the 120-sample packets are processed to obtain their overall RMS value, as represented in the first red and infrared RMS modules 496, 498. The resultant RMS values for red and infrared signals provide input values to a first RED_RMS/IR_RMS ratio operation 500, which provides the RMS red value to RMS infrared value ratio as an input to a saturation equation module 502. As well understood in the art, the ratio of the intensity of red to infrared attenuated light as detected for known red and infrared wavelengths (typically $\lambda \text{red}=650$ nm and $\lambda_{IR}=910$ nm) relates to the oxygen saturation of the patient. Accordingly, the saturation equation module 502 represents a conventional look-up table or the like which, for predetermined ratios, provides known saturation values at its output 504. The red and infrared RMS values are also provided as outputs of the statistics operations module 404.

In addition to the conventional saturation operation 502, the 120-sample packets are subjected to a cross-correlation operation as represented in a first cross-correlation module 506. The first cross-correlation module 506 determines if good correlation exists between the infrared and red signals. This cross correlation is advantageous for detecting defective or otherwise malfunctioning detectors. The cross correlation is also advantageous in detecting when the signal model (i.e., the model of Equations (1)–(3)) is satisfied. If correlation becomes too low between the two channels, the signal model is not met. In order to determine this, the normalized cross correlation can be computed by the cross-correlation module 506 for each snapshot of data. One such correlation function is as follows:

$$\frac{\Sigma S_1 S_2}{\sqrt{\Sigma S_1^2 \Sigma S_2^2}}$$

If the cross correlation is too low, the oximeter 299 provides a warning (e.g., audible, visual, etc.) to the operator. In the present embodiment, if a selected snapshot yields a normalized correlation of less than 0.75, the snapshot does not qualify. Signals which satisfy the signal model will have a correlation greater than the threshold.

The red and infrared 120-sample packets are also subjected to a second saturation operation and cross correlation in the same manner as described above, except the 120 samples are divided into 5 equal bins of samples (i.e., 5 bins of 24 samples each). The RMS, ratio, saturation, and cross correlation operations are performed on a bin-by-bin basis. These operations are represented in the Divide Into Five Equal Bins modules 510, 512, the second red and infrared RMS modules 514, 516, the second RED-RMS/IR-RMS ratio module 518, the second saturation equation module 520 and the second cross correlation module 522 in FIG. 17.

Figure 18:
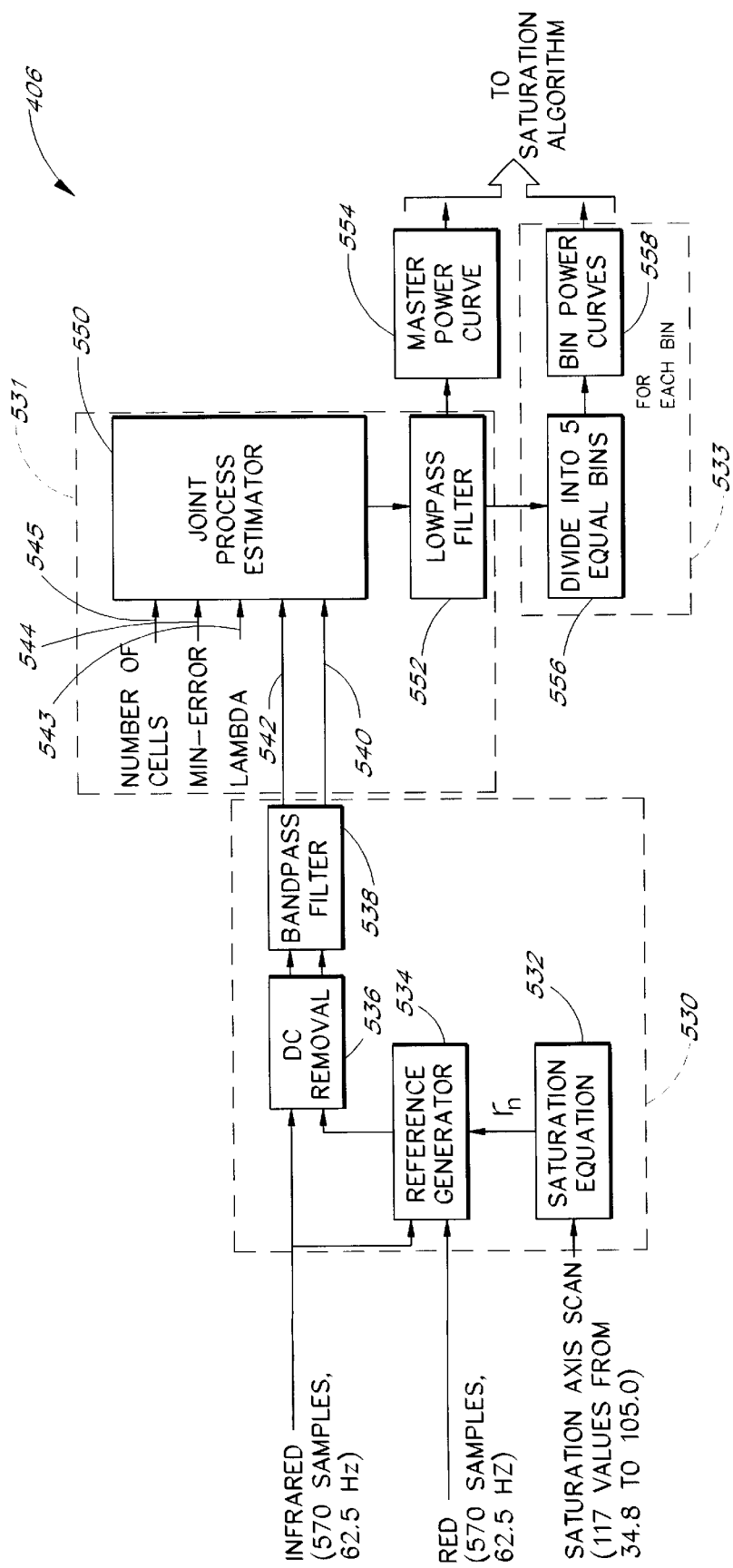
FIG. 18 illustrates a block diagram of the operations of one embodiment of the saturation transform module of FIG. 14.

FIG. 18 illustrates additional detail regarding the saturation transform module 406 depicted in FIG. 14. As illustrated in FIG. 18, the saturation transform module 406 comprises a reference processor 530, a correlation canceler 531, a master power curve module 554, and a bin power curve module 533. The saturation transform module 406 can be correlated to FIG. 7a which has a reference processor 26 and a correlation canceler 27 and an integrator 29 to provide a power curve for separate signal coefficients as depicted in FIG. 7c. The saturation transform module 406 obtains a saturation spectrum from the snapshots of data. In other words, the saturation transform 406 provides information of the saturation values present in the snapshots.

As depicted in FIG. 18, the reference processor 530 for the saturation transform module 406 has a saturation equation module 532, a reference generator module 534, a DC removal module 536 and a bandpass filter module 538. The red and infrared 570-sample packets from the decimation operation are provided to the reference processor 530. In addition, a plurality of possible saturation values (the "saturation axis scan") are provided as input to the saturation reference processor 530. In the present embodiment, 117 saturation values are provided as the saturation axis scan. In a preferred embodiment, the 117 saturation values range uniformly from a blood oxygen saturation of 34.8 to 105.0. Accordingly, in the present embodiment, the 117 saturation values provide an axis scan for the reference processor 530 which generates a reference signal for use by the correlation canceler 531. In other words, the reference processor is provided with each of the saturation values, and a resultant reference signal is generated corresponding to the saturation value. The correlation canceler is formed by a joint process estimator 550 and a low pass filter 552 in the present embodiment.

It should be understood that the scan values could be chosen to provide higher or lower resolution than 117 scan values. The scan values could also be non-uniformly spaced.

As illustrated in FIG. 18, the saturation equation module 532 accepts the saturation axis scan values as an input and provides a ratio "$r_n$" as an output. In comparison to the general discussion of FIGS. 7a–7c, this ratio "$r_n$" corresponds to the plurality of scan value discussed above in general. The saturation equation simply provides a known ratio "r" (red/infrared) corresponding to the saturation value received as an input.

The ratio "$r_n$" is provided as an input to the reference generator 534, as are the red and infrared sample packets. The reference generator 534 multiplies either the red or infrared samples by the ratio "$r_n$" and subtracts the value from the infrared or red samples, respectively. For instance, in the present embodiment, the reference generator 534 multiplies the red samples by the ratio "$r_n$" and subtracts this value from the infrared samples. The resulting values become the output of the reference generator 534. This operation is completed for each of the saturation scan values (e.g., 117 possible values in the present embodiment). Accordingly, the resultant data can be described as 117 reference signal vectors of 570 data points each, hereinafter referred to as the reference signal vectors. This data can be stored in an array or the like.

In other words, assuming that the red and infrared sample packets represent the red $S_{red}(t)$ and infrared $S_{IR}(t)$ measured signals which have primary s(t) and secondary n(t) signal portions, the output of the reference generator becomes the secondary reference signal n'(t), which complies with the signal model defined above, as follows:

$$n'(t)=S_{ir}(t)-r_n S_{red}(t)$$

In the present embodiment, the reference signal vectors and the infrared signal are provided as input to the DC removal module 536 of the reference processor 530. The DC removal module 536, like the DC removal modules 484, 486 in the statistics module 404, ascertains the DC value of the first of the samples for the respective inputs (or mean of the first several or all samples in a packet) and subtracts the respective DC baseline from the sample values. The resulting sample values are subjected to a bandpass filter 538.

The bandpass filter 538 of the reference processor 530 performs the same type of filtering as the bandpass filters 488, 490 of the statistics module 404. Accordingly, each set of 570 samples subjected to bandpass filtering results in 270 remaining samples. The resulting data at a first output 542 of the bandpass filter 538 is one vector of 270 samples (representing the filtered infrared signal in the present embodiment). The resulting data at a second output 540 of the bandpass filter 538, therefore, is 117 reference signal vectors of 270 data points each, corresponding to each of the saturation axis scan values provided to the saturation reference processor 530.

It should be understood that the red and infrared sample packets may be switched in their use in the reference processor 530. In addition, it should be understood that the DC removal module 536 and the bandpass filter module 538 can be executed prior to input of the data to the reference processor 530 because the calculations performed in the reference processor are linear. This results in a significant processing economy.

The outputs of the reference processor 530 provide first and second inputs to a joint process estimator 550 of the type described above with reference to FIG. 8. The first input to the joint process estimator 550 is the 270-sample packet representing the infrared signal in the present embodiment. This signal contains primary and secondary signal portions. The second input to the joint process estimator is the 117 reference signal vectors of 270 samples each.

The joint process estimator also receives a lambda input 543, a minimum error input 544 and a number of cells configuration input 545. These parameters are well understood in the art. The lambda parameter is often called the "forgetting parameter" for a joint process estimator. The lambda input 543 provides control for the rate of cancellation for the joint process estimator. In the present embodiment, lambda is set to a low value such as 0.8. Because statistics of the signal are non-stationary, a low value improves tracking. The minimum error input 544 provides an initialization parameter (conventionally known as the "initialization value") for the joint process estimator 550. In the present embodiment, the minimum error value is $10^{-6}$. This initialization parameter prevents the joint process estimator 500 from dividing by zero upon initial calculations. The number of cells input 545 to the joint process estimator 550 configures the number of cells for the joint process estimator. In the present embodiment, the number of cells for the saturation transform operation 406 is six. As well understood in the art, for each sine wave, the joint process estimator requires two cells. If there are two sine waves in the 35–250 beats/minute range, six cells allows for the two heart beat sine waves and one noise sine wave.

The joint process estimator 550 subjects the first input vector on the first input 542 to a correlation cancellation based upon each of the plurality of reference signal vectors provided in the second input 540 to the correlation canceler 531 (all 117 reference vectors in sequence in the present embodiment). The correlation cancellation results in a single output vector for each of the 117 reference vectors. Each output vector represents the information that the first input vector and the corresponding reference signal vector do not have in common. The resulting output vectors are provided as an output to the joint process estimator, and subjected to the low pass filter module 552. In the present embodiment, the low pass filter 552 comprises a FIR filter with 25 taps and with a corner frequency of 10 Hz with the sampling frequency of 62.5 Hz (i.e., at the decimation frequency).

The joint process estimator 550 of the present embodiment has a settling time of 150 data points. Therefore, the last 120 data points from each 270 point output vector are used for further processing. In the present embodiment, the output vectors are further processed together as a whole, and are divided into a plurality of bins of equal number of data points. As depicted in FIG. 18, the output vectors are provided to a master power curve module 554 and to a Divide into five Equal Bins module 556. The Divide into Five Equal Bins module 556 divides each of the output vectors into five bins of equal number of data points (e.g., with 120 data points per vector, each bin has 24 data points). Each bin is then provided to the Bin Power Curves module 558.

Figure 22:
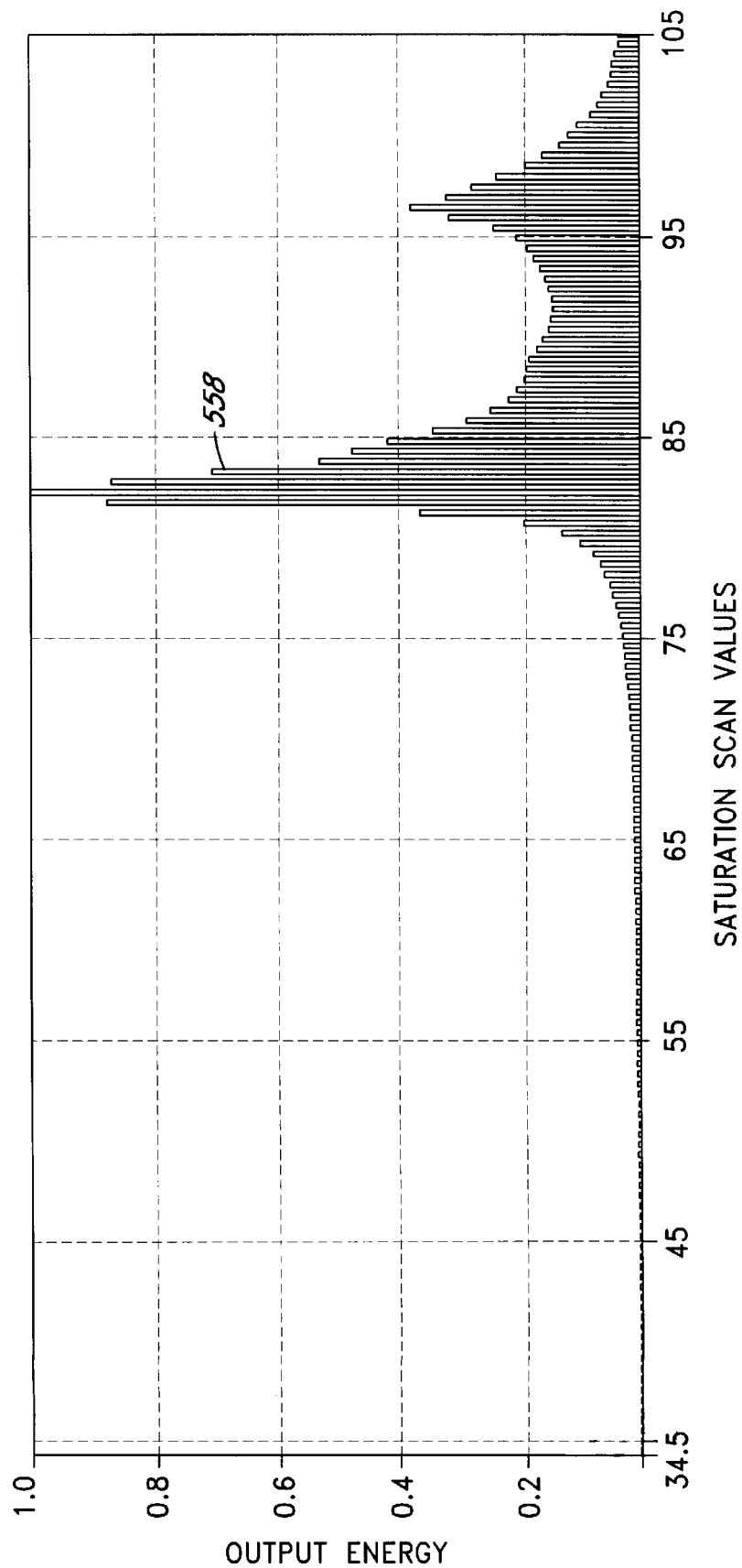
FIG. 22 illustrates a saturation transform curve in accordance with the principles of the present invention.

The Master Power Curve module 554 performs a saturation transform as follows: for each output vector, the sum of the squares of the data points is ascertained. This provides a sum of squares value corresponding to each output vector (each output vector corresponding to one of the saturation scan values). These values provide the basis for a master power curve 555, as further represented in FIG. 22. The horizontal axis of the power curve represents the saturation axis scan values and the vertical axis represents the sum of squares value (or output energy) for each output vector. In other words, as depicted in FIG. 22, each of the sum of squares could be plotted with the magnitude of the sum of squares value plotted on the vertical "energy output" axis at the point on the horizontal axis of the corresponding saturation scan value which generated that output vector. This results in a master power curve 558, an example of which is depicted in FIG. 22. This provides a saturation transform in which the spectral content of the attenuated energy is examined by looking at every possible saturation value and examining the output value for the assumed saturation value. As will be understood, where the first and second inputs to the correlation canceler 531 are mostly correlated, the sum of squares for the corresponding output vector of the correlation canceler 531 will be very low. Conversely, where the correlation between the first and second inputs to the correlation canceler 531 are not significantly correlated, the sum of squares of the output vector will be high. Accordingly, where the spectral content of the reference signal and the first input to the correlation canceler are made up mostly of physiological (e.g., movement of venous blood due to respiration) and non-physiological (e.g., motion induced) noise, the output energy will be low. Where the spectral content of the reference signal and the first input to the correlation canceler are not correlated, the output energy will be much higher.

A corresponding transform is completed by the Bin Power Curves module 558, except a saturation transform power curve is generated for each bin. The resulting power curves are provided as the outputs of the saturation transform module 406.

In general, in accordance with the signal model of the present invention, there will be two peaks in the power curves, as depicted in FIG. 22. One peak corresponds to the arterial oxygen saturation of the blood, and one peak corresponds to the venous oxygen concentration of the blood. With reference to the signal model of the present invention, the peak corresponding to the highest saturation value (not necessarily the peak with the greatest magnitude) corresponds to the proportionality coefficient $r_a$. In other words, the proportionality coefficient $r_a$ corresponds to the red/infrared ratio which will be measured for the arterial saturation. Similarly, peak that corresponds to the lowest saturation value (not necessarily the peak with the lowest magnitude) will generally correspond to the venous oxygen saturation, which corresponds to the proportionality coefficient $r_v$ in the signal model of the present invention. Therefore, the proportionality coefficient $r_v$ will be a red/infrared ratio corresponding to the venous oxygen saturation.

Figure 19:
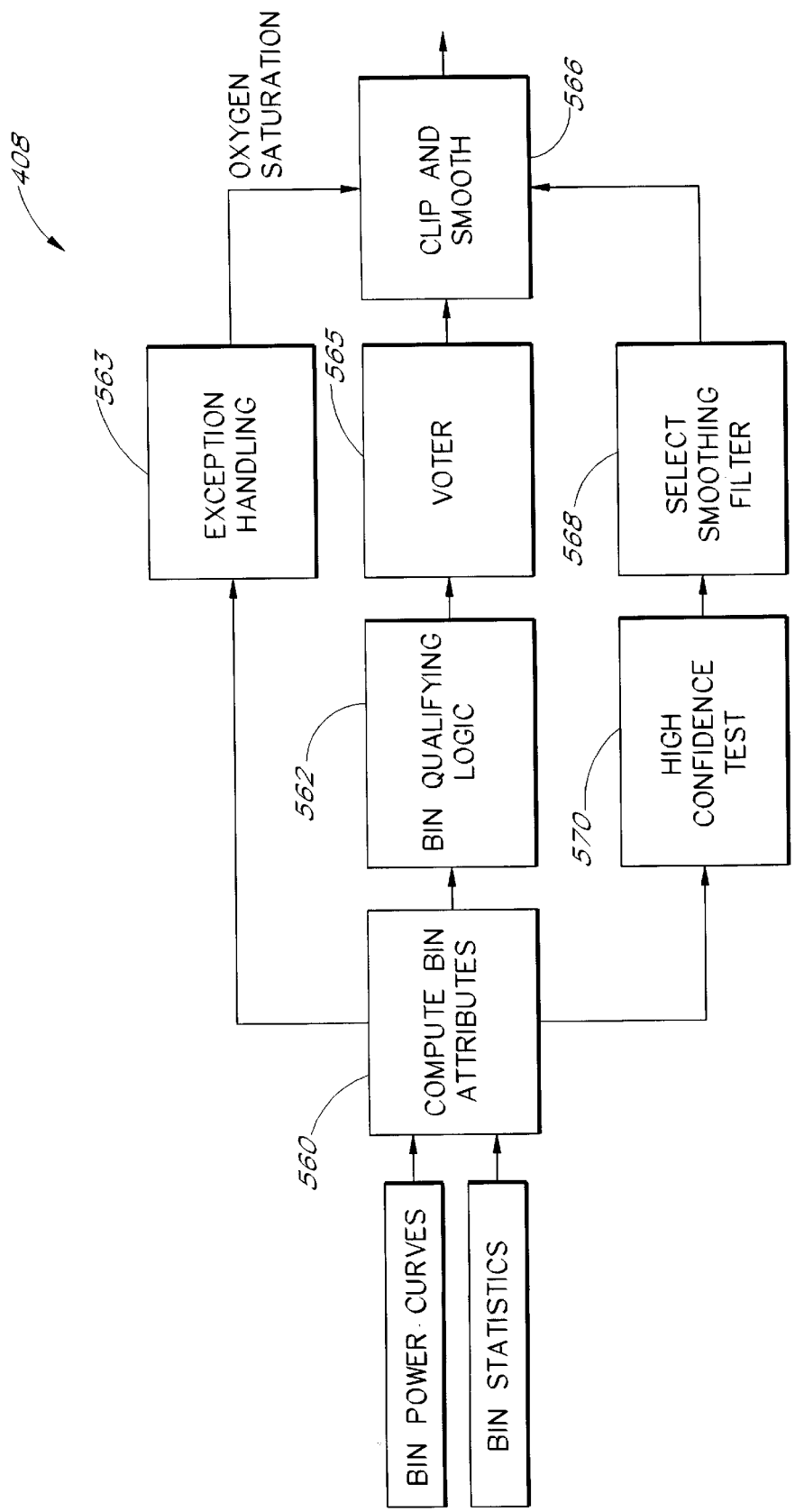
FIG. 19 illustrates a block diagram of the operation of the saturation calculation module of FIG. 14.

In order to obtain arterial oxygen saturation, the peak in the power curves corresponding to the highest saturation value could be selected. However, to improve confidence in the value, further processing is completed. FIG. 19 illustrates the operation of the saturation calculation module 408 based upon the output of the saturation transform module 406 and the output of the statistics module 404. As depicted in FIG. 19, the bin power curves and the bin statistics are provided to the saturation calculation module 408. In the present embodiment, the master power curves are not provided to the saturation module 408 but can be displayed for a visual check on system operation. The bin statistics contain the red and infrared RMS values, the seed saturation value, and a value representing the cross-correlation between the red and infrared signals from the statistics module 404.

The saturation calculation module 408 first determines a plurality of bin attributes as represented by the Compute Bin Attributes module 560. The Compute Bin Attributes module 560 collects a data bin from the information from the bin power curves and the information from the bin statistics. In the present embodiment, this operation involves placing the saturation value of the peak from each power curve corresponding to the highest saturation value in the data bin. In the present embodiment, the selection of the highest peak is performed by first computing the first derivative of the power curve in question by convolving the power curve with a smoothing differentiator filter function. In the present embodiment, the smoothing differentiator filter function (using a FIR filter) has the following coefficients:
0.014964670230367
0.098294046682706
0.204468276324813
2.717182664241813
5.704485606695227
0.000000000000000
−5.704482606695227
−2.717182664241813
−0.204468276324813
−0.098294046682706
−0.014964670230367
This filter performs the differentiation and smoothing. Next, each point in the original power curve in question is evaluated and determined to be a possible peak if the following conditions are met: (1) the point is at least 2% of the maximum value in the power curve; (2) the value of the first derivative changes from greater than zero to less than or equal to zero. For each point that is found to be a possible peak, the neighboring points are examined and the largest of the three points is considered to be the true peak.

The peak width for these selected peaks is also calculated. The peak width of a power curve in question is computed by summing all the points in the power curve and subtracting the product of the minimum value in the power curve and the number of points in the power curve. In the present embodiment, the peak width calculation is applied to each of the bin power curves. The maximum value is selected as the peak width.

In addition, the infrared RMS value from the entire snapshot, the red RMS value, the seed saturation value for each bin, and the cross correlation between the red and infrared signals from the statistics module 404 are also placed in the data bin. The attributes are then used to determine whether the data bin consists of acceptable data, as represented in a Bin Qualifying Logic module 562.

If the correlation between the red and infrared signals is too low, the bin is discarded. If the saturation value of the selected peak for a given bin is lower than the seed saturation for the same bin, the peak is replaced with the seed saturation value. If either red or infrared RMS value is below a very small threshold, the bins are all discarded, and no saturation value is provided, because the measured signals are considered to be too small to obtain meaningful data. If no bins contain acceptable data, the exception handling module 563 provides a message to the display 336 that the data is erroneous.

If some bins qualify, those bins that qualify as having acceptable data are selected, and those that do not qualify are replaced with the average of the bins that are accepted. Each bin is given a time stamp in order to maintain the time sequence. A voter operation 565 examines each of the bins and selects the three highest saturation values. These values are forwarded to a clip and smooth operation 566.

The clip and smooth operation 566 basically performs averaging with a low pass filter. The low pass filter provides adjustable smoothing as selected by a Select Smoothing Filter module 568. The Select Smoothing Filter module 568 performs its operation based upon a confidence determination performed by a High Confidence Test module 570. The high confidence test is an examination of the peak width for the bin power curves. The width of the peaks provides some indication of motion by the patient—wider peaks indicating motion. Therefore, if the peaks are wide, the smoothing filter is slowed down. If peaks are narrow, the smoothing filter speed is increased. Accordingly, the smoothing filter 566 is adjusted based on the confidence level. The output of the clip and smooth module 566 provides the oxygen saturation values in accordance with the present invention.

In the presently preferred embodiment, the clip and smooth filter 566 takes each new saturation value and compares it to the current saturation value. If the magnitude of the difference is less than 16 (percent oxygen saturation) then the value is pass. Otherwise, if the new saturation value is less than the filtered saturation value, the new saturation value is changed to 16 less than the filtered saturation value. If the new saturation value is greater than the filtered saturation value, then the new saturation value is changed to 16 more than the filtered saturation value.

During high confidence (no motion), the smoothing filter is a simple one-pole or exponential smoothing filter which is computed as follows:

$$y(n)=0.6 * x(n)+0.4 * y(n-1)$$

where x(n) is the clipped new saturation value, and y(n) is the filtered saturation value.

During motion condition, a three-pole IIR (infinite impulse response) filter is used. Its characteristics are controlled by three time constants $t_a$, $t_b$, and $t_c$ with values of 0.985, 0.900, and 0.94 respectively. The coefficients for a direct form I, IIR filter are computed from these time constants using the following relationships:

$a_0=0$
$a_1=t_b+(t_c)(t_a+t_b)$
$a_2=(-t_b)(t_c)(t_a+t_b+(t_c)(t_a))$
$a_3=(t_b)^2(t_c)^2(t_a)$ $b_0 = 1 - t_b - (t_c)(t_a + (t_c)(t_b))$
$b_1 = 2(t_b)(t_c)(t_a - 1)$
$b_2 = (t_b)(t_c)(t_b + (t_c)(t_a) - (t_b)(t_c)(t_a) - t_a$

Figure 20:
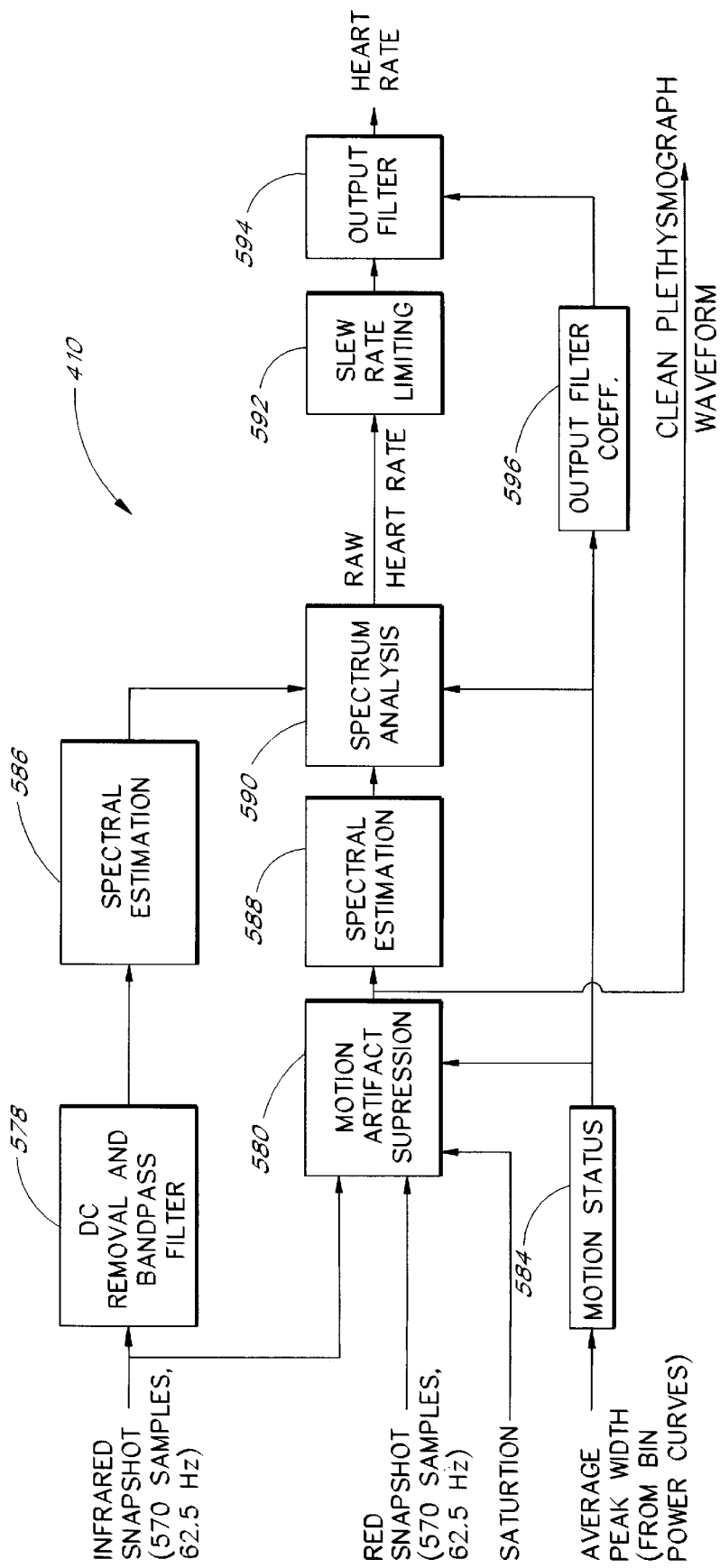
FIG. 20 illustrates a block diagram of the operations of the pulse rate calculation module of FIG. 14.
Figure 21:
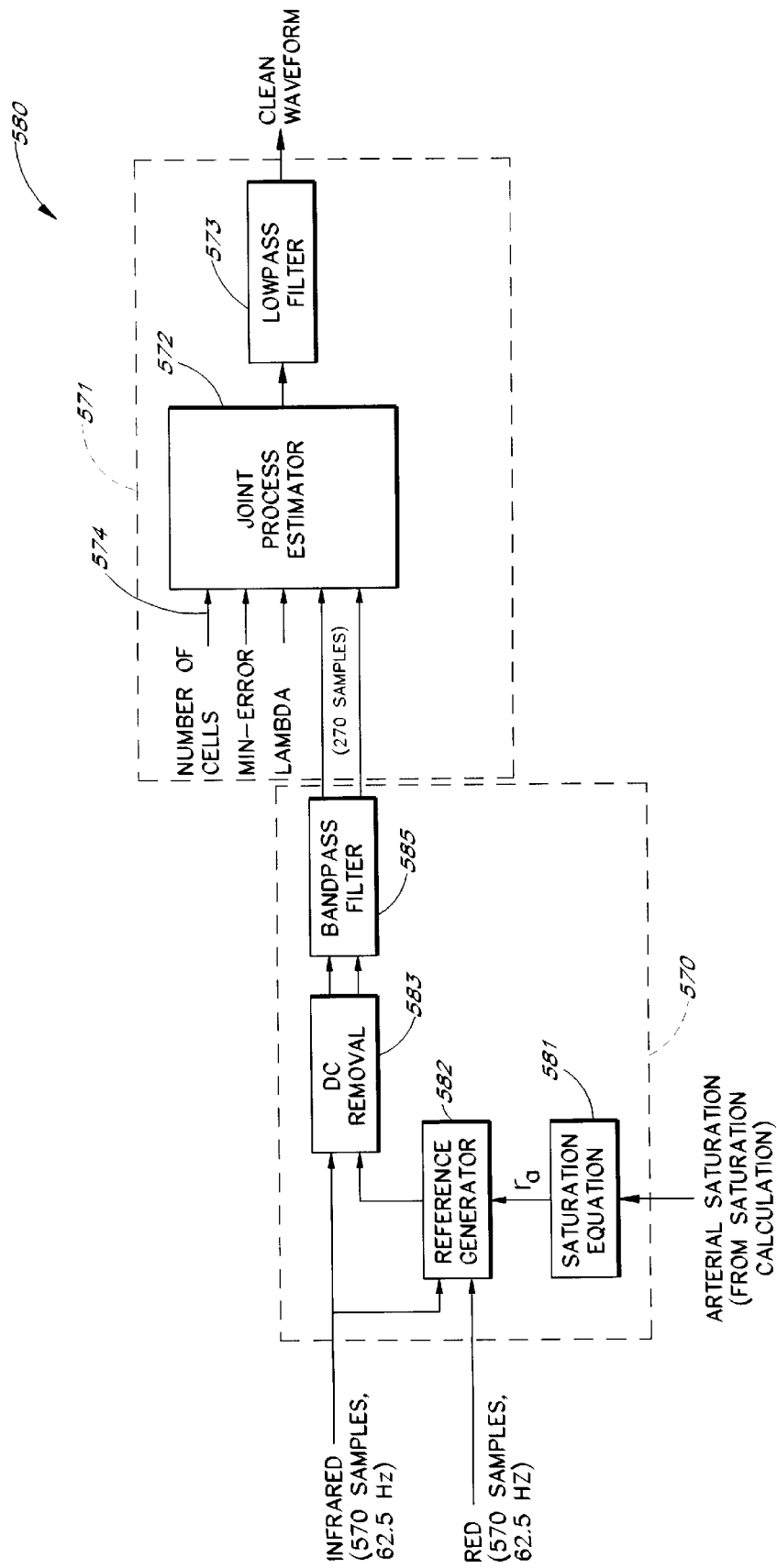
FIG. 21 illustrates a block diagram of the operations of the motion artifact suppression module of FIG. 20.

FIGS. 20 and 21 illustrate the pulse rate module 410 (FIG. 14) in greater detail. As illustrated in FIG. 20, the heart rate module 410 has a transient removal and bandpass filter module 578, a motion artifact suppression module 580, a saturation equation module 582, a motion status module 584, first and second spectral estimation modules 586, 588, a spectrum analysis module 590, a slew rate limiting module 592, an output filter 594, and an output filter coefficient module 596.

As further depicted in FIG. 20, the heart rate module 410 accepts the infrared and red 570-sample snapshots from the output of the decimation module 402. The heart rate module 410 further accepts the saturation value which is output from the saturation calculation module 408. In addition, the maximum peak width as calculated by the confidence test module 570 (same as peak width calculation described above) is also provided as an input to the heart rate module 410. The infrared and red sample packets, the saturation value and the output of the motion status module 584 are provided to the motion artifact suppression module 580.

The average peak width value provides an input to a motion status module 584. In the present embodiment, if the peaks are wide, this is taken as an indication of motion. If motion is not detected, spectral estimation on the signals is carried out directly without motion artifact suppression.

In the case of motion, motion artifacts are suppressed using the motion artifact suppression module 580. The motion artifact suppression module 580 is nearly identical to the saturation transform module 406. The motion artifact suppression module 580 provides an output which connects as an input to the second spectral estimation module 588. The first and second spectral estimation modules 586, 588 have outputs which provide inputs to the spectrum analysis module 590. The spectrum analysis module 590 also receives an input which is the output of the motion status module 584. The output of the spectrum analysis module 590 is the initial heart rate determination of the heart rate module 410 and is provided as input to the slew rate limiting module 592. The slew rate limiting module 592 connects to the output filter 594. The output filter 594 also receives an input from the output filter coefficient module 596. The output filter 594 provides the filtered heart rate for the display 336 (FIG. 11).

In the case of no motion, one of the signals (the infrared signal in the present embodiment) is subjected to DC removal and bandpass filtering as represented in the DC removal and bandpass filter module 578. The DC removal and bandpass filter module 578 provide the same filtering as the DC removal and bandpass filter modules 536, 538. During no motion conditions, the filtered infrared signal is provided to the first spectral estimation module 586.

In the present embodiment, the spectral estimation comprises a Chirp Z transform that provides a frequency spectrum of heart rate information. The Chirp Z transform is used rather than a conventional Fourier Transform because a frequency range for the desired output can be designated in a Chirp Z transform. Accordingly, in the present embodiment, a frequency spectrum of the heart rate is provided between 30 and 250 beats/minute. In the present embodiment, the frequency spectrum is provided to a spectrum analysis module 590 which selects the first harmonic from the spectrum as the pulse rate. Usually, the first harmonic is the peak in the frequency spectrum that has the greatest magnitude and represents the pulse rate. However, in certain conditions, the second or third harmonic can exhibit the greater magnitude. With this understanding, in order to select the first harmonic, the first peak that has an amplitude of at least 1/20th of the largest peak in the spectrum is selected). This minimizes the possibility of selecting as the heart rate a peak in the Chirp Z transform caused by noise.

In the case of motion, a motion artifact suppression is completed on the snapshot with the motion artifact suppression module 580. The motion artifact suppression module 580 is depicted in greater detail in FIG. 21. As can be seen in FIG. 21, the motion artifact suppression module 580 is nearly identical to the saturation transform module 406 (FIG. 18). Accordingly, the motion artifact suppression module has a motion artifact reference processor 570 and a motion artifact correlation canceler 571.

The motion artifact reference processor 570 is the same as the reference processor 530 of the saturation transform module 406. However, the reference processor 570 utilizes the saturation value from the saturation module 408, rather than completing an entire saturation transform with the 117 saturation scan values. The reference processor 570, therefore, has a saturation equation module 581, a reference generator 582, a DC removal module 583, and a bandpass filter module 585. These modules are the same as corresponding modules in the saturation transform reference processor 530. In the present embodiment, the saturation equation module 581 receives the arterial saturation value from the saturation calculation module 408 rather than doing a saturation axis scan as in the saturation transform module 406. This is because the arterial saturation has been selected, and there is no need to perform an axis scan. Accordingly, the output of the saturation equation module 581 corresponds to the proportionality constant $r_a$ (i.e., the expected red to infrared ratio for the arterial saturation value). Otherwise, the reference processor 570 performs the same function as the reference processor 530 of the saturation transform module 406.

The motion artifact correlation canceler 571 is also similar to the saturation transform correlation canceler 531 (FIG. 18). However, the motion artifact suppression correlation canceler 571 uses a slightly different motion artifact joint process estimator 572. Accordingly, the motion artifact suppression correlation canceler 571 has a joint process estimator 572 and a low-pass filter 573. The motion artifact joint process estimator 572 differs from the saturation transform joint process estimator 550 in that there are a different number of cells (between 6 and 10 in the present embodiment), as selected by the Number of Cells input 574, in that the forgetting parameter differs (0.98 in the present embodiment), and in that the time delay due to adaptation differs. The low-pass filter 573 is the same as the low pass filter 552 of the saturation transform correlation canceler 531.

Because only one saturation value is provided to the reference processor, only one output vector of 270 samples results at the output of the motion artifact suppression correlation canceler 571 for each input packet of 570 samples. In the present embodiment, where the infrared wavelength is provided as a first input to the correlation canceler, the output of the correlation canceler 571 provides a clean infrared waveform. It should be understood that, as described above, the infrared and red wavelength signals could be switched such that a clean red waveform is provided at the output of the motion artifact suppression correlation canceler 571. The output of the correlation canceler 571 is a clean waveform because the actual saturation value of the patient is known which allows the reference processor 570 to generate a noise reference for inputting to the correlation canceler 571 as the reference signal. The clean waveform at the output of the motion artifact suppression module 580 is a clean plethysmograph waveform which can be forwarded to the display 336.

As described above, an alternative joint process estimator uses the QRD least squares lattice approach (FIGS. 8a, 9a and 10a). Accordingly, the joint process estimator 573 (as well as the joint process estimator 550) could be replaced with a joint process estimator executing the QRD least squares lattice operation.

Figure 21A:
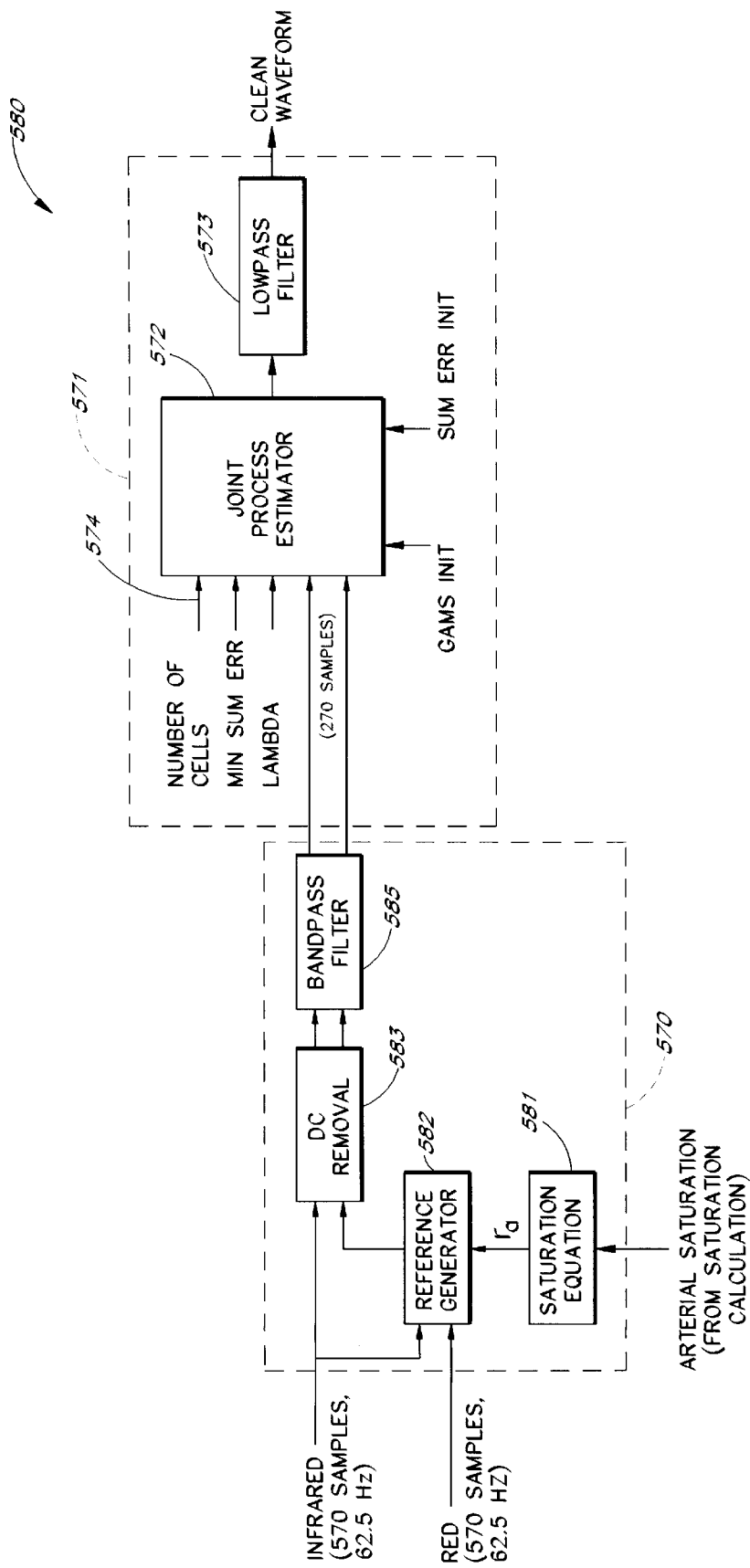
FIG. 21a illustrates an alternative block diagram for the operations of the motion artifact suppression module of FIG. 20.

FIG. 21a depicts an alternative embodiment of the motion artifact suppression module with a joint process estimator 572a replacing the joint process estimator 572. The joint process estimator 572a comprises a QRD least squares lattice system as in FIG. 10a. In accordance with this embodiment, different initialization parameters are used as necessary for the QRD algorithm.

The initialization parameters are referenced in FIG. 21a as "Number of Cells," "Lambda," "MinSumErr," "GamsInit," and "SumErrInit." Number of Cells and Lambda correspond to like parameters in the joint process estimator 572. GamsInit corresponds to the γ initialization variable for all stages except the zero order stage, which as set forth in the QRD equations above is initialized to '1'. SummErrInit provides the δ initialization parameter referenced above in the QRD equations. In order to avoid overflow, the larger of the actual calculated denominator in each division in the QRD equations and MinSumErr is used. In the present embodiment, the preferred initialization parameters are as follows:

Number of Cells=6
Lambda=0.8
MinSumErr=$10^{-20}$
GamsInit=$10^{-2}$
SumErrInit=$10^{-6}$.

The clean waveform output from the motion artifact suppression module 580 also provides an input to the second spectral estimation module 588. The second spectral estimation module 588 performs the same Chirp Z transform as the first spectral estimation module 586. In the case of no motion, the output from the first spectral estimation module 586 is provided to the spectrum analysis module 586; in the case of motion, the output from the second spectral estimation module 588 is provided to a spectrum analysis module 590. The spectrum analysis module 590 examines the frequency spectrum from the appropriate spectral estimation module to determine the pulse rate. In the case of motion, the spectrum analysis module 590 selects the peak in the spectrum with the highest amplitude, because the motion artifact suppression module 580 attenuates all other frequencies to a value below the actual heart rate peak. In the case of no motion, the spectrum analysis module selects the first harmonic in the spectrum as the heart rate as described above.

The output of the spectrum analysis module 590 provides the raw heart rate as an input to the slew rate limiting module 592, which provides an input to an output filter 594. In the present embodiment, the slew rate limiting module 592 prevents changes greater that 20 beats/minute per 2 second interval.

The output filter 594 comprises an exponential smoothing filter similar to the exponential smoothing filter described above with respect to the clip and smooth filter 566. The output filter is controlled via an output filter coefficient module 596. If motion is large, this filter is slowed down, if there is little or no motion, this filter can sample much faster and still maintain a clean value. The output from the output filter 594 is the pulse of the patient, which is advantageously provided to the display 336.

Alternative To Saturation Transform Module—Bank Of Filters

Figure 23:
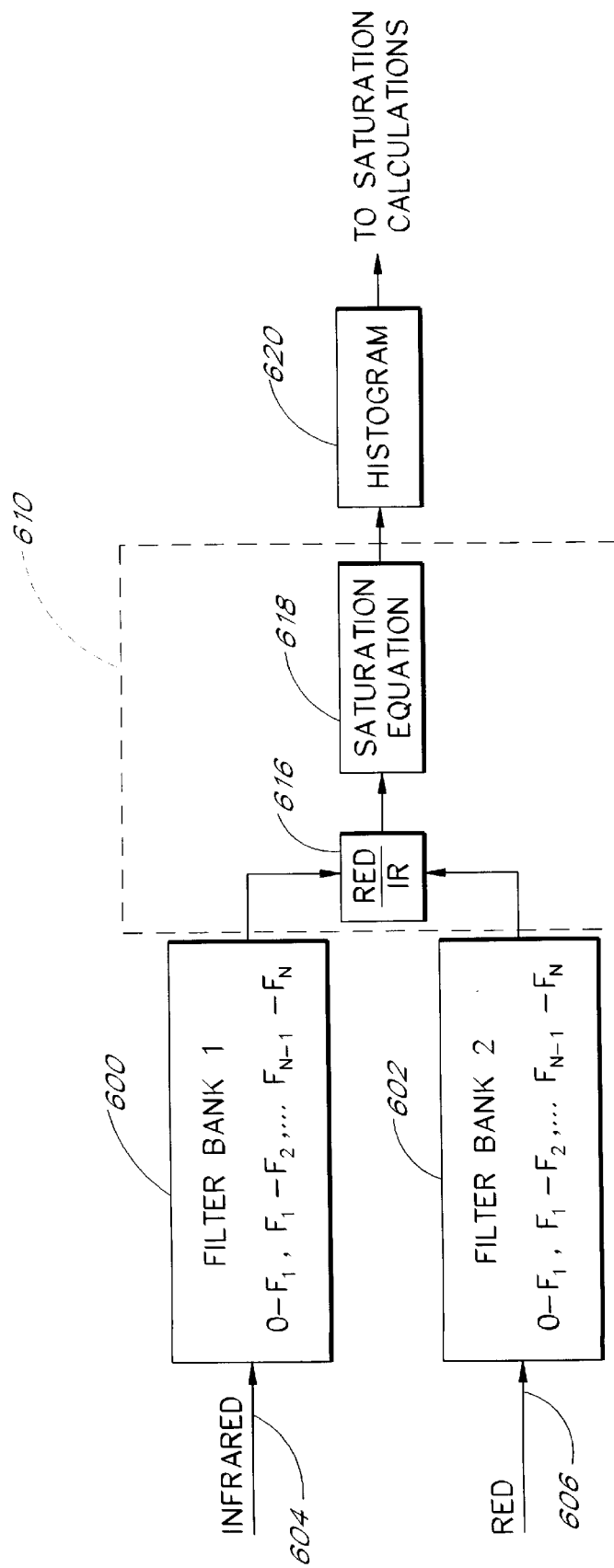
FIG. 23 illustrates a block diagram of an alternative embodiment to the saturation transform in order to obtain a saturation value.

An alternative to the saturation transform of the saturation transform module 406 can be implemented with a bank of filters as depicted in FIG. 23. As seen in FIG. 23, two banks of filters, a first filter bank 600 and a second filter bank 602 are provided. The first filter bank 600 receives a first measured signal $S_{\lambda b}(t)$ (the infrared signal samples in the present embodiment) on a corresponding first filter bank input 604, and the second filter bank 602 receives a second measured signal $S_{\lambda a}(t)$ (the red samples in the present embodiment) on a corresponding second filter bank input 606. In a preferred embodiment, the first and second filter banks utilize static recursive polyphase bandpass filters with fixed center frequencies and corner frequencies. Recursive polyphase filters are described in an article Harris, et. al. "Digital Signal Processing With Efficient Polyphase Recursive All-Pass filters" attached hereto as Appendix A. However, adaptive implementations are also possible. In the present implementation, the recursive polyphase bandpass filter elements are each designed to include a specific center frequency and bandwidth.

There are N filter elements in each filter bank. Each of the filter elements in the first filter bank 600 have a matching (i.e., same center frequency and bandwidth) filter element in the second filter bank 602. The center frequencies and the corner frequencies of N elements are each designed to occupy N frequency ranges, 0 to $F_1$, $F_1$–$F_2$, $F_2$–$F_3$, $F_3$–$F_4$ ... $F_{N-1}$–$F_N$ as shown in FIG. 23.

It should be understood that the number of filter elements can range from 1 to infinity. However, in the present embodiment, there are approximately 120 separate filter elements with center frequencies spread evenly across a frequency range of 25 beats/minute–250 beats/minute.

The outputs of the filters contain information about the primary and secondary signals for the first and second measured signals (red and infrared in the present example) at the specified frequencies. The outputs for each pair of matching filters (one in the first filter bank 600 and one in the second filter bank 602) are provided to saturation determination modules 610. FIG. 23 depicts only one saturation determination module 610 for ease of illustration. However, a saturation determination module can be provided for each matched pair of filter elements for parallel processing. Each saturation determination module has a ratio module 616 and a saturation equation module 618.

The ratio module 616 forms a ratio of the second output to the first output. For instance, in the present example, a ratio of each red RMS value to each corresponding infrared RMS value (Red/IR) is completed in the ratio module 616. The output of the ratio module 616 provides an input to the saturation equation module 618 which references a corresponding saturation value for the input ratio.

Figure 24:
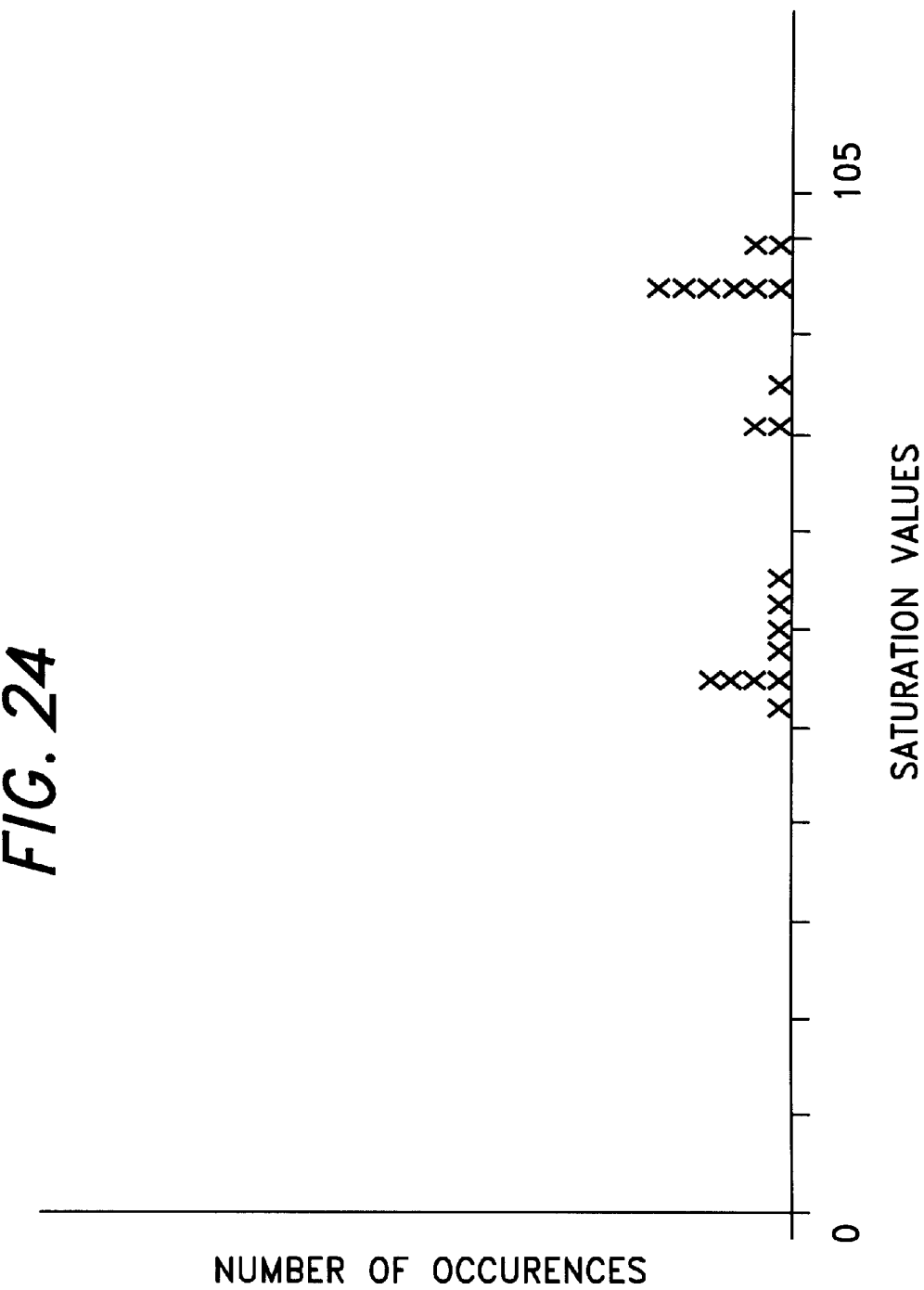
FIG. 24 illustrates a histogram saturation transform in accordance with the alternative embodiment of FIG. 23.

The output of the saturation equation modules 618 are collected (as represented in the histogram module 620) for each of the matched filter pairs. However, the data collected is initially a function of frequency and saturation. In order to form a saturation transform curve similar to the curve depicted in FIG. 22, a histogram or the like is generated as in FIG. 24. The horizontal axis represents the saturation value, and the vertical axis represents a summation of the number of points (outputs from the saturation equation modules 618) collected at each saturation value. In other words, if the output of the saturation equation module 618 for ten different matched filter pairs indicates a saturation value of 98%, then a point in the histogram of FIG. 24 would reflect a value of 10 at 98% saturation. This results in a curve similar to the saturation transform curve of FIG. 22. This operation is completed in the histogram module 620.

The results of the histogram provide a power curve similar to the power curve of FIG. 22. Accordingly, the arterial saturation can be calculated from the histogram by selecting the peak (greatest number of occurrences in the area of interest) corresponding to the highest saturation value (e.g., the peak 'c' in Figure peaks corresponding to the highest saturation value peak. Similarly, the venous or background saturation can be determined from the histogram by selecting the peak corresponding to the lowest saturation value (e.g., the peak 'd' in FIG. 24), in a manner similar to the processing in the saturation calculation module 408.

It should be understood that as an alternative to the histogram, the output saturation (not necessarily a peak in the histogram) corresponding to the highest saturation value could be selected as the arterial saturation with the corresponding ratio representing $r_a$. Similarly, the output saturation corresponding to the lowest saturation value could be selected as the venous or background saturation with the corresponding ratio representing $r_v$. For example, in this embodiment, the entry 'a' in the histogram of FIG. 24 would be chosen as the arterial saturation and the entry in the histogram 'b' with the lowest saturation value would be chosen as the venous or background saturation.

ALTERNATIVE DETERMINATION OF COEFFICIENTS $r_a$ AND $r_v$

As explained above, in accordance with the present invention, primary and secondary signal portions, particularly for pulse oximetry, can be modeled as follows:

$$S_{red} = s_1 + n_1 \text{ (red)} \quad (89)$$

$$S_{IR} = s_2 + n_2 \text{ (infrared)} \quad (90)$$

$$s_1 = r_a s_2 \text{ and } n_1 = r_v n_2 \quad (91)$$

Substituting Equation (91) into Equation (89) provides the following:

$$S_{red} = r_a s_2 + r_v n_2 \text{ (red)} \quad (92)$$

Note that $S_{red}$ and $S_{IR}$ are used in the model of equations (89)–(92). This is because the discussion below is particularly directed to blood oximetry. $S_{red}$ and $S_{IR}$ correspond to $S_1$ and $S_2$ in the preceding text, and the discussion that follows could be generalized for any measure signal $S_1$ and $S_2$.

As explained above, determining $r_a$ and $r_v$ (which correspond to arterial and venous blood oxygen saturation via a saturation equation) can be accomplished using the saturation transform described above doing a scan of many possible coefficients. Another method to obtain $r_a$ and $r_v$ based on red and infrared data is to look for $r_a$ and $r_v$ which minimize the correlation between $s_k$ and $n_k$, assuming $s_k$ is at least somewhat (and preferably substantially) uncorrelated with $n_k$ (where k=1 or 2). These values can be found by minimizing the following statistical calculation function for k=2:

$$\text{Correlation}(s_2, n_2) = \left| \sum_i s_2(S_{red_i}, S_{IR_i}, r_a, r_v) n_2(S_{red_i}, S_{IR_i}, r_a, r_v) \right| \quad (93)$$

where i represents time.

It should be understood that other correlation functions such as a normalized correlation could also be used.

Minimizing this quantity often provides a unique pair of $r_a$ and $r_v$ if the noise component is uncorrelated to the desired signal component. Minimizing this quantity can be accomplished by solving Equations (90) and (92) for $s_2$ and $n_2$, and finding the minimum of the correlation for possible values of $r_a$ and $r_v$. Solving for $s_2$ and $n_2$ provides the following:

$$\begin{pmatrix} S_{red} \\ S_{IR} \end{pmatrix} = \begin{pmatrix} r_a & r_v \\ 1 & 1 \end{pmatrix} \begin{pmatrix} s_2 \\ n_2 \end{pmatrix}$$

inverting the two-by-two matrix provides:
Thus, $$\begin{pmatrix} r_a & r_v \\ 1 & 1 \end{pmatrix}^{-1} = \frac{1}{r_a - r_v} \begin{pmatrix} 1 & -r_v \\ -1 & r_a \end{pmatrix}$$

$$\begin{pmatrix} s_2 \\ n_2 \end{pmatrix} = \frac{1}{r_a - r_v} \begin{pmatrix} 1 & -r_v \\ -1 & r_a \end{pmatrix} \begin{pmatrix} S_{red} \\ S_{IR} \end{pmatrix}$$

or:

$$s_2 = \frac{1}{r_a - r_v}(S_{red} - r_v S_{IR})$$

$$n_2 = \frac{1}{r_a - r_v}(-S_{red} + r_a S_{IR})$$

Preferably, the correlation of equation (93) is enhanced with a user specified window function as follows:

$$\text{Correlation}(s_2, n_2) = \quad (93a)$$

$$\left| \sum_{i=1}^{N} w_i s_2(S_{red_i}, S_{IR_i}, r_a, r_v) n_2(S_{red_1}, S_{IR_1}, r_a, r_v) \right|$$

The Blackman Window is the presently preferred embodiment. It should be understood that there are many additional functions which minimize the correlation between signal and noise. The function above is simply one. Thus, $$\text{Correlation}(s_2, n_2) = \quad (93b)$$

$$\left| \sum_{i=1}^{N} \left[ \frac{w_i}{(r_a - r_v)^2}(S_{red_i} - r_v S_{IR_i})(-S_{red_i} - r_a S_{IR_i}) \right] \right| =$$

$$\frac{1}{(r_a - r_v)^2} \left| -\sum_{i=1}^{N} (S_{red_i})^2 w_i + (r_a + r_v) \sum_{i=1}^{N} S_{IR_i} S_{red_i} w_i + (S_{IR_i})^2 w_i \right|$$

In order to implement the minimization on a plurality of discrete data points, the sum of the squares of the red sample points, the sum of the squares of the infrared sample points, and the sum of the product of the red times the infrared sample points are first calculated (including the window function, $w_i$):

$$RR = \sum_{i=1}^{N} (S_{red_i})^2 w_i$$

$$II = \sum_{i=1}^{N} (S_{IR_i})^2 w_i$$

$$IRR = \sum_{i=1}^{N} (S_{IR})(S_{red_i}) w_i$$

These values are used in the correlation equation (93b) Thus, the correlation equation becomes an equation in terms of two variables, $r_a$ and $r_v$. To obtain $r_a$ and $r_v$, an exhaustive scan is executed for a good cross-section of possible values for $r_a$ and $r_v$ (e.g., 20–50 values each corresponding to saturation values ranging from 30–105). The minimum of the correlation function is then selected and the values of $r_a$ and $r_v$ which resulted in the minimum are chosen as $r_a$ and $r_v$.

Once $r_a$ and $r_v$ have been obtained, arterial oxygen saturation and venous oxygen saturation can be determined by provided $r_a$ and $r_v$ to a saturation equation, such as the saturation equation 502 of the statistics module 404 which provides an oxygen saturation value corresponding to the ratios $r_a$ and $r_v$.

In a further implementation to obtain $r_a$ and $r_v$, the same signal model set forth above is again used. In order to determine $r_a$ and $r_v$ in accordance with this implementation, the energy in the signal $s_2$ is maximized under the constraint that $s_2$ is uncorrelated with $n_2$. Again, this implementation is based upon minimizing the correlation between s and n and on the signal model of the present invention where the signal s relates to the arterial pulse and the signal n is the noise (containing information on the venous blood, as well as motion artifacts and other noise); $r_a$ is the ratio (RED/IR) related to arterial saturation and $r_v$ is the ratio (RED/IR) related to venous saturation. Accordingly, in this implementation of the present invention, $r_a$ and $r_v$ are determined such that the energy of the signal $s_2$ is maximized where $s_2$ and $n_2$ are uncorrelated. The energy of the signal $s_2$ is given by the following equation:

$$\text{ENERGY}(s_2) = \frac{1}{(r_a - r_v)^2} \sum_{i=1}^{N} (S_{red} - r_v S_{IR})^2 \quad (94)$$

$$= \frac{1}{(r_a - r_v)^2} \sum_{i=1}^{N} (S_{red_i}^2) - 2r_v \sum_{i=1}^{N} (S_{red_i} S_{IR_i}) + \quad (95)$$

$$r_v^2 \sum_{i=1}^{N} (S_{IR_i}^2)$$

$$= \frac{1}{(r_a - r_v)^2} [R_1 - 2r_v R_{1,2} + r_v^2 R_2] \quad (96)$$

where $R_1$ is the energy of the red signal, $R_2$ is the energy of the infrared signal and $R_{1,2}$ is the correlation between the red and infrared signals.

The correlation between $s_2$ and $n_2$ is given by $$\text{Correlation}(s_2, n_2) = \frac{1}{(r_a - r_v)^2} \sum_{i=1}^{N} (S_{red_i} - r_v S_{ir_i})(-S_{red_i} + r_a S_{IR_i}) \quad (97)$$

$$= \frac{1}{(r_a - r_v)^2} [-R_1 + (r_a + r_v) R_{1,2} - r_v r_a R_2]$$

As explained above, the constraint is that $s_k$ and $n_k$ (k=2 for the present example) are uncorrelated. This "decorrelation constraint" is obtained by setting the correlation of Equation (97) to zero as follows:

$$-R_1 + (r_a + r_v) R_{1,2} - r_a r_v R_2 = 0 \quad (98)$$

In other words, the goal is to maximize equation (94) under the constraint of equation (98).

In order to obtain the goal, a cost function is defined (e.g., a Lagrangian optimization in the present embodiment) as follows:

$$J(r_a, r_v, \mu) = \quad (99)$$
$$\frac{1}{(r_a - r_v)^2} [R_1 - 2r_v R_{1,2} + r_v^2 R_2 + \mu(-R_1 + (r_a + r_v) R_{1,2} - r_a r_v R_2)]$$

where 82 is the Lagrange multiplier. Finding the value of $r_a$, $r_v$ and $\mu$ that solve the cost function can be accomplished using a constrained optimization method such as described in Luenberger, *Linear & Nonlinear Programming*, Addison-Wesley, 2d Ed., 1984.

Along the same lines, if we assume that the red and infrared signals $S_{red}$ and $S_{IR}$ are non-static, the functions $R_1$, $R_2$ and $R_{1,2}$ defined above are time dependent. Accordingly, with two equations, two unknowns can be obtained by expressing the decorrelation constraint set forth in equation (98) at two different times. The decorrelation constraint can be expressed at two different times, $t_1$ and $t_2$, as follows:

$$-R_1(t_1) + (r_a + r_v) R_{1,2}(t_1) - r_a r_v R_2(t_1) = 0 \quad (100)$$

$$-R_1(t_2) + (r_a + r_v) R_{1,2}(t_2) - r_a r_v R_2(t_2) = 0 \quad (101)$$

Because equations (100) and (101) are non-linear in $r_a$ and $r_v$, a change of variables allows the use of linear techniques to solve these two equations. Accordingly, with $x = r_a + r_v$; $y = r_a r_v$ equations (100) and (101) become $$R_{1,2}(t_1) x - R_2(t_1) y = R_1(t_1) \quad (102)$$

$$R_{1,2}(t_2) x - R_2(t_2) y = R_1(t_2) \quad (103)$$

These equation (102) and (103) can be solved for x and y. Then, solving for $r_a$ and $r_v$ from the changes of variables equations provides the following:

$$r_v + \frac{y}{r_v} = x = > r_v^2 - x r_v + y = 0 \quad (104)$$

Solving equation (104) results in two values for $r_v$. In the present embodiment, the $r_v$ value that results in $x^2 - r_v y > 0$ is selected. If both values of $r_v$ result in $x^2 - r_v y > 0$, the $r_v$ that maximizes the energy of $s_2$ (Energy($s_2$)) at $t_2$ is selected. $r_v$ is then substituted into the equations above to obtain $r_a$. Alternatively $r_a$ can be found directly in the same manner $r_v$ was determined.

Alternative To Saturation Transform—Complex FFT

Figure 25A:
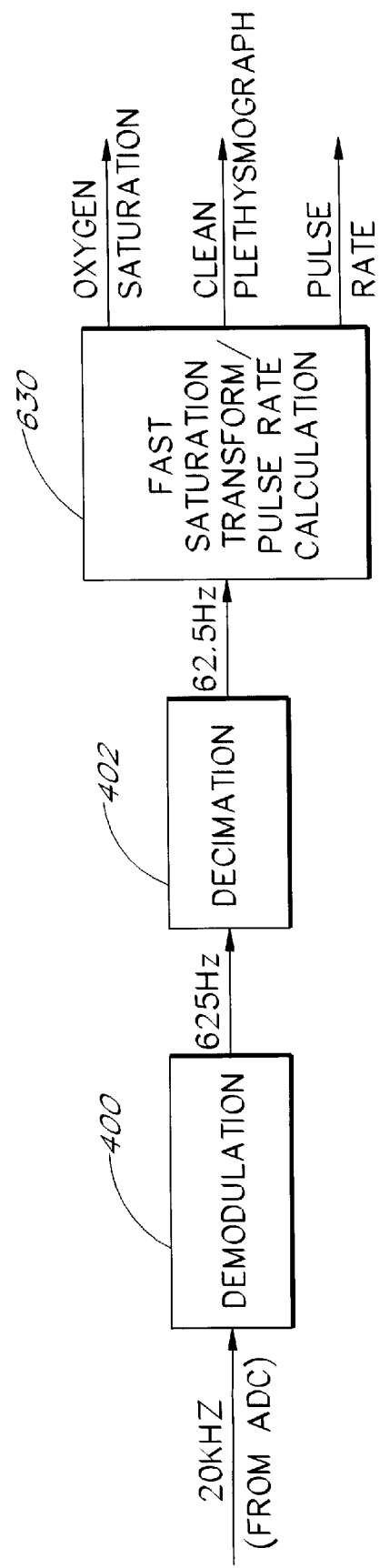
FIGS. 25A–25C illustrate yet another alternative embodiment in order to obtain the saturation.
Figure 25B:
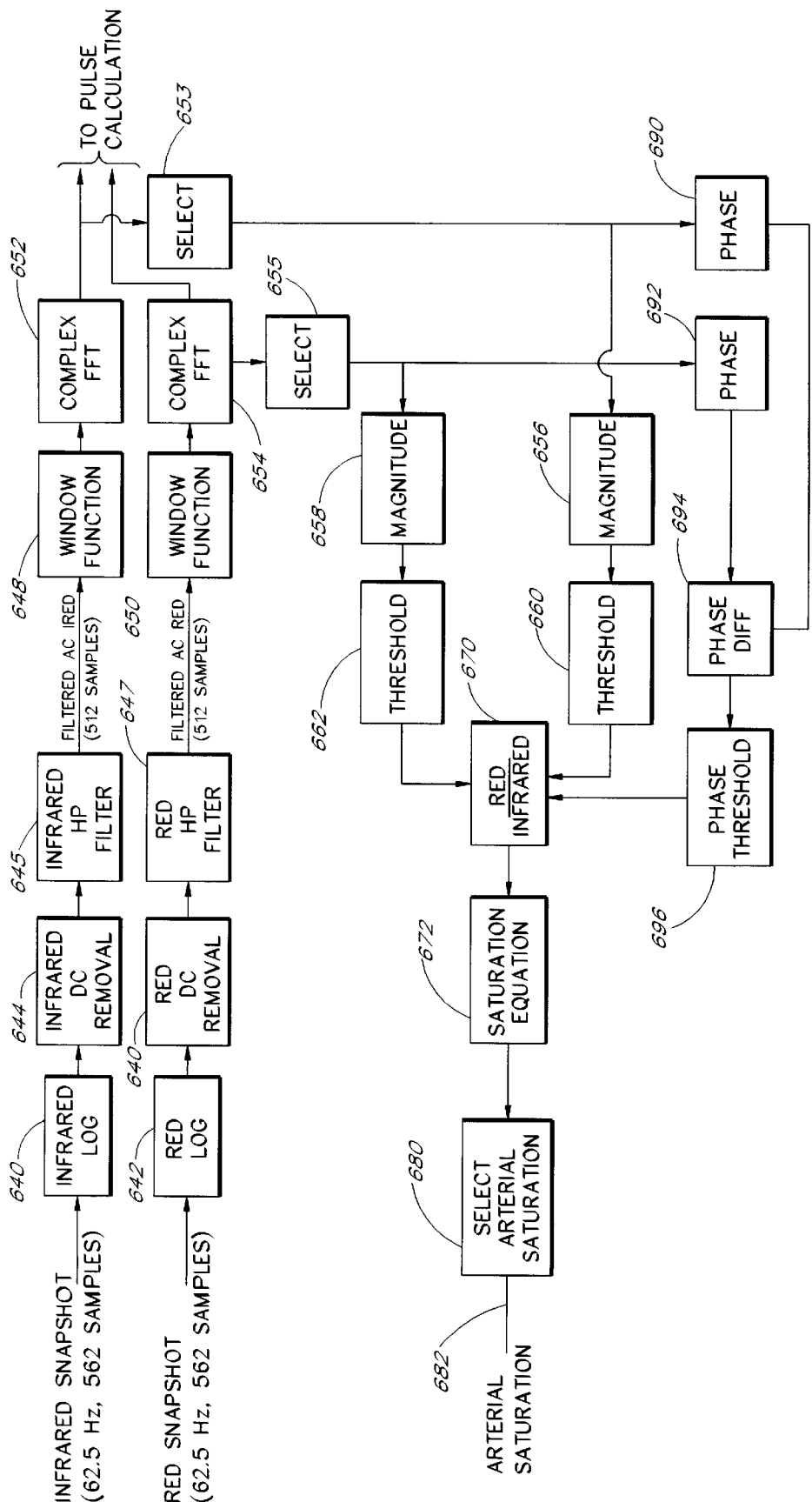
Figure 25C:
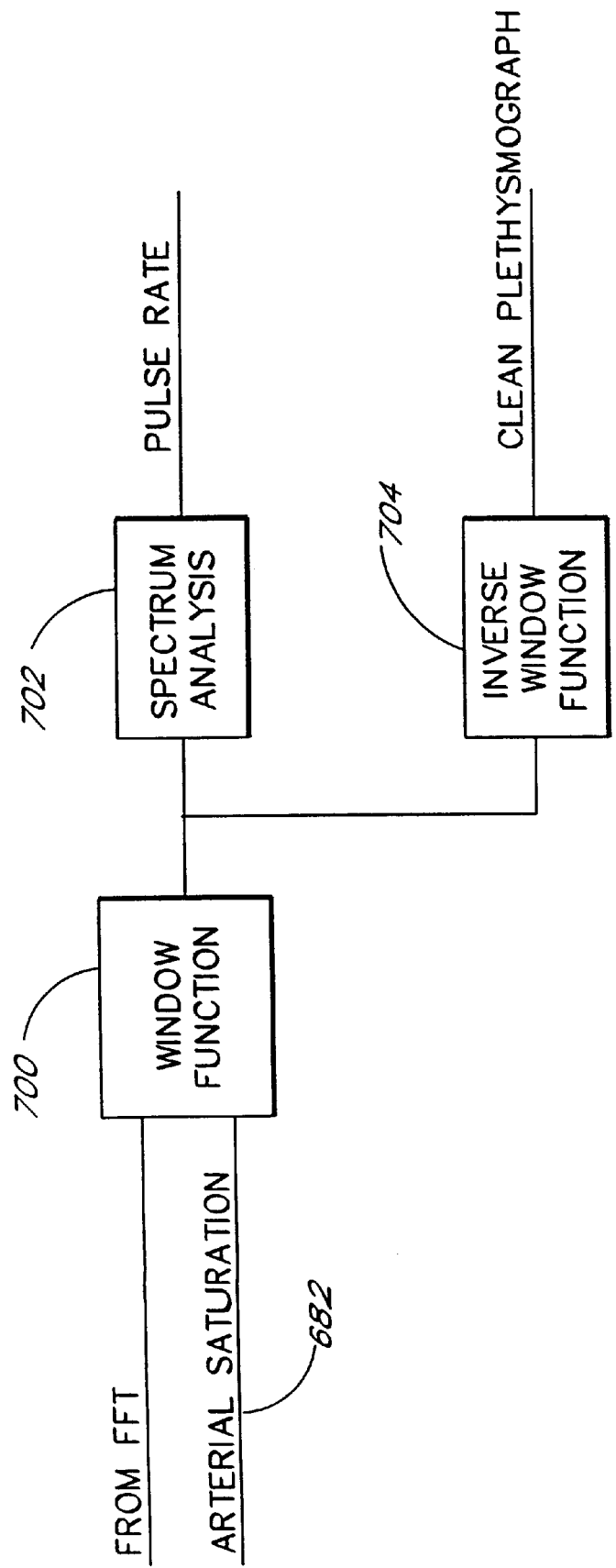

The blood oxygen saturation, pulse rate and a clean plethysmographic waveform of a patient can also be obtained using the signal model of the present invention using a complex FFT, as explained further with reference to FIGS. 25A–25C. In general, by utilizing the signal model of equations (89)–(92) with two measured signals, each with a first portion and a second portion, where the first portion represents a desired portion of the signal and the second portion represents the undesired portion of the signal, and where the measured signals can be correlated with coefficients $r_a$ and $r_v$, a fast saturation transform on a discrete basis can be used on the sample points from the output of the decimation operation 402.

FIG. 25A corresponds generally to FIG. 14, with the fast saturation transform replacing the previously described saturation transform. In other words, the operations of FIG. 25A can replace the operations of FIG. 14. As depicted in FIG. 25A, the fast saturation transform is represented in a fast saturation transform/pulse rate calculation module 630. As in FIG. 14, the outputs are arterial oxygen saturation, a clean plethysmographic waveform, and pulse rate. FIGS. 25B and 25C illustrate additional detail regarding the fast saturation transform/pulse rate calculation module 630. As depicted in FIG. 25B, the fast saturation transform module 630 has infrared log and red log modules 640, 642 to perform a log normalization as in the infrared and red log modules 480, 482 of FIG. 17. Similarly, there are infrared DC removal and red DC removal modules 644, 646. In addition, there are infrared and red high-pass filter modules 645, 647, window function modules 648, 640, complex FFT modules 652, 654, select modules 653, 655, magnitude modules 656, 658, threshold modules 660, 662, a point-by-point ratio module 670, a saturation equation module 672, and a select saturation module 680. There are also phase modules 690, 692, a phase difference module 694, and a phase threshold module 696. The output of the select saturation module 680 provides the arterial saturation on an arterial saturation output line 682.

In this alternative embodiment, the snapshot for red and infrared signals is 562 samples from the decimation module 402. The infrared DC removal module 644 and the red DC removal module 646 are slightly different from the infrared and red DC removal modules 484, 486 of FIG. 17. In the infrared and red DC removal modules 644, 646 of FIG. 25B, the mean of all 563 sample points for each respective channel is calculated. This mean is then removed from each individual sample point in the respective snapshot in order to remove the baseline DC from each sample. The outputs of the infrared and red DC removal modules 644, 646 provide inputs to respective infrared high-pass filter module 645 and red high-pass filter module 647.

The high-pass filter modules 645, 647 comprise FIR filters with 51 taps for coefficients. Preferably, the high-pass filters comprise Chebychev filters with a side-lobe level parameter of 30 and a corner frequency of 0.5 Hz (i.e., 30 beats/minute). It will be understood that this filter could be varied for performance. With 562 sample points entering the high-pass filters, and with 51 taps for coefficients, there are 512 samples provided from these respective infrared and red snapshots at the output of the high-pass filter modules. The output of the high-pass filter modules provides an input to the window function modules 648, 650 for each respective channel.

The window function modules 648, 650 perform a conventional windowing function. A Kaiser windowing function is used in the present embodiment. The functions throughout FIG. 25B maintain a point-by-point analysis. In the present embodiment, the time bandwidth product for the Kaiser window function is 7. The output of the window function modules provides an input to the respective complex Fast Fourier Transform (FFT) modules 652, 654.

The complex FFT modules 652, 654 perform complex FFTs on respective infrared and red channels on the data snapshots. The data from the complex FFTs is then analyzed in two paths, once which examines the magnitude and one which examines the phase from the complex FFT data points. However, prior to further processing, the data is provided to respective infrared and red select modules 653, 655 because the output of the FFT operation will provide repetitive information from 0–½ the sampling rate and from ½ the sampling rate to the sampling rate. The select modules select only samples from 0–½ the sampling rate (e.g., 0–31.25 Hz in the present embodiment) and then select from those samples to cover a frequency range of the heart rate and one or more harmonics of the heart rate. In the present embodiment, samples which fall in the frequency range of 20 beats per minute to 500 beats per minute are selected. This value can be varied in order to obtain harmonics of the heart rate as desired. Accordingly, the output of the select modules results in less than 256 samples. In the present embodiment, the sample points 2–68 of the outputs of the FFTs are utilized for further processing.

In the first path of processing, the output from the select modules 653, 655 are provided to respective infrared and red magnitude modules 656, 658. The magnitude modules 656, 658 perform a magnitude function wherein the magnitude on a point-by-point basis of the complex FFT points is selected for each of the respective channels. The outputs of the magnitude modules 656, 658 provide an input to infrared and red threshold modules 660, 662.

The threshold modules 660, 662 examine the sample points, on a point-by-point basis, to select those points where the magnitude of an individual point is above a particular threshold which is set at a percentage of the maximum magnitude detected among all the remaining points in the snapshots. In the present embodiment, the percentage for the threshold operation is selected as 1% of the maximum magnitude.

After thresholding, the data points are forwarded to a point-by-point ratio module 670. The point-by-point ratio module takes the red over infrared ratio of the values on a point-by-point basis. However, a further test is performed to qualify the points for which a ratio is taken. As seen in FIG. 25B, the sample points output from the select modules 653, 655 are also provided to infrared and red phase modules 690, 692. The phase modules 690, 692 select the phase value from the complex FFT points. The output of the phase modules 690, 692 is then presented to a phase difference module 694.

The phase difference module 694 calculates the difference in phase between the corresponding data points from the phase modules 690, 692. If the magnitude of the phase difference between any two corresponding points is less than a particular threshold (e.g., 0.1 radians) in the present embodiment), then the sample points qualify. If the phase of two corresponding sample points is too far apart, then the sample points are not used. The output of the phase threshold module 696 provides an enable input to the RED/IR rate module 670. Accordingly, in order for the ratio of a particular pair of sample points to be taken, the three tests are executed:

6. the red sample must pass the red threshold 660;

7. the infrared sample must pass the infrared threshold 662; and 8. the phase between the two points must be less than the predefined threshold as determined in the phase threshold 696.

For those sample points which qualify, a ratio is taken in the ratio module 670. For those points which do not qualify, the saturation is set to zero at the output of the saturation equation 672.

The resulting ratios are provided to a saturation equation module which is the same as the saturation equation modules 502, 520 in the statistics module 504. In other words, the saturation equation module 672 accepts the ratio on a point-by-point basis and provides as an output a corresponding saturation value corresponding to the discrete ratio points. The saturation points output from the saturation equation module 672 provide a series of saturation points which could be plotted as saturation with respect to frequency. The frequency reference was entered into the points at the complex FFT stage.

The arterial (and the venous) saturation can then be selected, as represented in the select arterial saturation module 680, in one of two methods according to the present invention. According to one method, the arterial saturation value can be selected simply as the point corresponding to the largest saturation value for all points output from the saturation equation module 672 for a packet. Alternatively, a histogram similar to the histogram of FIG. 22 can be generated in which the number of saturation values at different frequencies (points) are summed to form a histogram of the number of occurrences for each particular saturation value. In either method, the arterial saturation can be obtained and provided as an output to the select arterial saturation module on the arterial saturation output line 682. In order to obtain the venous saturation, the minimum arterial saturation value, of points that exhibit non-zero value, is selected rather than the maximum arterial saturation value. The saturation can be provided to the display 336.

The fast saturation transform information can also be used to provide the pulse rate and the clean plethysmographic wave form as further illustrated in FIG. 25C. In order to obtain the pulse rate and a clean plethysmographic wave form, several additional functions are necessary. As seen in FIG. 25C, the pulse rate and clean plethysmographic wave form are determined using a window function module 700, a spectrum analysis module 702 and an inverse window function module 704.

As depicted in FIG. 25C, the input to the window function module 700 is obtained from the output of the complex FFT modules 652 or 654. In the present embodiment, only one measured signal is necessary. Another input to the window function module 700 is the arterial saturation obtained from the output of the select arterial saturation module 680.

The window function module performs a windowing function selected to pass those frequencies that significantly correlate to the frequencies which exhibited saturation values very close to the arterial saturation value. In the present embodiment, the following windowing function is selected:

$$1 - \left[\frac{SAT_{art} - SAT_n}{100}\right]^{15} \tag{105}$$

where $SAT_n$ equals the saturation value corresponding to each particular frequency for the sample points and $SAT_{art}$ represents the arterial saturation as chosen at the output of the select arterial saturation module 680. This window function is applied to the window function input representing the complex FFT of either the red or the infrared signal. The output of the window function module 700 is a red or infrared signal represented with a frequency spectrum as determined by the FFT, with motion artifacts removed by the windowing function. It should be understood that many possible window functions can be provided. In addition, with the window function described above, it should be understood that using a higher power will provide more noise suppression.

In order to obtain pulse rate, the output points from the window function module 700 are provided to a spectrum analysis module 702. The spectrum analysis module 702 is the same as the spectrum analysis module 590 of FIG. 20. In other words, the spectrum analysis module 702 determines the pulse rate by determining the first harmonic in the frequency spectrum represented by the output points of the windowing function 700. The output of spectrum analysis module 702 is the pulse rate.

In order to obtain a clean plethysmographic waveform, the output of the windowing function 700 is applied to an inverse window function module 704. The inverse window function module 704 completes an inverse of the Kaiser window function of the window function module 648 or 650 of FIG. 25B. In other words, the inverse window function 704 does a point-by-point inverse of the Kaiser function for points that are still defined. The output is a clean plethysmographic waveform.

Accordingly, by using a complex FFT and windowing functions, the noise can be suppressed from the plethysmographic waveform in order to obtain the arterial saturation, the pulse rate, and a clean plethysmographic waveform. It should be understood that although the above description relates to operations primarily in the frequency domain, operations that obtain similar results could also be accomplished in the time domain.

Relation to Generalized Equations

The measurements described for pulse oximetry above are now related back to the more generalized discussion above. The signals (logarithm converted) transmitted through the finger 310 at each wavelength λa and λb are:

$$S_{\lambda a}(t) = S_{\lambda red1}(t) = \epsilon_{HbO2,\lambda a} c^A_{HbO2} x^A(t) + \epsilon_{Hb,\lambda a} c^A_{Hb} x^A(t) + \\ \epsilon_{HbO2,\lambda a} c^V_{HbO2} x^V(t) + \epsilon_{Hb,\lambda a} c^V_{Hb} x^V(t) + n_{\lambda a}(t); \tag{105a}$$

$$S_{\lambda a}(t) = \epsilon_{HbO2,\lambda a} c^A_{HbO2} x^A(t) + \epsilon_{Hb,\lambda a} c^A_{Hb} x^A(t) + n_{\lambda a}(t); \tag{105b}$$

$$S_{\lambda a}(t) = s_{\lambda a}(t) + n_{\lambda a}(t); \tag{105c}$$

$$S_{\lambda b}(t) = S_{\lambda red2}(t) = \epsilon_{HbO2,\lambda b} c^A_{HbO2} x^A(t) + \epsilon_{Hb,\lambda b} c^A_{Hb} x^A(t) + \\ \epsilon_{HbO2,\lambda b} c^V_{HbO2} x^V(t) + \epsilon_{Hb,\lambda b} c^V_{Hb} x^V(t) + n_{\lambda b}(t); \tag{106a}$$

$$S_{\lambda b}(t) = \epsilon_{HbO2,\lambda b} c^A_{HbO2} x^A(t) + \epsilon_{Hb,\lambda b} c^A_{Hb} x^A(t) + n_{\lambda b}(t) \tag{106b}$$

$$S_{\lambda b}(t) = s_{\lambda b}(t) + n_{\lambda b}(t) \tag{106c}$$

The variables above are best understood as correlated to FIG. 6c as follows: assume the layer in FIG. 6c containing $A_3$ and $A_4$ represents venous blood in the test medium, with $A_3$ representing deoxygenated hemoglobin (Hb) and $A_4$ representing oxygenated hemoglobin (HBO2) in the venous blood. Similarly, assume that the layer in FIG. 6c containing $A_5$ and $A_6$ represents arterial blood in the test medium, with $A_5$ representing deoxygenated hemoglobin (Hb) and $A_6$ representing oxygenated hemoglobin (HBO2) in the arterial blood. Accordingly, $c^V HbO2$ represents the concentration of oxygenated hemoglobin in the venous blood, $c^V Hb$ represents the concentration of deoxygenated hemoglobin in the venous blood, $x^V$ represents the thickness of the venous blood (e.g., the thickness the layer containing $A_3$ and $A_4$). Similarly, $c^A HbO2$ represents the concentration of oxygenated hemoglobin in the arterial blood, $c^A Hb$ represents the concentration of deoxygenated hemoglobin in the arterial blood, and $x^A$ represents the thickness of the arterial blood (e.g., the thickness of the layer containing $A_5$ and $A_6$)

The wavelengths chosen are typically one in the visible red range, i.e., λa, and one in the infrared range, i.e., λb. Typical wavelength values chosen are λa=660 nm and λb=910 nm. In accordance with the constant saturation method, it is assumed that $c^A_{HbO2}(t)/c^A_{Hb}(t)$=constant$_1$ and $c^V_{HbO2}(t)/c^V_{Hb}(t)$=constant$_2$. The oxygen saturation of arterial and venous blood changes slowly, if at all, with respect to the sample rate, making this a valid assumption. The proportionality coefficients for equations (105) and (106) can then be written as:

$$r_a(t) = \frac{\epsilon_{HbO2,\lambda a} c^A_{HbO2} x(t) + \epsilon_{Hb,\lambda a} c^A_{Hb} x(t)}{\epsilon_{HbO2,\lambda b} c^A_{HbO2} x(t) + \epsilon_{Hb,\lambda b} c^A_{Hb} x(t)} \quad (107)$$

$$s_{\lambda a}(t) = r_a(t) s_{\lambda b}(t) \quad (108a)$$

$$n_{\lambda a}(t) \neq r_a(t) n_{\lambda b}(t) \quad (109a)$$

$$n_{\lambda a}(t) = r_v(t) n_{\lambda b}(t) \quad (108b)$$

$$s_{\lambda a}(t) \neq r_v(t) s_{\lambda b}(t) \quad (109b)$$

In pulse oximetry, it is typically the case that both equations (108) and (109) can be satisfied simultaneously.

Multiplying equation (106) by $r_a(t)$ and then subtracting equation (106) from equation (105), a non-zero secondary reference signal n'(t) is determined by:

$$n'(t) = S_{\lambda a}(t) - r_a(t) S_{\lambda b}(t) \quad (110a)$$

$$= \epsilon_{HbO2,\lambda a} c^V_{HbO2} x^V(t) + \epsilon_{Hb,\lambda a} c^V_{Hb} x^V(t) + n_{\lambda a}(t) - \quad (111a)$$
$$r_a(t) [\epsilon_{HbO2,\lambda b} c^V_{HbO2} x^V(t) + \epsilon_{Hb,\lambda b} c^V_{Hb} x^V(t) + n_{\lambda b}(t)].$$

Multiplying equation (106) by $r_v(t)$ and then subtracting equation (106) from equation (105), a non-zero primary reference signal s'(t) is determined by:

$$s'(t) = S_{\lambda a}(t) - r_v(t) S_{\lambda b}(t) \quad (110b)$$

$$= s_{\lambda a}(t) - r_v(t) s_{\lambda b}(t) \quad (111b)$$

The constant saturation assumption does not cause the venous contribution to the absorption to be canceled along with the primary signal portions $s_{\lambda a}(t)$ and $s_{\lambda b}(t)$. Thus, frequencies associated with both the low frequency modulated absorption due to venous absorption when the patient is still and the modulated absorption due to venous absorption when the patient is moving are represented in the secondary reference signal n'(t). Thus, the correlation canceler or other methods described above remove or derive both erratically modulated absorption due to venous blood in the finger under motion and the constant low frequency cyclic absorption of venous blood.

Figure 26:
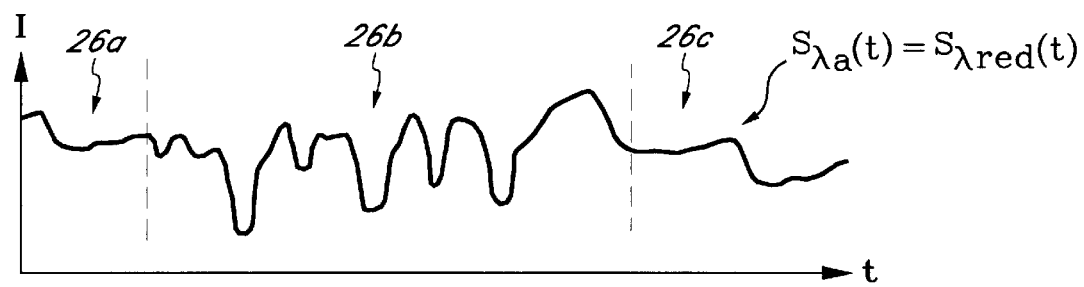
FIG. 26 illustrates a signal measured at a red wavelength $\lambda a = \lambda red = 660$ nm for use in a processor of the present invention for determining the secondary reference n'(t) or the primary reference s'(t) and for use in a correlation canceler. The measured signal comprises a primary portion $s_{\lambda a}(t)$ and a secondary portion $n_{\lambda a}(t)$.
Figure 27:
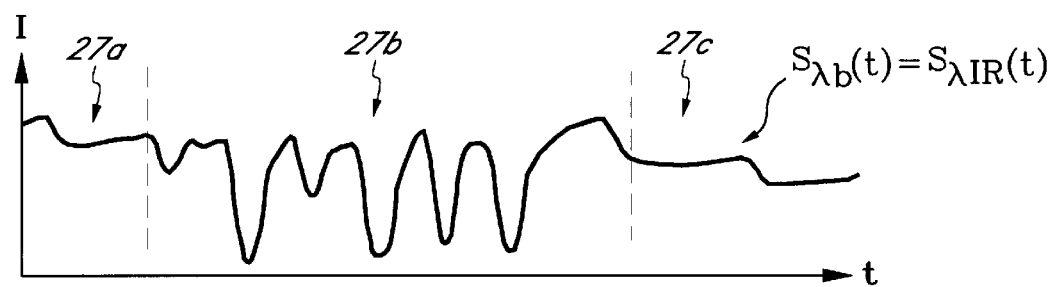
FIG. 27 illustrates a signal measured at an infrared wavelength $\lambda b = \lambda_{IR} = 910$ nm for use in a processor of the present invention for determining the secondary reference n'(t) or the primary reference s'(t) and for use in a correlation canceler. The measured signal comprises a primary portion $s_{\lambda b}(t)$ and a secondary portion $n_{\lambda b}(t)$.

To illustrate the operation of the oximeter of FIG. 11 to obtain clean waveform, FIGS. 26 and 27 depict signals measured for input to a reference processor of the present invention which employs the constant saturation method, i.e., the signals $S_{\lambda a}(t) = S_{\lambda red}(t)$ and $S_{\lambda b}(t) = S_{\lambda IR}(t)$. A first segment 26a and 27a of each of the signals is relatively undisturbed by motion artifact, i.e., the patient did not move substantially during the time period in which these segments were measured. These segments 26a and 27a are thus generally representative of the primary plethysmographic waveform at each of the measured wavelengths. A second segment 26b and 27b of each of the signals is affected by motion artifact, i.e., the patient did move during the time period in which these segments were measured. Each of these segments 26b and 27b shows large motion induced excursions in the measured signal. A third segment 26c and 27c of each of the signals is again relatively unaffected by motion artifact and is thus generally representative of the primary plethysmographic waveform at each of the measured wavelengths.

Figure 28:
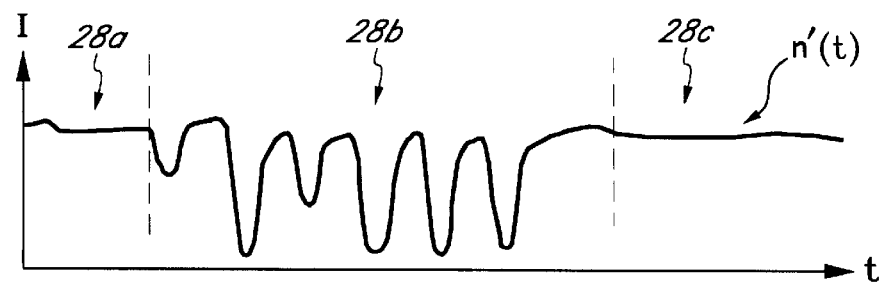
FIG. 28 illustrates the secondary reference n'(t) determined by a processor of the present invention.

FIG. 28 shows the secondary reference signal n'(t)=$n_{\lambda a}$(t)-$r_a n_{\lambda b}$(t), as determined by a reference processor of the present invention. Again, the secondary reference signal n'(t) is correlated to the secondary signal portions $n_{\lambda a}$ and $n_{\lambda b}$. Thus, a first segment 28a of the secondary reference signal n'(t) is generally flat, corresponding to the fact that there is very little motion induced noise in the first segments 26a and 27a of each signal. A second segment 28b of the secondary reference signal n'(t) exhibits large excursions, corresponding to the large motion induced excursions in each of the measured signals. A third segment 28c of the noise reference signal n'(t) is generally flat, again corresponding to the lack of motion artifact in the third segments 26c and 27c of each measured signal.

It should also be understood that a reference processor could be utilized in order to obtain the primary reference signal s'(t)=$s_{\lambda a}$-$r_v s_{\lambda b}$(t). The primary reference signal s'(t) would be generally indicative of the plethysmograph waveform.

Figure 29:
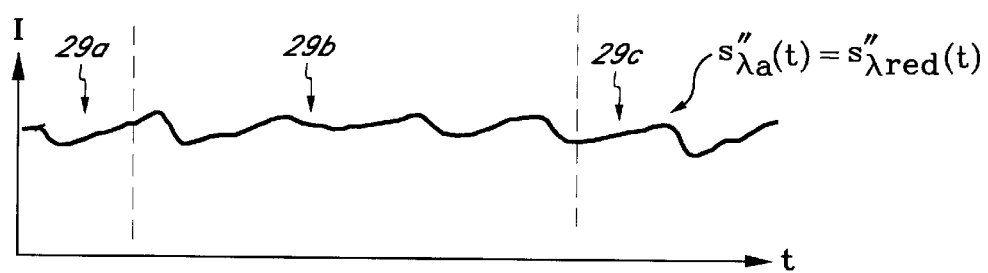
FIG. 29 illustrates a good approximation $s''_{\lambda a}(t)$ to the primary portion $s_{\lambda a}(t)$ of the signal $S_{\lambda a}(t)$ measured at $\lambda a=\lambda red=660$ nm estimated by correlation cancellation with a secondary reference n'(t).
Figure 30:
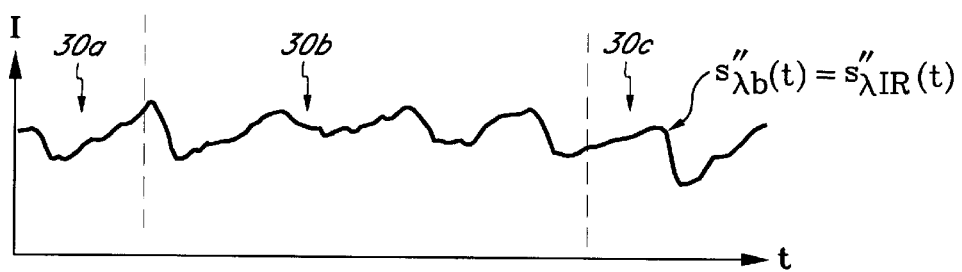
FIG. 30 illustrates a good approximation $s''_{\lambda b}(t)$ to the primary portion $s_{\lambda b}(t)$ of the signal $S_{\lambda b}(t)$ measured at $\lambda b=\lambda IR=910$ nm estimated by correlation cancellation with a secondary reference n'(t).

FIGS. 29 and 30 show the approximations $s''_{\lambda a}(t)$ and $s''_{\lambda b}(t)$ to the primary signals $s_{\lambda a}(t)$ and $s_{\lambda b}(t)$ as estimated by a correlation canceler using a secondary reference signal n'(t). Note that the scale of FIGS. 26 through 30 is not the same for each figure to better illustrate changes in each signal. FIGS. 29 and 30 illustrate the effect of correlation cancellation using the secondary reference signal n'(t) as determined by the reference processor. Segments 29b and 30b are not dominated by motion induced noise as were segments 26b and 27b of the measured signals. Additionally, segments 29a, 30a, 29c, and 30c have not been substantially changed from the measured signal segments 26a, 27a, 26c, and 27c where there was no motion induced noise.

It should be understood that approximation $n''_{\lambda a}(t)$ and $n''_{\lambda b}(t)$ to the secondary signals $n_{\lambda a}(t)$ and $n_{\lambda b}(t)$ as estimated by a correlation canceler using a primary reference signal s'(t) can also be determined in accordance with the present invention.

METHOD FOR ESTIMATING PRIMARY AND SECONDARY SIGNAL PORTIONS OF MEASURED SIGNALS IN A PULSE OXIMETER

Implementing the various embodiments of the correlation canceler described above in software is relatively straightforward given the equations set forth above, and the detailed description above. However, a copy of a computer program subroutine, written in the C programming language, which calculates a primary reference s'(t) using the constant saturation method and, using a joint process estimator 572 which implements a joint process estimator using the equations (54)–(64) is set forth in Appendix B. This joint process estimator estimates a good approximation to the primary signal portions of two measured signals, each having a primary portion which is correlated to the primary reference signal s'(t) and a secondary portion which is correlated to the secondary reference signal n'(t). This subroutine is another way to implement the steps illustrated in the flowchart of FIG. 9 for a monitor particularly adapted for pulse oximetry. The two signals are measured at two different wavelengths λa and λb, where λa is typically in the visible region and λb is typically in the infrared region. For example, in one embodiment of the present invention, tailored specifically to perform pulse oximetry using the constant saturation method, λa=660 nm and λb=940 nm.

The correspondence of the program variables to the variables defined in equations (54)–(64) in the discussion of the joint process estimator is as follows:

$\Delta_m(t)$=nc[m].Delta
$\Gamma_{f,m}(t)$=nc[m].fref
$\Gamma_{b,m}(t)$=nc[m].bref $f_m(t)=nc[m].ferr$
$b_m(t)=nc[m].berr$
$\Im m(t)=nc[m].Fswsqr$
$\beta_m(t)=nc[m].Bswsqr$
$\gamma_m(t)=nc[m].Gamma$
$\rho_{m,\lambda a}(t)=nc[m].Roh\_a$
$\rho_{m,\lambda b}(t)=nc[m].Roh\_b$
$e_{m,\lambda a}(t)=nc[m].err\_a$
$e_{m,\lambda b}(t)=nc[m].err\_b$
$\kappa_{m,\lambda a}(t)=nc[m].K\_a$
$\kappa_{m,\lambda b}(t)=nc[m].K\_b$ A first portion of the program performs the initialization of the registers 90, 92, 96, and 98 and intermediate variable values as in the "INITIALIZED CORRELATION CANCELER" action block 120. A second portion of the program performs the time updates of the delay element variables 110 with the value at the input of each delay element variable 110 is stored in the delay element variable 110 as in the "TIME UPDATE OF LEFT [$Z^{-1}$] ELEMENTS" action block 130. The calculation of saturation is performed in a separate module. Various methods for calculation of the oxygen saturation are known to those skilled in the art. One such calculation is described in the articles by G. A. Mook, et al, and Michael R. Neuman cited above. Once the concentration of oxygenated hemoglobin and deoxygenated hemoglobin are determined, the value of the saturation is determined similarly to equations (72) through (79) wherein measurements at times $t_1$ and $t_2$ are made at different, yet proximate times over which the saturation is relatively constant. For pulse oximetry, the average saturation at time $t=(t_1+t_2)/2$ is then determined by:

$$Sat_{arterial}(t) = \frac{c^A_{HbO2}(t)}{c^A_{HbO2}(t)+c^A_{Hb}(t)} \quad (112a)$$

$$= \frac{\epsilon_{Hb,\lambda a} - \epsilon_{Hb,\lambda b}(\Delta s_{\lambda a}/\Delta s_{\lambda b})}{\epsilon_{HB,\lambda a} - \epsilon_{HbO2,\lambda a} - (\epsilon_{HB,\lambda b} - \epsilon_{HbO2,\lambda b})(\Delta s_{\lambda a}/\Delta s_{\lambda b})} \quad (112b)$$

$$Sat_{venous}(t) = \frac{c^A_{HbO2}(t)}{c^V_{HbO2}(t)+c^V_{Hb}(t)} \quad (113a)$$

$$= \frac{\epsilon_{Hb,\lambda a} - \epsilon_{Hb,\lambda b}(\Delta n_{\lambda a}/\Delta n_{\lambda b})}{\epsilon_{HB,\lambda a} - \epsilon_{HbO2,\lambda a} - \epsilon_{HB,\lambda b} - \epsilon_{HbO2,\lambda b})(\Delta n_{\lambda a}/\Delta n_{\lambda b})} \quad (113b)$$

A third portion of the subroutine calculates the primary reference or secondary reference, as in the "CALCULATE PRIMARY OR SECONDARY REFERENCE (s'(t) or n'(t)) FOR TWO MEASURED SIGNAL SAMPLES" action block 140 for the signals $S_{\lambda a}(t)$ and $S_{\lambda b}(t)$ using the proportionality constants $r_a(t)$ and $r_v(t)$ determined by the constant saturation method as in equation (3). The saturation is calculated in a separate subroutine and a value of $r_a(t)$ or $r_v(t)$ is imported to the present subroutine for estimating either the primary portions $s_{\lambda a}(t)$ and $s_{\lambda b}(t)$ or the secondary portions $n_{\lambda a}(t)$ and $n_{\lambda b}(t)$ of the composite measured signals $S_{\lambda a}(t)$ and $S_{\lambda b}(t)$.

A fourth portion of the program performs Z-stage update as in the "ZERO STAGE UPDATE" action block 150 where the Z-stage forward prediction error $F_o(t)$ and Z-stage backward prediction error $b_o(t)$ are set equal to the value of the reference signal n'(t) or s'(t) just calculated. Additionally zero-stage values of intermediate variables $\Im_o$ and $\beta_0(t)$ (nc[m].Fswsqr and nc[m].Bswsqr in the program) are calculated for use in setting registers 90, 92, 96, and 98 values in the least-squares lattice predictor 70 in the regression filters 80a and 80b.

A fifth portion of the program is an iterative loop wherein the loop counter, M, is reset to zero with a maximum of m=NC_CELLS, as in the "m=0" action block 160 in FIG. 9. NC_CELLS is a predetermined maximum value of iterations for the loop. A typical value for NC_CELLS is between 6 and 10, for example. The conditions of the loop are set such that the loop iterates a minimum of five times and continues to iterate until a test for conversion is met or m-NC_CELLS. The test for conversion is whether or not the sum of the weighted sum of four prediction errors plus the weighted sum of backward prediction errors is less than a small number, typically 0.00001 (i.e., $\Im_m(t)+\beta_m(t) \leq 0.00001$).

A sixth portion of the program calculates the forward and backward reflection coefficient $\Gamma_{m,f}(t)$ and $\Gamma_{m,b}(t)$ register 90 and 92 values (nc[m].fref and nc[m].bref in the program) as in the "ORDER UPDATE $m^{th}$-STAGE OF LSL-PREDICTOR" action block 170. Then forward and backward prediction errors $f_m(t)$ and $b_m(t)$ (nc[m].ferr and nc[m].berr in the program) are calculated. Additionally, intermediate variables $\Im_m(t)$, $\beta m(t)$, and $\gamma(t)$ (nc[m].Fswsqr, nc[m].Bswsqr, nc[m].gamma in the program) are calculated. The first cycle of the loop uses the value for nc[0].Fswsqr and nc[0].Bswsqr calculated in the ZERO STAGE UPDATE portion of the program.

A seventh portion of the program, still within the loop begun in the fifth portion of the program, calculates the regression coefficient register 96 and 98 values $\kappa_{m,\lambda a}(t)$ and $\kappa_{m,\lambda b}(t)$ (nc[m].K_a and nc[m].K_b in the program) in both regression filters, as in the "ORDER UPDATE $m^{th}$ STAGE OF REGRESSION FILTER(S)" action block 180. Intermediate error signals and variables $e_{m,\lambda a}(t)$, $e_{m,\lambda b}(t)$, $\rho_{m,\lambda a}(t)$, and $\rho_{m,\lambda b}(t)$ (nc[m].err_a and nc[m].err_b, nc[m].roh_a, and nc[m].roh_b in the subroutine) are also calculated.

The loop iterates until the test for convergence is passed. The test for convergence of the joint process estimator is performed each time the loop iterates analogously to the "DONE" action block 190. If the sum of the weighted sums of the forward and backward prediction errors $\Im_m(t)+\beta m(t)$ is less than or equal to 0.00001, the loop terminates. Otherwise, sixth and seventh portions of the program repeat.

The output of the present subroutine is a good approximation to the primary signals $s"_{\lambda a}(t)$ and $s"_{\lambda b}(t)$ or the secondary signals $n"_{\lambda a}(t)$ and $n"_{\lambda b}(t)$ for the set of samples $S_{\lambda a}(t)$ and $S_{\lambda b}(t)$ input to the program. After approximations to the primary signal portions or the secondary signals portions of many sets of measured signal samples are estimated by the joint process estimator, a compilation of the outputs provides waves which are good approximations to the plethysmographic wave or motion artifact at each wavelength, $\lambda a$ and $\lambda b$.

It should be understood that the subroutine of Appendix B is merely one embodiment which implements the equations (54)–(64). Although implementation of the normalized and QRD-LSL equations is also straightforward, a subroutine for the normalized equations is attached as Appendix C, and a subroutine for the QRD-LSL algorithm is attached as Appendix D.

While one embodiment of a physiological monitor incorporating a processor of the present invention for determining a reference signal for use in a correlation canceler, such as an adaptive noise canceler, to remove or derive primary and secondary components from a physiological measurement has been described in the form of a pulse oximeter, it will be obvious to one skilled in the art that other types of physiological monitors may also employ the above described techniques.

Furthermore, the signal processing techniques described in the present invention may be used to compute the arterial and venous blood oxygen saturations of a physiological system on a continuous or nearly continuous time basis. These calculations may be performed, regardless of whether or not the physiological system undergoes voluntary motion.

Furthermore, it will be understood that transformations of measured signals other than logarithmic conversion and determination of a proportionality factor which allows removal or derivation of the primary or secondary signal portions for determination of a reference signal are possible. Additionally, although the proportionality factor r has been described herein as a ratio of a portion of a first signal to a portion of a second signal, a similar proportionality constant determined as a ratio of a portion of a second signal to a portion of a first signal could equally well be utilized in the processor of the present invention. In the latter case, a secondary reference signal would generally resemble $n'(t) = n_{\lambda b}(t) - rn_{\lambda a}(t)$.

Furthermore, it will be understood that correlation cancellation techniques other than joint process estimation may be used together with the reference signals of the present invention. These may include but are not limited to least mean square algorithms, wavelet transforms, spectral estimation techniques, neural networks, Weiner and Kalman filters among others.

One skilled in the art will realize that many different types of physiological monitors may employ the teachings of the present invention. Other types of physiological monitors include, but are in not limited to, electro cardiographs, blood pressure monitors, blood constituent monitors (other than oxygen saturation) monitors, capnographs, heart rate monitors, respiration monitors, or depth of anesthesia monitors. Additionally, monitors which measure the pressure and quantity of a substance within the body such as a breathalizer, a drug monitor, a cholesterol monitor, a glucose monitor, a carbon dioxide monitor, a glucose monitor, or a carbon monoxide monitor may also employ the above described techniques.

Figure 31:
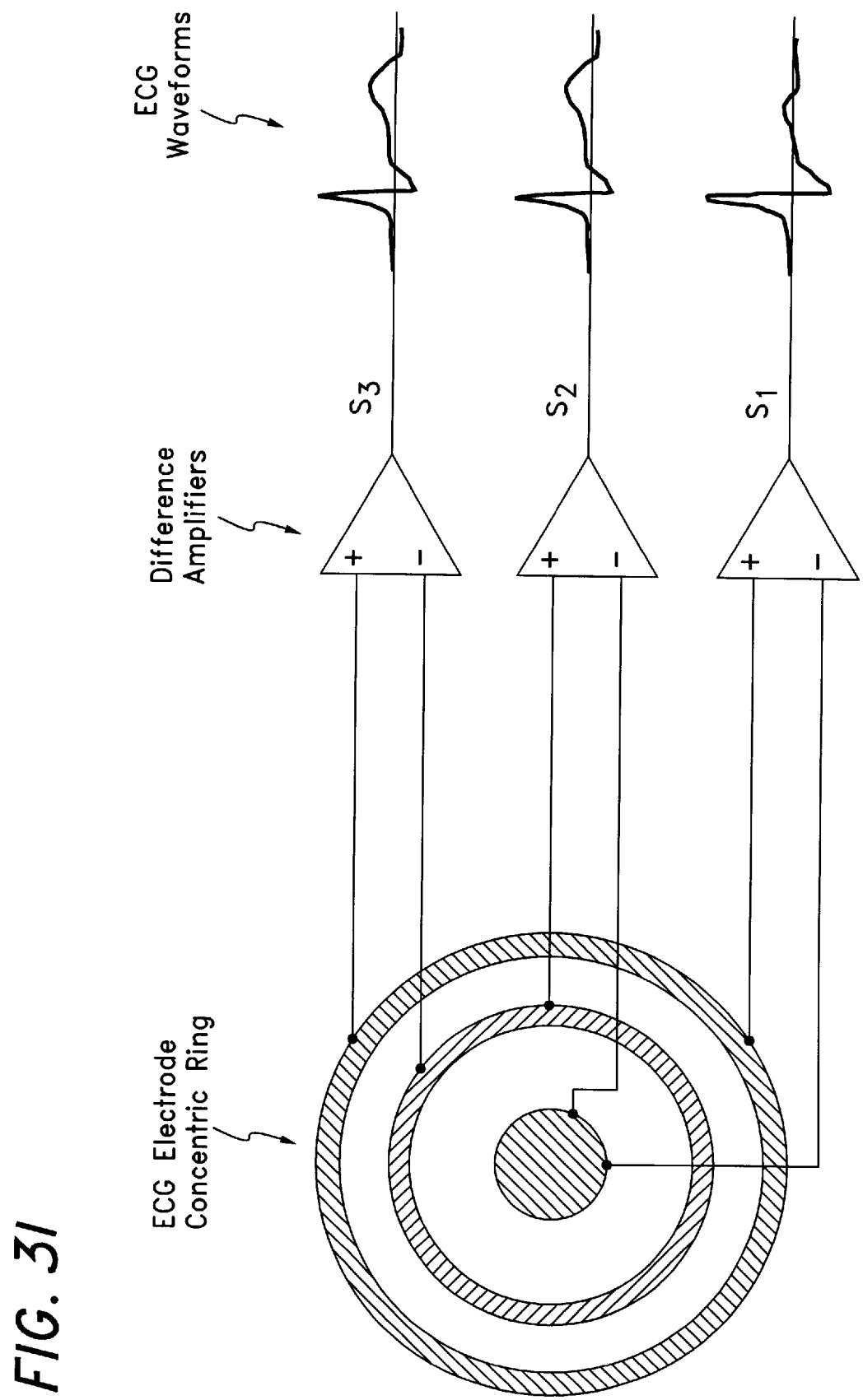
FIG. 31 depicts a set of 3 concentric electrodes, i.e., a tripolar electrode sensor, to derive electrocardiography (ECG) signals, denoted as $S_1$, $S_2$ and $S_3$, for use with the present invention. Each of the ECG signals contains a primary portion and a secondary portion.

Furthermore, one skilled in the art will realize that the above described techniques of primary or secondary signal removal or derivation from a composite signal including both primary and secondary components can also be performed on electrocardiography (ECG) signals which are derived from positions on the body which are close and highly correlated to each other. It should be understood that a tripolar Laplacian electrode sensor such as that depicted in FIG. 31 which is a modification of a bipolar Laplacian electrode sensor discussed in the article "Body Surface Laplacian ECG Mapping" by Bin He and Richard J. Cohen contained in the journal IEEE Transactions on Biomedical Engineering, Vol. 39, No. 11, November 1992 could be used as an ECG sensor. It must also be understood that there are a myriad of possible ECG sensor geometry's that may be used to satisfy the requirements of the present invention. The same type of sensor could also be used for EEG and EMG measurements.

Furthermore, one skilled in the art will realize that the above described techniques can also be performed on signals made up of reflected energy, rather than transmitted energy. One skilled in the art will also realize that a primary or secondary portion of a measured signal of any type of energy, including but not limited to sound energy, X-ray energy, gamma ray energy, or light energy can be estimated by the techniques described above. Thus, one skilled in the art will realize that the techniques of the present invention can be applied in such monitors as those using ultrasound where a signal is transmitted through a portion of the body and reflected back from within the body back through this portion of the body. Additionally, monitors such as echo cardiographs may also utilize the techniques of the present invention since they too rely on transmission and reflection.

While the present invention has been described in terms of a physiological monitor, one skilled in the art will realize that the signal processing techniques of the present invention can be applied in many areas, including but not limited to the processing of a physiological signal. The present invention may be applied in any situation where a signal processor comprising a detector receives a first signal which includes a first primary signal portion and a first secondary signal portion and a second signal which includes a second primary signal portion and a second secondary signal portion. Thus, the signal processor of the present invention is readily applicable to numerous signal processing areas.

APPENDIX A

DIGITAL SIGNAL PROCESSING WITH EFFICIENT POLYPHASE RECURSIVE ALL-PASS FILTERS fred harris[*], Maximilien d'Oreye de Lantremange[*], and A.G. Constantinides[**]

[*] Department of Electrical and Computer Engineering, San Diego State University, San Diego, California 92182-0190, USA.
[**] Signal Processing Section, Department of Electrical Engineering, Imperial College of Science, Technology and Medicine, Exhibition Road, London SW7-2BT, England.

ABSTRACT: Digital filters can be realized with remarkably small computational burden as polyphase recursive all-pass networks. These networks are formed as a sum of M parallel all-pass subfilters with phase shifts selected to add constructively in the passband and destructively in the stopband. The design technique we present here starts with prototype M-path recursive all-pass filters obtained by a new optimizing algorithm (described in detail elsewhere). These filters are operated with combinations of all-pass transformations, resampling, and cascading options. We demonstrate a number of designs using the new algorithm along with examples of filtering systems obtained by the techniques presented.

1. INTRODUCTION

A standard finite impulse response (FIR) filter can be modeled, as indicated in Fig. 1, as the weighted summation of the contents of a tapped delay line. This summation is shown in (1) and the transfer function of this filter is shown in (2).

$$y(n) = \sum_{m=0}^{M-1} h(m-n)\, x(m) \qquad (1)$$

$$Y(Z) = X(Z) \sum_{n=0}^{M-1} h(n)\, z^{-n} \qquad (2)$$

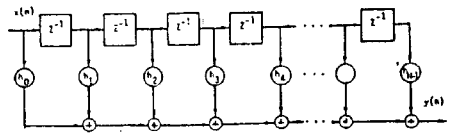

FIGURE 1. TAPPED DELAY LINE FIR FILTER

Figure 2:
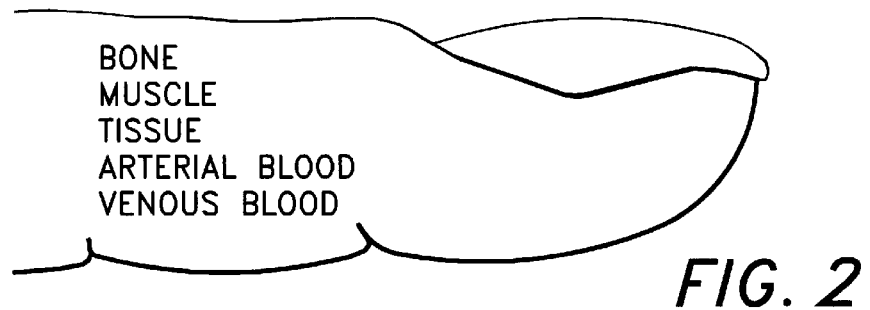
FIG. 2 schematically illustrates a typical finger.

We note the frequency selective characteristics of the filter output is due to the phase shift between successive samples in the tapped delay line. This phaser summation is shown in Fig. 2 for two different frequencies.

Note that it is the phase shift, and not the weighting terms which is responsible for the frequency dependent gain of the filter. The weighting terms are used primarily to control passband width and stopband attenuation of the filter. An idea derived from spatial beamforming (known as beam spoiling) [1] and from signal synthesis (peak-to-rms control) [2] is to use structured phase shifts (with arbitrary amplitudes) to accomplish the same goal.

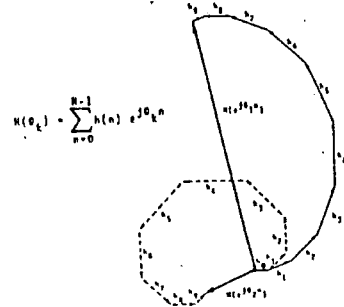

FIGURE 2. PHASOR SUMMATION OF FIR FILTER OUTPUT FOR TWO FREQUENCIES

Figure 3:
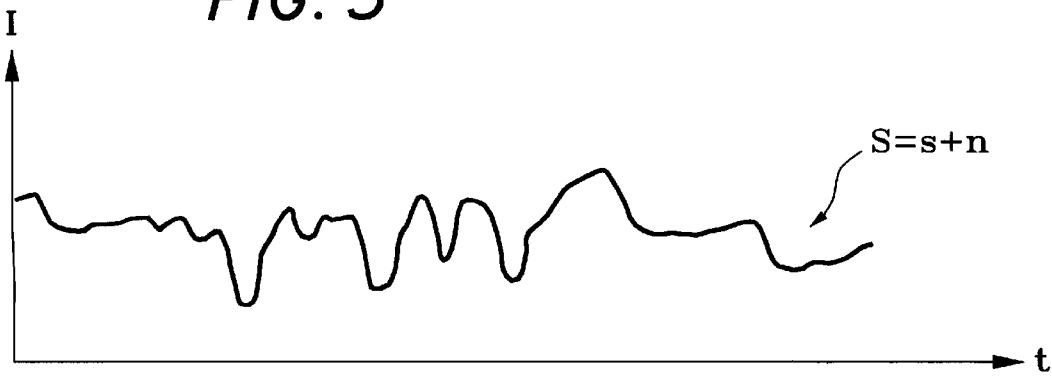
FIG. 3 illustrates a plethysmographic waveform which includes a motion-induced erratic signal portion.

The class of filters we describe here replaces the weights of the FIR filter with all-pass subfilters which exhibit unity gain with frequency dependent phase shift. In anticipation of the polyphase structure, the all-pass subfilters are, as shown in (3) and Fig. 3, first order polynomials in $z^{-N}$ where M is the number of taps in the structure. This composite form is indicated in Fig. 4a with a modified form reflecting a polyphase structure in 4b. The transfer function of this structure is shown in (4).

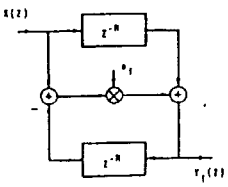

FIGURE 3. M-TH ORDER ALL-PASS SUBFILTER

Presented at International Conference on Signal Processing
Florence, Italy, Sept. 4-6 1991.

Fig. 7 show examples of equal ripple designs obtained from this new algorithm for a 2-path and for a 5-path filter with two and three all-pass stages per path respectively. Interacting constraints on the optimal design (described in the aforementioned paper) limit the possible number of stages per path for the 5-path filter to the sequences (1,1,1,1,0), (2,2,2,1,1), (3,3,2,2,2), etc., so that the optimum 5-path filter uses three less stages than allocated to the design. Similarly the 2-path filter is limited to the sequences (1,0), (1,1), (2,1), (2,2), (2,3), (3,3), etc.

2. TWO PATH FILTERS

We find a wealth of interesting properties and clever applications for this structure even if we limit our discussion to a 2-path filter. As designed, the 2-path filter is a half bandwidth filter with the 3-dB bandwidth at $0.25\ f_s$. If the zeros are restricted to the half sampling frequency, the filter identical to a half bandwidth Butterworth obtained by the standard warped bilinear transform. For this special case, the real parts of the root locations go to zero. If the zeros are optimized for equal ripple stop band behavior the filter becomes a constrained Elliptic filter. The constraints are related to a property of complementary all-pass filters. We define the all-pass sections for the 2-path filter as $H_0(\theta)$ and $H_1(\theta)$ and, as indicated in Fig. 8, the scaled by one-half sum and difference of these paths by $A(\theta)$ and $B(\theta)$, the lowpass and highpass filters, respectively. We know that the all-pass sections satisfy (5) from which we derive the power relationship between the lowpass and highpass filters shown in (6).

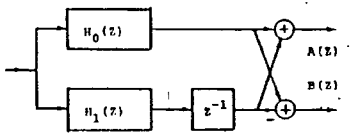

FIGURE 8. COMPLEMENTARY LOWPASS AND HIGHPASS FILTERS FROM 2-PATH ALL-PASS NETWORK $$|H_0(\theta)|^2 = |H_1(\theta)|^2 = 1 \quad (5)$$

$$|A(\theta)|^2 + |B(\theta)|^2 = |0.5[H_0(\theta)+H_1(\theta)]|^2 \quad (6a)$$

$$+ |0.5[H_0(\theta)-H_1(\theta)]|^2$$

$$= 0.5[|H_0(\theta)|^2 + |H_1(\theta)|^2] \quad (6b)$$

$$= 1 \quad (6c)$$

Now to interpret how this relationship impacts the 2-path filter. For the complementary filters we define the minimum passband gain of by $1-\epsilon_1$ and the peak stopband gain by $\epsilon_2$. Substituting these gains in (6) we obtain (7).

$$(1-\epsilon_1)^2 + (\epsilon_2)^2 = 1 \quad (7a)$$

$$(1-\epsilon_1)^2 = 1 - (\epsilon_2)^2 \quad (7b)$$

$$1 - 2\epsilon_1 + (\epsilon_1)^2 = 1 - (\epsilon_2)^2 \quad (7c)$$

For small $\epsilon_1$, we can ignore $(\epsilon_1)^2$ which leads to (8).

$$\epsilon_1 = 0.5\ (\epsilon_2)^2 \quad (8)$$

Thus if the stopband attenuation is selected to be 0.001 (60.0 dB), the passband ripple is 0.000 000 5 (126.0 dB) or the passband minimum gain is 0.999 999 5 (-0.000 000 22 dB). As can be seen these filters have a remarkably flat passband. We conclude that the 2-path equal ripple stopband filters are elliptic filters with coupled passband and stopband ripple with -3.0 dB gain at $0.25\ f_s$. There are two significant differences between the 2-path and the standard implementation of the equivalent elliptic filter. The first is a four-to-one savings in multiplications; a fifth order half bandwidth 2-path filter requires only two coefficients as opposed to the direct implementation which requires eight (scaling included). The second is that all-pass structures exhibit unity gain to internal states hence do not require extended precision registers to store internal states as do standard implementations.

As with any filter design, the transition bandwidth can be traded for out of band attenuation for a fixed order or transition bandwidth can be steepened for a fixed attenuation by increasing filter order. While nomographs exist for the elliptic and Butterworth filters which can be implemented by the 2-path structure, a simple approximate relationship for the equal ripple filter is given in (9), where A(dB) is attenuation in dB, $\Delta f$ is transition bandwidth, and N is the total number of all-pass segments in the filter.

$$A(dB) = (72\ \Delta f + 10)\ N \quad (9)$$

2A. HILBERT TRANSFORM FILTERS

The Hilbert Transform (HT) can be thought of as a particular type of half band filter. It is modelled and implemented by a wide band 90° phase shifting network. The HT is often used in DSP applications to form the analytic signal a(n) as shown in (10), a signal with spectra limited to the positive (or negative) frequency band.

$$a(n) = x(n) + j\ \hat{x}(n) \quad (10)$$

We can cast the 2-path filter as a HT in a number of ways but a simple method, akin to the transformation performed on a half band FIR filter [4], is a heterodyne of the half band filter to the quarter sample frequency. If the original filter response and transform are denoted by h(n) and H(Z) respectively, then the heterodyned expressions can be easily seen to be those in (11).

$$h(n) \Rightarrow h(n)\ e^{jn\pi/2} = h(n)\ (j)^n \quad (11a)$$

$$H(Z) \Rightarrow H(Z\ e^{j\pi/2}) = H(j\ Z) \quad (11b)$$

The transformation of a half band filter to an HT filter is accomplished by replacing each $Z^{-1}$ of the transfer function with $-jZ^{-1}$. Since the polynomials of the all-pass subfilters are second order, this transformation can be accomplished by changing the sign of the coefficient used in each all-pass sub filter and by associating a -j with the lower path delay. These operations are indicated in Fig. 9.

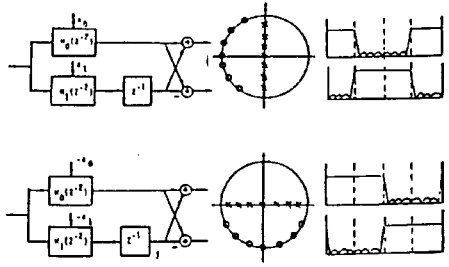

FIGURE 9. HILBERT TRANSFORM ALL-PASS FILTER REALIZATION AS TRANSFORMED HALF BAND FILTER

2B. INTERPOLATION AND DECIMATION FILTERS

Any half bandwidth filter can be used to perform 2-to-1 resampling (up or down, popularly identified as interpolation and decimation). Finite impulse response (FIR) filters can be operated with a polyphase partition which does not process inserted zero input points (up-sampling) or compute the discarded output points (down sampling). While this option is not available for the general recursive filter, it is an option for the recursive all-pass M-path filter. The M-path filter can be partitioned into polyphase segments because of the interaction of the internal delays of the M-th order subfilters and the delay line of each path. This relationship is particularly easy to see for the 2-path filter. An impulse applied at index $n_0$ makes a contribution to the output at the same time via the upper path while an output is not available from the lower path till the next index due to its extra delay $z^{-1}$. During that same next index, the upper path offers no contribution to the output because there is no $z^{-1}$ path associated with its $z^{-2}$ polynomial. Thus the filter delivers successive samples of its impulse response from alternate paths of the filter.

Down sampling is accomplished by delivering alternate input samples to each path of the filter operating at the reduced input rate. Since the delay of the second path is accomplished by the input commutation the physical delay element in that path is removed. The filtered and down sampled output is generated by the sum or difference of the two path responses. Note that the computation rate per input sample point is half that of the non resampled filter, thus if the 2-path filter of Fig. 7 is used for down sampling we would perform 3 multiplications per input point.

Up sampling is accomplished by reversing the down sampling process. This entails delivering the same input to the two paths and commutating between their outputs. Both forms of resampling are shown in Fig. 10. As in the previous example, when the 2-path filter of Fig. 7. is used for up sampling we would perform 3 multiplications per output point.

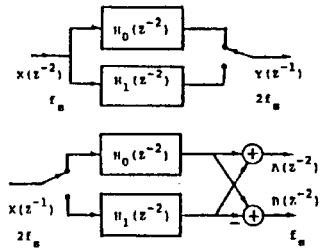

FIGURE 10. RESAMPLING 2-PATH ALL-PASS FILTER

The cascade operation of down sampling and up sampling of the complementary outputs performs two band maximally decimated quadrature mirror filtering and reconstruction [5].

Cascading multiple stages of up sampling or down sampling filters can achieve high order sample rate change with remarkably small workload per data point. For instance, a 1-to-16 up sampler with 96 dB dynamic range for a signal with cutoff frequency of 0.4 $f_s$ requires 2-path filters with successively smaller number of all-pass stages of orders (3,3), (2,2), (2,1), and (1,1). This requires a total of 42 multiplications for 16 outputs, for an average workload of approximately 2.7 operations per output point.

2C. ITERATED POLYPHASE ALL-PASS FILTERS

The all-pass networks described earlier are formed by polynomials in $Z^{-K}$ and specifically for the 2-path filters $Z^{-2}$. A useful transformation is to replace each $Z^{-2}$ with $Z^{-2K}$, to obtain higher order filters exhibiting K-fold spectral replication of the original filter. For K=2, the half band filter centered at DC becomes a pair of quarter band filters centered at DC and $f_s/2$. An example of spectral replication for the iterated filter is shown in Fig. 11.

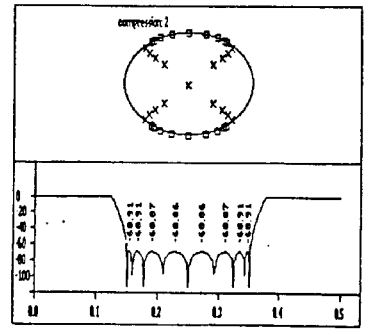

FIGURE 11. SPECTRUM OF ITERATED 2-PATH FILTER: POLYNOMIALS IN $Z^{-4}$

Note that this transformation scales the prototype filter's spectrum by 1/K, reducing both passband width and transition width. Thus very steep transition bandwidths and narrow filters can be realized by the use of low order polynomials of degree 2K obtained via delay elements. Energy in the replicated spectral regions can be removed by a sequence of filters incorporating various degrees of resampling and iterated filters of reduced degree.

3. EFFICIENT ALL-PASS FILTER BANKS.

Efficient spectral partitioning can be obtained by cascading and resampling the outputs of iterated lowpass and HT filters. For instance the spectra of a four channel filter bank centered on the four quadrants can be formed with a complementary half band filter followed by a pair of resampled HT filters as shown on the left side of Fig. 12. The workload for this 70 dB attenuation filter set is 3 multiplications per output channel.

A four channel filter bank straddling the previous set (ie. centered on the four cardinal directions) can be formed with an iterated by two complementary half band filter followed by both a complementary half band resampled filter and a resampled HT filter. This spectra of this filter set is shown on the right side of Fig. 12. The workload for this 70 dB attenuation filter set is 2 multiplications per output channel.

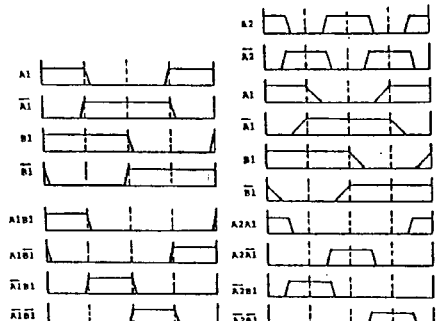

FIGURE 12. SPECTRA OF FOUR CHANNEL QUADRANT CENTERED AND CARDINAL CENTERED FILTER BANK

4. OTHER ALL-PASS TRANSFORMATIONS

The prototype complementary all-pass filter set can also be transformed to filters of arbitrary bandwidth and of arbitrary center frequency by standard all-pass transformations [6]. The lowpass transformation for the half band filter is shown in (12).

$$z^{-1} \Rightarrow \frac{b + z^{-1}}{1 + b z^{-1}}, \quad b = \frac{1-\tan(\theta_0/2)}{1+\tan(\theta_0/2)} \quad (12)$$

This transformation warps the frequency variable of the filter so that the -3 dB point resides at frequency $\theta_0$. When $\theta_0$ is different from $\pi/2$ the second order polynomials of the all-pass subfilters acquire coefficients for the $z^{-1}$ term. The resulting filter requires two multiplications per pole zero pair which is still half the workload of the traditional canonic forms. In addition, the pole at the origin (due to the delay of the second path) transforms to a first order all-pass filter thus converting an inactive pole to an active one requiring an additional first order stage. Fig. 13 presents the frequency warped version of the filter presented in Fig. 7a. Both this filter and its complement are available from the warped structure.

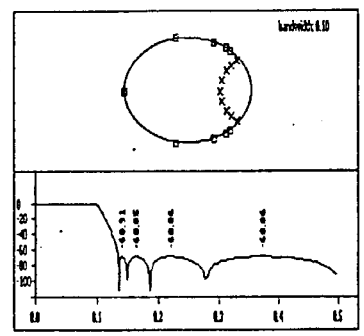

FIGURE 13. LOWPASS TRANSFORMATION OF ALL-PASS FILTER

The bandpass transformation is presented in (13).

$$z^{-1} \Rightarrow -z^{-1} \frac{c - z^{-1}}{1 - c z^{-1}} \quad c = \cos(\theta_1) \quad (13)$$

This transformation warps the frequency variable of the filter so that the center frequency resides at frequency $\theta_1$. If $\theta_1$ is equal to 0.0 this transformation is equivalent to the iterated transformation described in 2.C. For any other frequency, this transformation converts the second order all-pass filters to fourth order all-pass structures. This requires four multiplications to form four pole-zero pairs of the resultant filter which is still half the workload of the traditional canonic forms. In addition, the transformation converts the real pole (which is an image of the pole originally at the origin) to a pair of complex poles requiring a second order all-pass stage. Fig. 14 presents the frequency warped version of the filter presented in Fig. 14. As earlier, both this filter and its complement are available from the warped structure.

Other transformations and geometries [7] can be used with the digital all-pass structure and the reader is directed to the bibliography of the listed papers for a profusion of options.

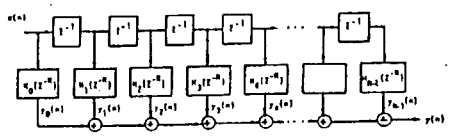

FIGURE 4A. ALL-PASS FILTER STRUCTURE

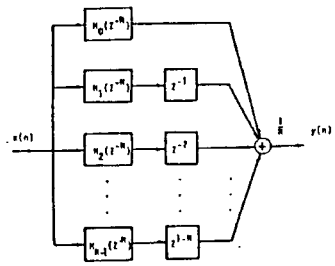

FIGURE 4B. POLYPHASE ALL-PASS STRUCTURE $$H_n(Z^{-M}) = \frac{a_n + Z^{-M}}{1 + a_n Z^{-M}} \quad (3)$$

$$Y(Z) = X(Z) \sum_{n=0}^{M-1} H_n(Z^{-M}) Z^{-n} \quad (4)$$

The roots of (3), the M-th roots of $-a_n$ and its reciprocal, are equally spaced about the origin as shown in Fig. 5 for the indicated degrees M. Note that we realize M poles and M zeros per multiplication in the all-pass stage. This means for instance that a 2-path filter offers two poles and two zeros per multiplication as opposed to one pole (or zero) per multiplication for the standard (factored or unfactored) canonic forms.

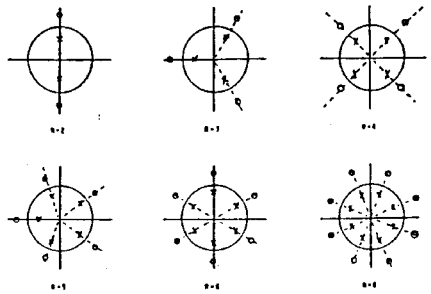

FIGURE 5. POLE-ZERO DISTRIBUTION FOR M-TH ORDER ALL-PASS SUBFILTERS

As we go around the unit circle we visualize that the all-pass subfilters exhibit rapid change in phase in the neighborhood of each pole-zero pair. By proper choice of the pole positions, the phase shift of each leg of the M path filter can be made to match or to differ by multiples of $2\pi/M$ over selected spectral intervals. This is suggested in Fig. 6 for M=2 and M=4. The coefficients of the all-pass subfilters can be determined by standard algorithms [3] or by a new algorithm developed by harris and d'Oreye and reported in a paper recently submitted for publication (Signal Processing).

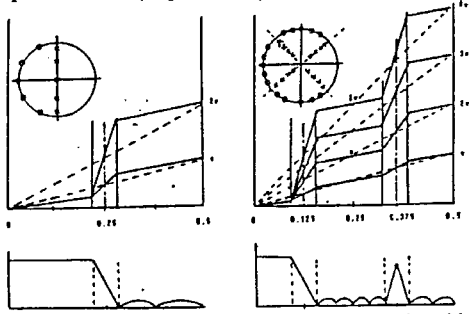

FIGURE 6. TYPICAL PHASE RESPONSES OF ALL-PASS FILTER PATHS, AND CORRESPONDING MAGNITUDE RESPONSES.

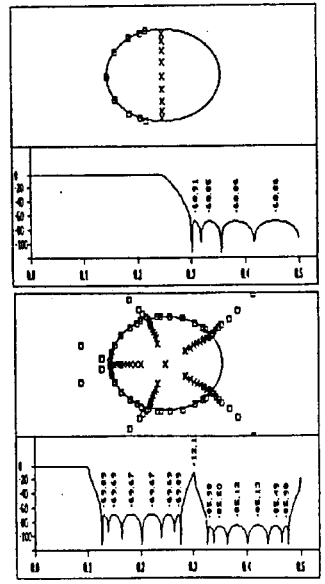

FIGURE 7. POLE-ZERO PLOT AND MAGNITUDE RESPONSE FOR 2-PATH AND 5-PATH POLYPHASE ALL-PASS NETWORK

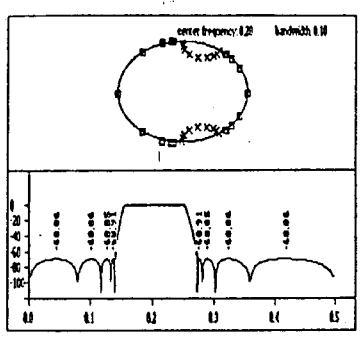

FIGURE 14. BANDPASS TRANSFORMATION OF ALL-PASS FILTER

5. CONCLUSIONS

We have reviewed the form and utility of the all-pass polyphase filter structure. We then presented a number of all-pass transformations which could be easily applied to M-path all-pass filter sets. The emphasis has been on 2-path networks but the material is easily extended to arbitrary M. We alluded to a new set of algorithms for designing M-path filters which will be reported in an upcoming Signal Processing paper. We have demonstrated capabilities of this algorithm by using it to generate the examples presented in this paper.

The primary advantage of these structures is very low workload for a given filtering task. Other papers [8,9,10] have discussed the low sensitivity to finite arithmetic exhibited by these filters. The primary impediment to the use of these filters is their newness and the lack of available design methods for computing filter weights. This paper (along with excellent surveys listen in the bibliography) address the first problem and a forthcoming paper addresses the second.

6. ACKNOWLEDGEMENT

This work was sponsored in part by the Industry/University Cooperative Research Center (I/UCRC) on Integrated Circuits and Systems (ICAS) at San Diego State University (SDSU) and the University of California, San Diego (UCSD).

7. BIBLIOGRAPHY

1. Private correspondence between f.j. harris and Stan Acks of Hughes Aircraft, Radar Systems Group, El Segundo, CA. 1983.

2. M.R. Schroeder, "Number Theory in Science and Communications", Springer-Verlag, 1984, Chapter 28, Waveforms and Radiation Patterns, pp. 278-288.

3. R.A. Valenzuela and A.G. Constantinides, "Digital Signal Processing Schemes for Efficient Interpolation and Decimation", IEE Proceedings, Vol. 130, Pt. G. No. 6, Dec. 1983, pp. 225-235.

4. D. Elliot, "Handbook of Digital Signal Processing, Engineering Applications", Academic Press, 1987, Chapter 3, pp. 227-233.

5. Phillip A. Regalia, Sanjit K. Mitra, and P.P. Vaidyanathan, "The Digital All-Pass Filter: A Versatile Signal Processing Building Block", Proc. of IEEE, Vol. 76, No. 1, Jan. 1988, pp. 19-37.

6. A.G. Constantinides, "Spectral Transformations for Digital Filters", Proc. IEE, Vol. 117, No. 8, Aug. 1970, pp. 1585-1590.

7. S.K. Mitra, K. Hirano, S. Nishimura, and K. Sugahara, "Design of Digital Bandpass-/Bandstop Filters with Independent Tuning Characteristics", FREQUENZ, 44(1990)3-4, pp. 117-121.

8. R. Ansari and B. Liu, "A Class of Low-Noise Computationally Efficient Recursive Digital Filters with Applications to Sampling Rate Alterations", IEEE Trans. Acoust., Speech, Signal Processing, Vol. ASSP-33, No. 1. Feb. 1985, pp. 90-97.

9. H. Samueli, "A Low-Complexity Multiplierless Half-Band Recursive Digital Filter Design", IEEE Trans. Acoust., Speech, Signal Processing, Vol. ASSP-37, No. 3. Mar. 1989, pp. 442-444.

10. P.P. Vaidyanathan and Zinnur Doganata, "The Role of Lossless Systems in Modern Digital Signal Processing: A Tutorial", IEEE Trans. on Education, Vol. 32, No. 3, Aug. 1989, pp. 181-197.

```
/*************************************************************
 ************************* APPENDIX B *************************
 ************************* Least Square Lattice ***************
 ************************* Noise Cancelling *******************
/* Example for ratiometric approach to noise cancelling */
define LAMBDA  0.95 void OxiLSL_NC( int      reset,
                int      passes,
                int      *signal_1,
                int      *signal_2,
                int      *signal_3,
                int      *target_1,
                int      *target_2) { int     i, ii, k, m, n, contraction;
static  int     *s_a, *s_b, *s_c, *out_a, *out_c;
static  float   Delta_sqr, scale, noise_ref;

if( reset == TRUE){
   s_a   = signal_1;
   s_b   = signal_2;
   s_c   = signal_3;
   out_a = target_1;
   out_c = target_2;
   factor = 1.5;
   scale = 1.0 /4160.0;

/* noise canceller initialization at time t=0 */ nc[0].berr  = 0.0;
   nc[0].Gamma = 1.0;

for(m=0; m<NC_CELLS; m++) {
      nc[m].err_a  = 0.0;
      nc[m].err_b  = 0.0;
      nc[m].Roh_a  = 0.0;
      nc[m].Roh_c  = 0.0;
      nc[m].Delta  = 0.0;
      nc[m].Fswsqr = 0.00001;
      nc[m].Bswsqr = 0.00001;
   }
}
/*===================== END INITIALIZATION =====================*/
for(k=0; k<passes; k++){ contraction = FALSE;
   for(m=0; m< NC_CELLS; m++) {       /* Update delay elements    */
      nc[m].berr1   = nc[m].berr;
      nc[m].Bswsqr1 = nc[m].Bswsqr;
   } noise_ref   = factor * log(1.0 - (*s_a) * scale)
                        - log(1.0 - (*s_b) * scale) ;
   nc[0].err_a = log(1.0 - (*s_b) * scale);
   nc[0].err_b = log(1.0 - (*s_c) * scale);
```

```
++s_a;
++s_b;
++s_c;

nc[0].ferr   = noise_ref ;
nc[0].berr   = noise_ref ;
nc[0].Fswsqr = LAMBDA * nc[0].Fswsqr + noise_ref * noise_ref;
nc[0].Bswsqr = nc[0].Fswsqr;

/* Order Update      */
for(n=1;( n < NC_CELLS) && (contraction == FALSE); n++) {

/* Adaptive Lattice Section */ m = n-1;
  ii= n-1;

nc[m].Delta *=  LAMBDA;
  nc[m].Delta +=  nc[m].berr1 * nc[m].ferr  / nc[m].Gamma ;
  Delta_sqr    =  nc[m].Delta * nc[m].Delta;

nc[n].fref   = -nc[m].Delta / nc[m].Bswsqr1;
  nc[n].bref   = -nc[m].Delta / nc[m].Fswsqr;

nc[n].ferr   = nc[m].ferr  + nc[n].fref * nc[m].berr1;
  nc[n].berr   = nc[m].berr1 + nc[n].bref * nc[m].ferr;

nc[n].Fswsqr = nc[m].Fswsqr  - Delta_sqr / nc[m].Bswsqr1;
  nc[n].Bswsqr = nc[m].Bswsqr1 - Delta_sqr / nc[m].Fswsqr;

if( (nc[n].Fswsqr + nc[n].Bswsqr) > 0.00001 || (n < 5) ) {
    nc[n].Gamma = nc[m].Gamma - nc[m].berr1 * nc[m].berr1 / nc[m].Bswsqr1;
    if(nc[n].Gamma < 0.05) nc[n].Gamma = 0.05;
    if(nc[n].Gamma > 1.00) nc[n].Gamma = 1.00;

/* Joint Process Estimation Section */ nc[m].Roh_a *= LAMBDA;
    nc[m].Roh_a += nc[m].berr * nc[m].err_a  / nc[m].Gamma ;
    nc[m].k_a    = nc[m].Roh_a / nc[m].Bswsqr;
    nc[n].err_a  = nc[m].err_a - nc[m].k_a * nc[m].berr;

nc[m].Roh_c *= LAMBDA;
    nc[m].Roh_c += nc[m].berr * nc[m].err_b  / nc[m].Gamma ;
    nc[m].k_c    = nc[m].Roh_c / nc[m].Bswsqr;
    nc[n].err_b  = nc[m].err_b - nc[m].k_c * nc[m].berr;

}
  else {
    contraction = TRUE;
    for(i=n; i<NC_CELLS; i++) {
      nc[i].err_a   = 0.0;
      nc[i].Roh_a   = 0.0;
      nc[i].err_b   = 0.0;
      nc[i].Roh_c   = 0.0;
      nc[i].Delta   = 0.0;
      nc[i].Fswsqr  = 0.00001;
      nc[i].Bswsqr  = 0.00001;
      nc[i].Bswsqr1 = 0.00001;
```

```
            }
        }
    }

*out_a++ = (int)( (-exp(nc[ii].err_a) +1.0) / scale) ;
    *out_c++ = (int)( (-exp(nc[ii].err_b) +1.0) / scale) ;

}
}
/*********************       Least Square Lattice      ****************************
****************************                          ****************************
*********************************************************************************/
```

APPENDIX C

/* Normalized Adaptive Noise Canceler  */

```c
#include <stdlib.h>
include <math.h> define TRUE            1
define FALSE           0 define FLOAT32         float
define INT32           long int
define VOID            void define FABSF           fabs
define SQRTF           sqrt define MAX(a,b)  (a) > (b) ? (a) : (b)
define MIN(a,b)  (a) < (b) ? (a) : (b)

#define MIN_VAL     0.01
#define MAX_DEL     0.999999
#define MIN_DEL     -0.999999
#define MAX_RHO     2.0
#define MIN_RHO     -2.0
define MIN_BSERR   1E-15 typedef struct {
    FLOAT32     berr;
    FLOAT32     berr_1;
    FLOAT32     delta;
    FLOAT32     err;
    FLOAT32     ferr;
    FLOAT32     gamma;
    FLOAT32     gamma_1;
    FLOAT32     rho;
    FLOAT32     delta_1;
    FLOAT32     Bserr;
    FLOAT32     Bserr_1;
} LANC_CELLS;

typedef struct {
    INT32       cc;                 /* number of cells              */
    FLOAT32     lambda;             /* put in value for lambda      */
    FLOAT32     min_error;          /* parameter                    */
    LANC_CELLS  *cells;             /* point to array of ANC_CELLS  */
} LANC_Context;

extern LANC_Context *
LANC_Init(
    INT32       num_cells,          /* number of cells              */
    FLOAT32     lambda,             /* lambda param                 */
    FLOAT32     min_error);         /* min error                    */ extern VOID
LANC_Done(
    LANC_Context        *c);

extern VOID
LANC_Reset(
    LANC_Context        *anc);
```

```
extern FLOAT32
LANC_Calc(
    LANC_Context    *anc,    /* input, context handle      */
    FLOAT32         nps,     /* input, noise plus signal   */
    FLOAT32         noise);  /* input, noise reference     */

/* The following macros provide efficient access to the lattice */ define ANC_CELL_SIZE   11 define xBERR       0
define xBERR_1     1
#define xDELTA      2
#define xDELTA_1    3
#define xGAMMA      4
#define xGAMMA_1    5
#define xBSERR      6
#define xBSERR_1    7
#define xERR        8
#define xFERR       9
define xRho        10 define berr            (*(p + xBERR))
define P_berr_1        (*(p + xBERR_1 - ANC_CELL_SIZE))
#define P_berr          (*(p + xBERR   - ANC_CELL_SIZE))
#define berr_1          (*(p + xBERR_1))

#define Bserr           (*(p + xBSERR))
#define Bserr_1         (*(p + xBSERR_1))
#define P_Bserr_1       (*(p + xBSERR_1 - ANC_CELL_SIZE))

#define P_delta         (*(p + xDELTA - ANC_CELL_SIZE))
#define delta           (*(p + xDELTA))
#define delta_1         (*(p + xDELTA_1))
#define P_delta_1       (*(p + xDELTA_1 - ANC_CELL_SIZE))

#define err             (*(p + xERR))
#define N_err           (*(p + xERR + ANC_CELL_SIZE))

#define P_ferr          (*(p + xFERR - ANC_CELL_SIZE))
#define ferr            (*(p + xFERR))

#define gamma           (*(p + xGAMMA))
#define P_gamma         (*(p + xGAMMA   - ANC_CELL_SIZE))
#define N_gamma         (*(p + xGAMMA   + ANC_CELL_SIZE))
#define P_gamma_1       (*(p + xGAMMA_1 - ANC_CELL_SIZE))
#define gamma_1         (*(p + xGAMMA_1))

#define rho             (*(p + xRho))

/* ----------------------------------------------------------------
   Name: LANC_Init Abstract: Create an ANC context

---------------------------------------------------------------- */
```

```
extern LANC_Context *
LANC_Init(
    INT32       num_cells,      /* number of cells       */
    FLOAT32     lambda,         /* lambda param          */
    FLOAT32     min_error) {    /* min error             */

LANC_Context    *anc;       /* context               */ anc = (LANC_Context *)malloc(sizeof(LANC_Context));
    assert(anc != NULL);
    anc->cc = num_cells;
    anc->lambda = lambda;
    anc->min_error = min_error;
    anc->cells = (LANC_CELLS *)malloc(sizeof(LANC_CELLS) * (num_cells + 2));
    assert(anc->cells != NULL);

return(anc);
}

/* ----------------------------------------------------------------------
   Name: LANC_Reset Abstract: Reset an ANC context

---------------------------------------------------------------------- */ extern VOID
LANC_Reset(
    LANC_Context *anc) {

FLOAT32         *p;
    INT32           m;

p = (FLOAT32 *)anc->cells;
    for (m = 0; m <= anc->cc; m++) {
        rho     = 0.0;
        err     = 0.0;
        ferr    = 0.0;
        berr    = 0.0;
        berr_1  = 0.0;
        delta   = 0.0;
        delta_1 = 0.0;
        Bserr   = anc->min_error;
        Bserr_1 = anc->min_error;
        gamma   = MIN_VAL;
        gamma_1 = MIN_VAL;
        p       += ANC_CELL_SIZE;
    }
    p = (FLOAT32 *)anc->cells;          /* Cell # 0 special case  */
    gamma   = 1.0;
    gamma_1 = 1.0;
}

/* ----------------------------------------------------------------------
   Name: LANC_Done Abstract: Delete an ANC context

---------------------------------------------------------------------- */
```

```
extern VOID
LANC_Done(
    LANC_Context      *anc) { free(anc->cells);
    free(anc);
}

/* ----------------------------------------------------------------
   Name: LANC_Calc Abstract: Calculate

---------------------------------------------------------------- */

FLOAT32
LANC_Calc(
    LANC_Context      *anc,     /* input, context handle     */
    FLOAT32           nps,      /* input, noise plus signal  */
    FLOAT32           noise)    /* input, noise reference    */
{
    INT32      m;
    FLOAT32    *p;
    FLOAT32    B,F,B2,F2;
    FLOAT32    qd2,qd3;
    INT32      output_cell;

/* Update time delay elements in cell structure --------------- */ p = (FLOAT32 *)anc->cells;
    for (m = 0; m <= anc->cc; m++) {
        gamma_1 = gamma;
        berr_1  = berr;
        Bserr_1 = Bserr;
        delta_1 = delta;
        p += ANC_CELL_SIZE;
    }

/* Handle Cell # 0 -------------------------------------------- */
    p = (FLOAT32 *)anc->cells;
    Bserr = anc->lambda * Bserr_1 + noise * noise;
    Bserr = MAX(Bserr, MIN_BSERR);

ferr  = noise / SQRTF(Bserr);
    ferr  = MAX(ferr, MIN_DEL);
    ferr  = MIN(ferr, MAX_DEL);

berr  = ferr;

rho = anc->lambda * SQRTF(Bserr_1 / Bserr) * rho + berr * nps;

N_err = nps - rho * berr;

output_cell = anc->cc - 1;      /* Assume last cell for starter */ for (m = 1; m < anc->cc; m++) {
        p += ANC_CELL_SIZE;

B   = SQRTF(1.0 - P_berr_1 * P_berr_1);     B2 = 1.0/B;
```

```
        F      = SQRTF(1.0 - P_ferr    * P_ferr );      F2 = 1.0/F;

P_delta = P_delta_1 * F * B + P_berr_1 * P_ferr;
        P_delta = MAX(P_delta, MIN_DEL);
        P_delta = MIN(P_delta, MAX_DEL);
        qd3    = 1.0 - P_delta * P_delta;
        qd2    = 1.0 / SQRTF(qd3);

ferr   = (P_ferr    - P_delta * P_berr_1) * qd2 * B2;
        ferr   = MAX(ferr, MIN_DEL);
        ferr   = MIN(ferr, MAX_DEL);

berr   = (P_berr_1  - P_delta * P_ferr   ) * qd2 * F2;
        berr   = MAX(berr, MIN_DEL);
        berr   = MIN(berr, MAX_DEL);

gamma = P_gamma * (1.0 - P_berr * P_berr);
        gamma = MAX(gamma, MIN_VAL);
        gamma = MIN(gamma, MAX_DEL);

Bserr = P_Bserr_1 * qd3;

Bserr  = MAX(Bserr, MIN_BSERR);

rho   *= anc->lambda * SQRTF((Bserr_1 / Bserr) * (gamma / gamma_1));
        rho   += berr * err;
        rho    = MAX(rho, MIN_RHO);
        rho    = MIN(rho, MAX_RHO);

N_err = err - rho * berr;
    }
    p = (FLOAT32 *)&(anc->cells[output_cell /* *ANC_CELL_SIZE */]);
    return(N_err);
}
```

APPENDIX D

```
/*      QRD                     */ include <stdlib.h>
include <math.h> define TRUE            1
define FALSE           0 define FLOAT32         float
define INT32           long int
define VOID            void define FABSF           fabs
define SQRTF           sqrt typedef struct {
    INT32       dummy;
} LQRDJPEF_CONTEXT;

typedef LQRDJPEF_CONTEXT * LQRDJPEF_Handle;

extern LQRDJPEF_Handle
LQRDJPEF_Init(
    INT32       NumCells,
    FLOAT32     Lambda,
    FLOAT32     SumErrInit,
    FLOAT32     GamsInit,
    FLOAT32     MinSumErr);

extern VOID
LQRDJPEF_Done(
    LQRDJPEF_Handle hJPE);

extern VOID
LQRDJPEF_Reset(
    LQRDJPEF_Handle hJPE);

extern FLOAT32
LQRDJPEF_Calc(
    LQRDJPEF_Handle hJPE,   /* handle                   */
    FLOAT32  nps,           /* noise plus signal        */
    FLOAT32  noise);        /* noise reference          */ define MAX(a,b)  (a) > (b) ? (a) : (b)
define MIN(a,b)  (a) < (b) ? (a) : (b)

define LQRDJPEF_CELL_SIZE              27 typedef struct {
        FLOAT32 sinf , sinf_1 ;
        FLOAT32 sinb , sinb_1 ;

FLOAT32 cosf , cosf_1 ;
        FLOAT32 cosb , cosb_1 ;

FLOAT32 epsf;
```

```
        FLOAT32 epsb , epsb_1 ;

FLOAT32 pief , pief_1 ;
        FLOAT32 pieb , pieb_1 ;

FLOAT32 Fserr, Fserr_1, SQRTF_Fserr, SQRTF_Fserr_1;
        FLOAT32 Bserr_1, Bserr_2, SQRTF_Bserr_1, SQRTF_Bserr_2;

FLOAT32 p_1, p_2;
        FLOAT32 gams_1;
        FLOAT32 epsi_1;

} LQRDJPEF_CELL;

typedef struct {
        INT32           NumCells;         /* number of cells                */
        FLOAT32         Lambda;           /* Lambda                         */
        FLOAT32         SumErrInit;       /* Initial value for Fserr, Bserr */
        FLOAT32         GamsInit;         /* Initial value for gams         */
        FLOAT32         MinSumErr;        /* Minimum for Fserr, Bserr       */
        FLOAT32         SQRTF_Lambda;     /* square root of Lambda          */
        FLOAT32         SQRTF_SumErrInit; /* square root of SumErrInit      */
        LQRDJPEF_CELL   *cells;           /* point to array of JPE_CELLS    */
} LQRDJPEF_Context;

/*      The following macros provide efficient access to the lattice

Define variables offsets within structure                           */ define xSINF            0
define xSINF_1          1
#define xSINB            2
define xSINB_1          3 define xCOSF            4
define xCOSF_1          5
#define xCOSB            6
define xCOSB_1          7 define xEPSF            8
define xEPSB            9
define xEPSB_1         10 define xPIEF           11
define xPIEF_1         12
#define xPIEB           13
define xPIEB_1         14 define xFSERR          15
define xFSERR_1        16
#define xSQRTF_FSERR    17
define xSQRTF_FSERR_1  18 define xBSERR_1        19
define xBSERR_2        20
#define xSQRTF_BSERR_1  21
define xSQRTF_BSERR_2  22 define xp_1            23
define xp_2            24
```

```
#define xGAMSQ_1         25
define xEPSI_1          26 define sinf             (*(ptr + xSINF))
define sinf_1           (*(ptr + xSINF_1))
#define P_sinf           (*(ptr + xSINF   - LQRDJPEF_CELL_SIZE))
#define P_sinf_1         (*(ptr + xSINF_1 - LQRDJPEF_CELL_SIZE))

#define sinb             (*(ptr + xSINB))
#define sinb_1           (*(ptr + xSINB_1))
#define P_sinb           (*(ptr + xSINB   - LQRDJPEF_CELL_SIZE))
#define P_sinb_1         (*(ptr + xSINB_1 - LQRDJPEF_CELL_SIZE))

#define cosf             (*(ptr + xCOSF))
#define cosf_1           (*(ptr + xCOSF_1))
#define P_cosf           (*(ptr + xCOSF   - LQRDJPEF_CELL_SIZE))
#define P_cosf_1         (*(ptr + xCOSF_1 - LQRDJPEF_CELL_SIZE))

#define cosb             (*(ptr + xCOSB))
#define cosb_1           (*(ptr + xCOSB_1))
#define P_cosb           (*(ptr + xCOSB   - LQRDJPEF_CELL_SIZE))
#define P_cosb_1         (*(ptr + xCOSB_1 - LQRDJPEF_CELL_SIZE))

#define epsf             (*(ptr + xEPSF))
#define P_epsf           (*(ptr + xEPSF   - LQRDJPEF_CELL_SIZE))

#define epsb             (*(ptr + xEPSB))
#define epsb_1           (*(ptr + xEPSB_1))
#define P_epsb           (*(ptr + xEPSB   - LQRDJPEF_CELL_SIZE))
#define P_epsb_1         (*(ptr + xEPSB_1 - LQRDJPEF_CELL_SIZE))

#define pief             (*(ptr + xPIEF))
#define pief_1           (*(ptr + xPIEF_1))
#define P_pief           (*(ptr + xPIEF   - LQRDJPEF_CELL_SIZE))
#define P_pief_1         (*(ptr + xPIEF_1 - LQRDJPEF_CELL_SIZE))

#define pieb             (*(ptr + xPIEB))
#define pieb_1           (*(ptr + xPIEB_1))
#define P_pieb           (*(ptr + xPIEB   - LQRDJPEF_CELL_SIZE))
#define P_pieb_1         (*(ptr + xPIEB_1 - LQRDJPEF_CELL_SIZE))

#define Fserr            (*(ptr + xFSERR))
#define Fserr_1          (*(ptr + xFSERR_1))
#define P_Fserr          (*(ptr + xFSERR   - LQRDJPEF_CELL_SIZE))
#define P_Fserr_1        (*(ptr + xFSERR_1 - LQRDJPEF_CELL_SIZE))
#define SQRTF_Fserr      (*(ptr + xSQRTF_FSERR))
#define SQRTF_Fserr_1    (*(ptr + xSQRTF_FSERR_1))
#define SQRTF_P_Fserr    (*(ptr + xSQRTF_FSERR   - LQRDJPEF_CELL_SIZE))
#define SQRTF_P_Fserr_1  (*(ptr + xSQRTF_FSERR_1 - LQRDJPEF_CELL_SIZE))

#define Bserr_1          (*(ptr + xBSERR_1))
#define Bserr_2          (*(ptr + xBSERR_2))
#define P_Bserr_1        (*(ptr + xBSERR_1 - LQRDJPEF_CELL_SIZE))
#define P_Bserr_2        (*(ptr + xBSERR_2 - LQRDJPEF_CELL_SIZE))
#define SQRTF_Bserr_1    (*(ptr + xSQRTF_BSERR_1))
#define SQRTF_Bserr_2    (*(ptr + xSQRTF_BSERR_2))
#define SQRTF_P_Bserr_1  (*(ptr + xSQRTF_BSERR_1 - LQRDJPEF_CELL_SIZE))
#define SQRTF_P_Bserr_2  (*(ptr + xSQRTF_BSERR_2 - LQRDJPEF_CELL_SIZE))
```

```
#define p_1             (*(ptr + xp_1))
#define p_2             (*(ptr + xp_2))
#define P_p_1           (*(ptr + xp_1      - LQRDJPEF_CELL_SIZE))
#define P_p_2           (*(ptr + xp_2      - LQRDJPEF_CELL_SIZE))

#define gams_1          (*(ptr + xGAMSQ_1))
#define P_gams_1        (*(ptr + xGAMSQ_1  - LQRDJPEF_CELL_SIZE))

#define epsi_1          (*(ptr + xEPSI_1))
#define P_epsi_1        (*(ptr + xEPSI_1   - LQRDJPEF_CELL_SIZE))

static FLOAT32
RSQRTF(
        FLOAT32 x) { return 1.0F / SQRTF(x);
}
/* ------------------------------------------------------------------
   Name         : LQRDJPEF_Init
   Abstract     : Create a JPE context
   ------------------------------------------------------------------ */ extern LQRDJPEF_Handle
LQRDJPEF_Init(
        INT32       NumCells,
        FLOAT32     Lambda,
        FLOAT32     SumErrInit,
        FLOAT32     GamsInit,
        FLOAT32     MinSumErr) {

LQRDJPEF_Context    *jpe;

jpe = malloc(sizeof(LQRDJPEF_Context));
        assert(jpe != NULL);

jpe->NumCells = NumCells;
        jpe->Lambda = Lambda;
        jpe->SumErrInit = SumErrInit;
        jpe->GamsInit = GamsInit;
        jpe->MinSumErr = MinSumErr;
        jpe->SQRTF_Lambda = SQRTF(jpe->Lambda);
        jpe->SQRTF_SumErrInit = SQRTF(jpe->SumErrInit);

jpe->cells = malloc(sizeof(LQRDJPEF_CELL) * (NumCells + 2));
        assert(jpe->cells != NULL);

LQRDJPEF_Reset((LQRDJPEF_Handle)jpe);
        return ((LQRDJPEF_Handle)jpe);
}

/* ------------------------------------------------------------------
   Name         : LQRDJPEF_Done
   Abstract     : Delete a JPE context
   ------------------------------------------------------------------ */ extern VOID
LQRDJPEF_Done(
```

```
            LQRDJPEF_Handle      JPE) {

LQRDJPEF_Context     *jpe = (LQRDJPEF_Context *)hJPE;

free(jpe->cells);
            free(jpe);
}
/* --------------------------------------------------------------------------
    Name        : LQRDJPEF_Reset
    Abstract    : Reset a JPE context
   -------------------------------------------------------------------------- */
extern VOID
LQRDJPEF_Reset(
            LQRDJPEF_Handle      hJPE) {

LQRDJPEF_Context *jpe = (LQRDJPEF_Context *)hJPE;

FLOAT32              *ptr;
            INT32                m;

ptr = (FLOAT32 *)jpe->cells;
            for (m = 0; m <= jpe->NumCells; m++) { sinf     = 0.0F;
            sinb     = 0.0F;
            cosf     = 0.0F;
            cosb     = 0.0F;
            epsf     = 0.0F;
            epsb     = 0.0F;
            pief     = 0.0F;
            pieb     = 0.0F;
            p_1      = 0.0F;
            Fserr    = jpe->SumErrInit;
            Bserr_1  = jpe->SumErrInit;
            gams_1   = jpe->GamsInit;
            SQRTF_Fserr   = jpe->SQRTF_SumErrInit;
            SQRTF_Bserr_1 = jpe->SQRTF_SumErrInit;

ptr     += LQRDJPEF_CELL_SIZE;
            }
            ptr = (FLOAT32 *)jpe->cells;         /* Cell # 0 special case   */
            gams_1 = 1.0F;
}
/* --------------------------------------------------------------------------
    Name        : LQRDJPEF_Calc
    Abstract    :
   -------------------------------------------------------------------------- */
extern FLOAT32
LQRDJPEF_Calc(
            LQRDJPEF_Handle      hJPE,
            FLOAT32   nps,           /* noise plus signal       */
            FLOAT32   noise) {       /* noise reference         */

LQRDJPEF_Context *jpe = (LQRDJPEF_Context *)hJPE;

INT32       m;
```

```
        FLOAT32     *ptr;
        FLOAT32     tmp;
/*      Time update section                                    */ ptr     = (FLOAT32 *)jpe->cells;

for (m = 0; m <= jpe->NumCells; m++) {
        /* some of following delay elements are not needed */ sinf_1  = sinf;
        sinb_1  = sinb;
        cosf_1  = cosf;
        cosb_1  = cosb;
        epsb_1  = epsb;
        pief_1  = pief;
        pieb_1  = pieb;

Fserr_1 = Fserr;
        Bserr_2 = Bserr_1;
        p_2     = p_1;

SQRTF_Bserr_2 = SQRTF_Bserr_1;
        SQRTF_Fserr_1 = SQRTF_Fserr;

ptr += LQRDJPEF_CELL_SIZE;
        }

/*  Order update section   */

/*  Handle Cell # 0        */ ptr = (FLOAT32 *)(jpe->cells); /* point to cell # 0 */
        epsf    = noise;
        epsb    = noise;
        epsi_1  = nps;

/* rest of cells           */ for (m = 1; m < jpe->NumCells; m++) { ptr += LQRDJPEF_CELL_SIZE;      /* access next cell */

/* Prediction section */

P_Bserr_1 = jpe->Lambda * P_Bserr_2 + P_epsb_1 * P_epsb_1;
            P_Bserr_1 = MAX(P_Bserr_1, jpe->MinSumErr);
            SQRTF_P_Bserr_1 = SQRTF(P_Bserr_1);
            tmp = RSQRTF(P_Bserr_1); /* this comes free on DSP */

P_cosb_1  = jpe->SQRTF_Lambda * SQRTF_P_Bserr_2 * tmp;

P_sinb_1  = P_epsb_1 * tmp;

tmp = jpe->SQRTF_Lambda * P_pief_1;
            epsf      = P_cosb_1 * P_epsf - P_sinb_1 * tmp;

P_pief    = P_cosb_1 * tmp + P_sinb_1 * P_epsf;

gams_1    = P_cosb_1 * P_gams_1;
```

```
        P_Fserr    = jpe->Lambda * P_Fserr_1 + P_epsf * P_epsf;
        P_Fserr    = MAX(P_Fserr, jpe->MinSumErr);

SQRTF_P_Fserr = SQRTF(P_Fserr);
        tmp = RSQRTF(P_Fserr);  /* this comes free on DSP */

P_cosf     = jpe->SQRTF_Lambda * SQRTF_P_Fserr_1 * tmp;

P_sinf     = P_epsf * tmp;

tmp = jpe->SQRTF_Lambda * P_pieb_1;
        epsb       = P_cosf * P_epsb_1 - P_sinf * tmp;

P_pieb     = P_cosf * tmp + P_sinf * P_epsb_1;

/* Joint Process Estimation section */ tmp = jpe->SQRTF_Lambda * P_p_2;
        epsi_1     = P_cosb_1 * P_epsi_1 - P_sinb_1 * tmp;

P_p_1      = P_cosb_1 * tmp + P_sinb_1 * P_epsi_1;
    } ptr += LQRDJPEF_CELL_SIZE;  /* access next cell */

/* Do minimum work for JPE of very last cell
       only four equations are required for prediction section */

P_Bserr_1 = jpe->Lambda * P_Bserr_2 + P_epsb_1 * P_epsb_1;
    P_Bserr_1 = MAX(P_Bserr_1, jpe->MinSumErr);

SQRTF_P_Bserr_1 = SQRTF(P_Bserr_1);
    tmp = RSQRTF(P_Bserr_1);  /* this comes free on DSP */

P_cosb_1  = jpe->SQRTF_Lambda * SQRTF_P_Bserr_2 * tmp;

P_sinb_1  = P_epsb_1 * tmp;

/* Joint Process Estimation for last cell      */ tmp = jpe->SQRTF_Lambda * P_p_2;
    epsi_1     = P_cosb_1 * P_epsi_1 - P_sinb_1 * tmp;

P_p_1     = P_cosb_1 * tmp + P_sinb_1 * P_epsi_1;

gams_1    = P_cosb_1 * P_gams_1;

return(gams_1 * epsi_1);
}
```

What is claimed is:

1. A system for the enhancement of physiological signals for the measurement of blood oxygen in a subject, the system comprising:

first and second light sources to direct light toward the subject, said first and second light sources producing light of first and second wavelengths, respectively;

a light detector positioned to detect first and second light signals after interacting with the subject and to generate signals indicative of an intensity of said first and second detected light signals, said first detected signal having a first portion arising from light transmitted from said first source and a second portion arising from a first interference source, said second detected signal having a first portion arising from light transmitted from said second source and a second portion arising from a second interference source;

a storage location containing a mathematical relationship of said first and second portions of said first and second detected signals and a first ratio of said first portion of said first detected signal to said first portion of said second detected signal;

an analyzer coupled to said storage location to determine a plurality of possible values for said mathematical relationship over a predetermined range of said first ratio; and a calculator to determine a selected value from said plurality of possible values for said first ratio based on said plurality of values.

2. The system of claim 1 wherein said analyzer uses an integral function analysis to determine said plurality of values.

3. The system of claim 1 wherein said calculator determines said selected first ratio by finding a maximum value for said plurality of values.

4. The system of claim 1 wherein said storage location contains a second ratio of said second portion of said first detected signal to said second portion of said second detected signal and having a range corresponding to said predetermined range, said calculator determining a selected value for said second ratio by finding a minimum value for said plurality of values.

5. The system of claim 1 wherein said first ratio is indicative of blood oxygen saturation in the subject, the system further including a look-up table containing data relating said first ratio to said blood oxygen saturation.

6. The system of claim 1 wherein said mathematical relationship has the form of a correlation cancellation based upon inputs $S_a(t)$ and $S_a(t)-\omega S_b(t)$ where $S_a(t)$ is said first detected signal, $S_b(t)$ is said second detected signal, and at is a variable defined over a predetermined range.

7. The system of claim 1, further including a statistical analyzer coupled to said calculator to receive a plurality of values for said first ratio over a predetermined period of time, said statistical analyzer analyzing said plurality of selected values for said first ratio and determine a statistical value for said first ratio.

8. The system of claim 7 wherein said statistical value for said first ratio is a mean value for said plurality of selected values for said first ratio.

9. The system of claim 1, further including an adaptive signal processor having a signal input, a reference input, an adaptive filter coupled to said reference input and generating a filter output, a summer coupled to said signal input and said filter output to generate a summer output, said signal input receiving said first detected signal and said reference input receiving a signal derived from said mathematical relationship defined over said predetermined range, said analyzer analyzing said summer output to determine a selected value.

10. A system for the enhancement of physiological signals representative of a physiological phenomenon in a subject, the system comprising:

a sensor configured to be positioned in proximity with the subject to detect physiological signals and to generate signals indicative of said detected physiological signals when positioned in proximity with the subject, said detected signals having a first portion arising from the physiological phenomenon and a second portion arising from an interference source;

an analyzer to analyze and determine a value for said generated signals, said value being indicative of complications of said generated signals; and a processor, responsive to said value, to generate a processed signal.

11. The system of claim 10 wherein said analyzer is a correlation cancellation analyzer determining said value indicative of complications.

12. The system of claim 10 wherein said analyzer determines said value over a predetermined range of possible values and said processor selects a maximum value for said range of possible values.

13. The system of claim 10 wherein said analyzer determines said values over a predetermined range of possible values and said processor selects a minimum value for said range of possible values.

14. The system of claim 10 wherein said value is valid over a predetermined range, and said analyzer selects a value in said predetermined range.

15. The system of claim 10 wherein said processor is an adaptive signal processor having a signal input, a reference input, an adaptive filter coupled to said reference input and generating a filter output, a summer coupled to said signal input and said filter output to generate a summer output, said signal input receiving said detected signals and said reference input receiving a signal derived from a mathematical relationship of said first and second portions of said detected signals, said analyzer analyzing said summer output to determine said value of said summer output.

16. The system of claim 15 wherein said processed signal is said filter output.

17. The system of claim 10 wherein said detected signals are first and second light signals transmitted from first and second light sources having first and second wavelengths, respectively, each of said detected signals having said first and second portions, the system further including a light detector positioned to detect first and second light signals after interacting with the subject and to generate signals indicative of an intensity of said first and second detected light signals, a storage location containing a mathematical relationship of said first and second portions of said first and second detected signals and a first ratio of said first portion of said first detected signal to said first portion of said second detected signal, said analyzer being coupled to said storage location to determine a plurality of values for said mathematical relationship over a predetermined range of said first ratio, said first ratio being based on said plurality of values.

18. The system of claim 17 wherein said analyzer determines said first ratio value by finding a maximum value for said plurality of values.

19. The system of claim 17 wherein said storage location contains a second ratio of said second portion of said first detected signal to said second portion of said second detected signal and having a range corresponding to said predetermined range, said analyzer determining a selected value for said second ratio by finding a minimum value for said plurality of values.

20. The system of claim 17 wherein said first ratio is indicative of blood oxygen saturation in the subject, the system further including a look-up table containing data relating said first ratio to said blood oxygen saturation.

21. A method for enhancement of physiological signals for the measurement of blood oxygen in a subject, the method comprising the steps of:

producing light of first and second wavelengths;

directing light of said first and second wavelengths toward the subject;

detecting first and second light signals after interacting with the subject and generating signals indicative of an intensity of said first and second detected light signals, said first detected signal having a first portion arising from light transmitted with said first wavelength and a second portion arising from a first interference source, said second detected signal having a first portion arising from light transmitted with said second wavelength and a second portion arising from a second interference source;

analyzing said first and second detected signals using a mathematical relationship of said first and second portions of said first and second detected signals and a first ratio of said first portion of said first detected signal to said first portion of said second detected signal to determine a plurality of possible values for said mathematical relationship over a predetermined range of said first ratio; and determining a selected value from said plurality of possible values for said first ratio based on said plurality of values.

22. The method of claim 21 wherein said step of analyzing uses an integral function analysis to determine said plurality of values.

23. The method of claim 21 wherein said step of determining said selected value selects a maximum value for said plurality of values.

24. The method of claim 21 wherein said mathematical relationship contains a second ratio of said second portion of said first detected signal to said second portion of said second detected signal, said second ratio having a range corresponding to said predetermined range, said step of determining also determining a selected value for said second ratio by finding a minimum value for said plurality of values.

25. A method for the enhancement of physiological measurements in a subject, the method comprising the steps of:

using a plurality of light sources, each producing light of a different predetermined wavelength;

directing light of said predetermined wavelengths toward the subject;

detecting a plurality of light signals after interacting with the subject and generating signals indicative of an intensity of said plurality of detected light signals, each of said detected signals having a first portion arising from light transmitted with one of said predetermined wavelength and a second portion arising from an interference source;

analyzing said plurality of detected signals using a mathematical relationship of said first and second portions of said plurality of detected signals and a first ratio of said first portion of a first of said plurality of detected signals to said first portion of a second of said plurality of detected signals to determine a plurality of possible values for said mathematical relationship over a predetermined range of said first ratio; and determining a selected value from said plurality of possible values for said first ratio based on said plurality of values.

26. The method of claim 25 wherein said step of analyzing uses an integral function analysis to determine said values.

27. A method for the enhancement of physiological signals representative of a physiological phenomenon in a subject, the method comprising the steps of:

positioning a sensor in proximity with the subject to detect physiological signals and to generate signals indicative of said detected physiological signals, said detected signals having a first portion arising from the physiological phenomenon and a second portion arising from an interference source;

analyzing said generated signals to determine a value for said generated signals, said value being indicative of complications of said generated signals; and processing said generated signals using said value to generate processed signals.

28. The method of claim 27 wherein said step of analyzing uses an integral function analysis to determine said value.

* * * * *